US006969704B1

(12) United States Patent
Pinsky et al.

(10) Patent No.: US 6,969,704 B1
(45) Date of Patent: Nov. 29, 2005

(54) METHODS FOR SUPPRESSING EARLY GROWTH RESPONSE—1PROTEIN (EGR-1) TO REDUCE VASCULAR INJURY IN A SUBJECT

(75) Inventors: David Pinsky, Cresskill, NJ (US); David M. Stern, Great Neck, NY (US); Shi-Fang Yan, New York, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 17 days.

(21) Appl. No.: 09/648,389

(22) Filed: Aug. 25, 2000

(51) Int. Cl.[7] ...................... A61K 31/07; A01N 43/04; C07H 21/04; C12Q 1/68
(52) U.S. Cl. ..................... 514/44; 536/23.1; 536/24.3; 536/24.33; 536/24.5
(58) Field of Search ............................. 536/23.1, 24.1, 536/24.5; 435/375; 514/44, 2

(56) References Cited

U.S. PATENT DOCUMENTS 5,593,974 A * 1/1997 Rosenberg et al. ........... 514/44

OTHER PUBLICATIONS

Gewirtz et al. Facilitating oligonucleotide delivery: Helping antisense deliver on its promise. Proc. Natl. Acad. Sci, 1996 vol. 93:3161–3163).*
SL Lee et al., Science, Luteinizing Hormone Deficiency and Female Infertility in Mice Lacking the Transcription Factor NGGI–A (Egr–1) Aug. 1996, vol. 273, pp. 1219–1221.*
P Topilko et al., Molecular Endocrinology, "Multiple Pituitary and Ovarian Defects in Krox–24 (NGFI–A, Egr–1)–Targeted Mice," 1998, 12: pp. 107–122.*
E Murphy et al., Circulation Research, "Sodium Regulation During Ischemia Versus Reperfusion and its Role in Injury," 1999, 84:1469–1470.*
DR Meldrum, Journal of Surgical Research, "Mechanims of Cardiac Preconditioning: Ten Years after the Discovery of Ischemic Preconditioning," 1997, 73, pp. 1–13.*
H Yoshidome et al., Journal of Surgicla Research, "Enhanced Pulmonary Expression of CXC Chemokines during Hepatic Ischemia/Reperfusion–Induced Lung Injury in Mice," 1999, 81, pp. 33–37.*
FS Santiago et al., American Journal of Pathology, "Vasular Smooth Muscle Cell Proliferation and Regrowth after Mechanical Injury in Vitro Are Egr–1/NGFI–A–Dependent," Sep. 1999, vol. 155, No. 3, pp. 897–905.*
K–Y Jen et al., Stem Cells, "Suppression of Gene Expression by Targeted Disruption of Messenger RNA: Available Options and Current Strategies," 2000, 18: 307–319.*
AD Branch, TIBS, "A good antisense molecule is hard to find," Feb. 1998, pp. 45–50.*

(Continued)

*Primary Examiner*—Karen A. Lacourcire
*Assistant Examiner*—Terra C. Gibbs
(74) *Attorney, Agent, or Firm*—John P. White, Esq.; Cooper & Dunham LLP

(57) ABSTRACT

The invention provides a method for reducing damage to an ischemic tissue which comprises contacting cells of the tissue with an inhibitor of Early Growth Response Factor-1 Protein (Egr-1). In addition, the invention provides a method for reducing vascular injury during reperfusion of an ischemic tissue in a subject which comprises contacting the tissue with a compound which inhibits expression of Early Growth Response Factor-1 (Egr-1) protein in the tissue so as to reduce vascular injury in the tissue during reperfusion. wherein the inhibitor is a nucleic acid consisting essentially of the polynucleotide sequence 5'-CTTGGCCGCTGCCAT-3' (SEQ ID NO:1). In one embodiment of the invention, the subject has suffered a stroke, or a myocardial infarction. In another embodiment of the invention, the subject is undergoing or has undergone angioplasty, cardiac surgery, vascular surgery, or organ transplantation.

6 Claims, 19 Drawing Sheets

OTHER PUBLICATIONS

Gashler, A. & Sukhatme, V. Egr–1: prototype of a zinc finger fan–lily of transcription factors. Prog. Nucl. Acids Res. and Molec. Biol. 50, 191–224 (1995).

Nguyen, H., Hoffman–Lieberman, B. & Liebennann, D. Egr–1 is essential for and restricts differentiation along the macrophage cell lineage. Cell 72, 197–209 (1993).

Yan, S–F., et al. Tissue factor transcription driven by Egr–1 is a critical mechanism of murine pulmonary fibrin deposition in hypoxia. Proc Natl Acad Sci 95, 8298–8303 (1998).

Okada, K., et al. Potentiation of endogenous fibrinolysis and rescue from lung ischemia–reperfusion injury in IL–10–reconstituted IL–10 null mice. J. Biol. Chem. epub ahead of print (2000).

Lee, S., et al. Early expression of angiogenesis factors in acute myocardial ischemia. New Engl J Med 342, 626–633 (2000).

Liu, P., et al. Role of endogenous nitric oxide in TNF–$\alpha$ and IL–1–1$\beta$ generation in hepatic ischemia–reperfusion. Shock 13, 217–223 (2000).

Mechtcheriakova, D., et al. VEGF–induced tissue factor expression in endothelial cells is mediated by Egr–1. Blood 93, 3 811–3123 (1999).

Khachigian, L., Lindner, V., Williams, A. & Collins, T. Egr–1–induced endothelial gene expression: a common theme in vascular injury. Science 271, 1427–1431 (1996).

* cited by examiner

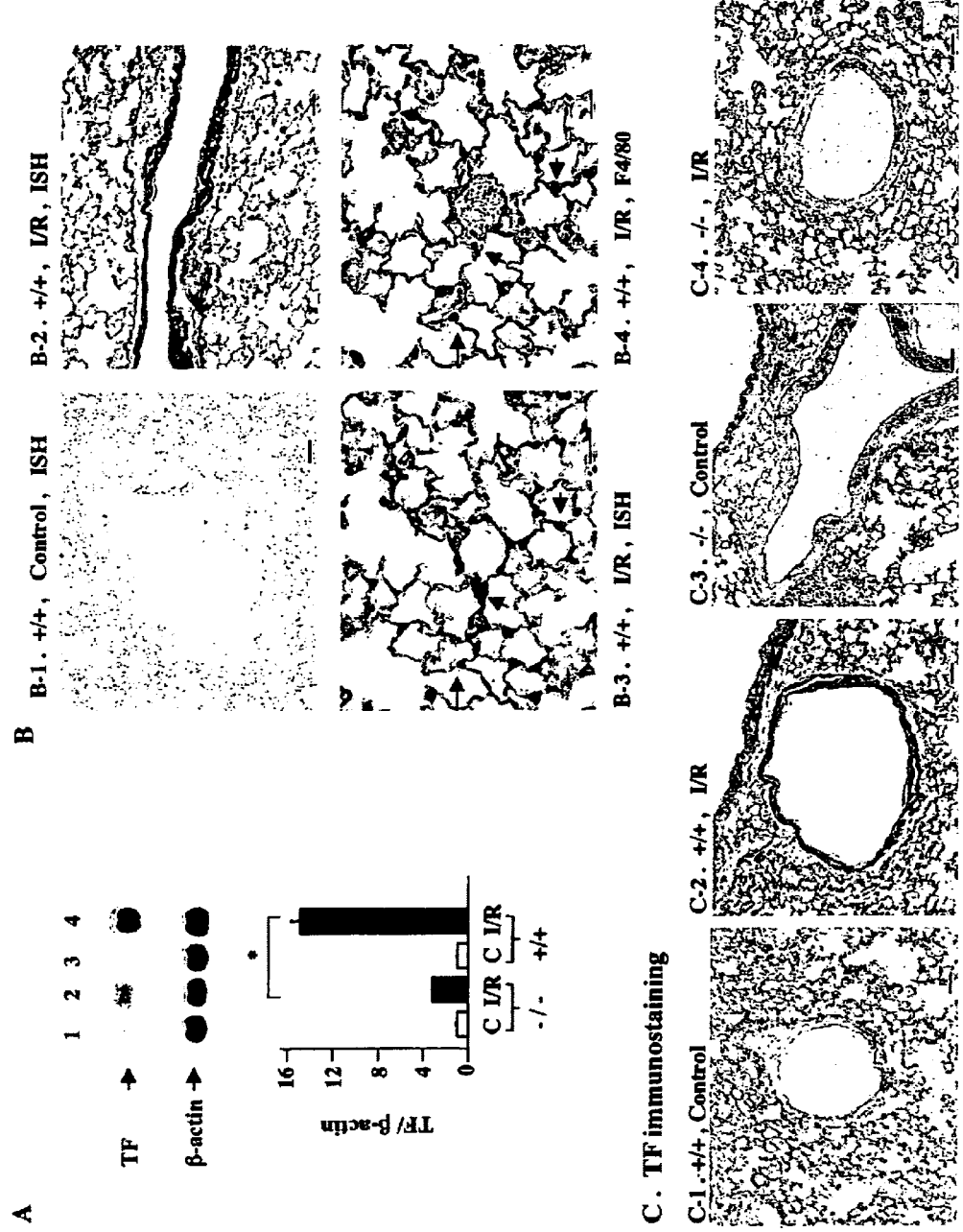
Figure 1 A-C

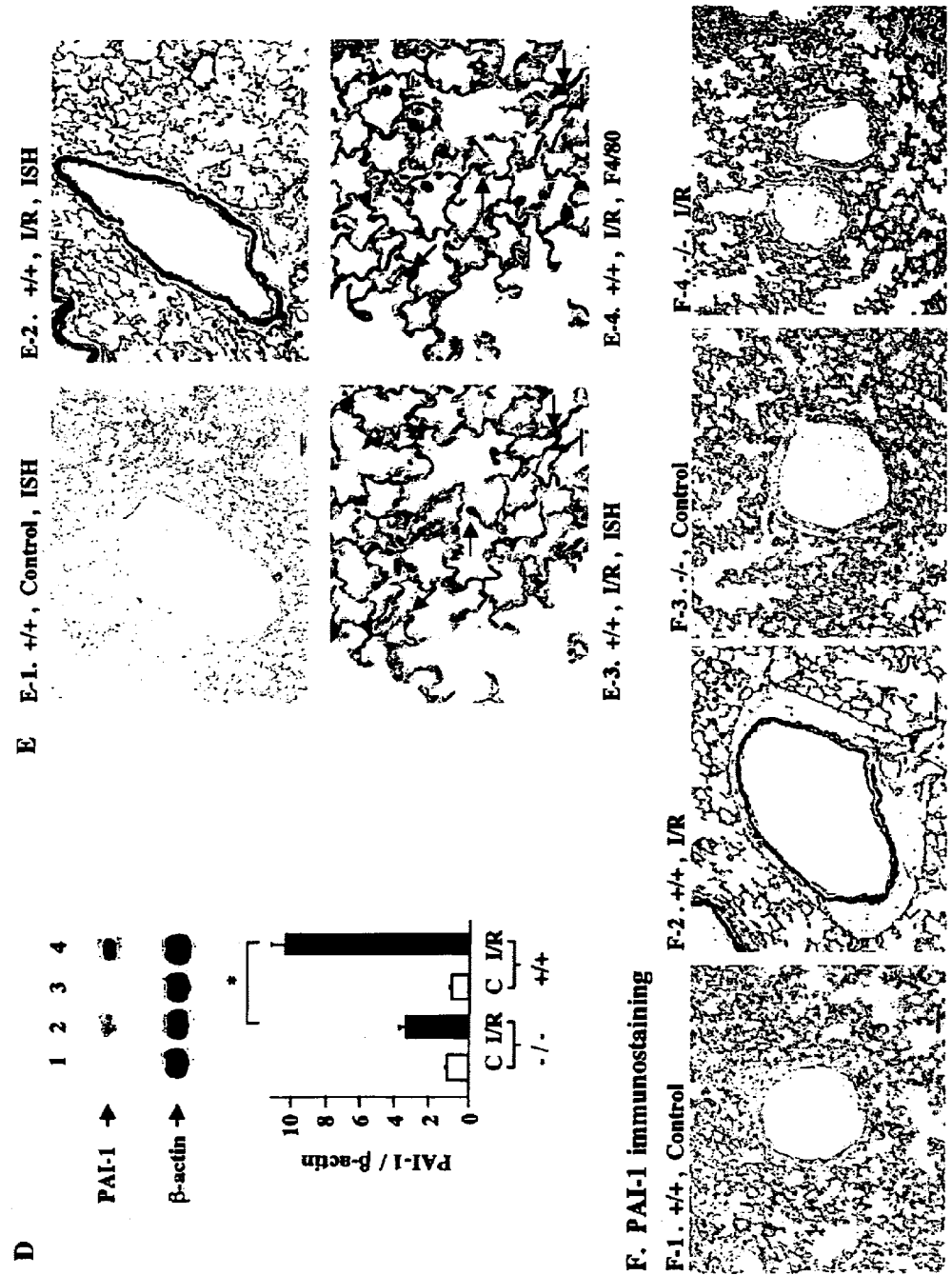
Figure 1 D-F

Figure 2 A-C
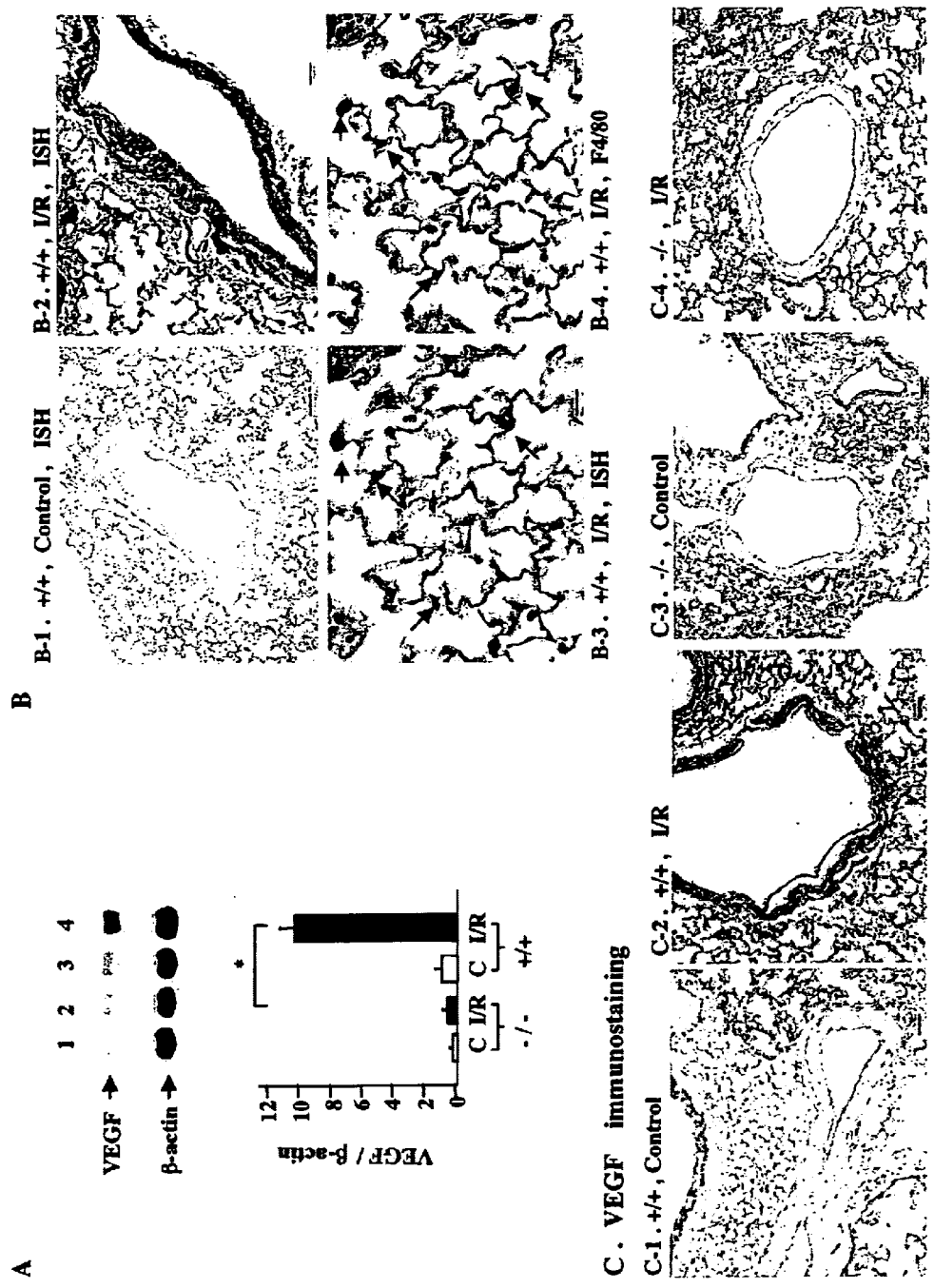

Figure 3 A-C
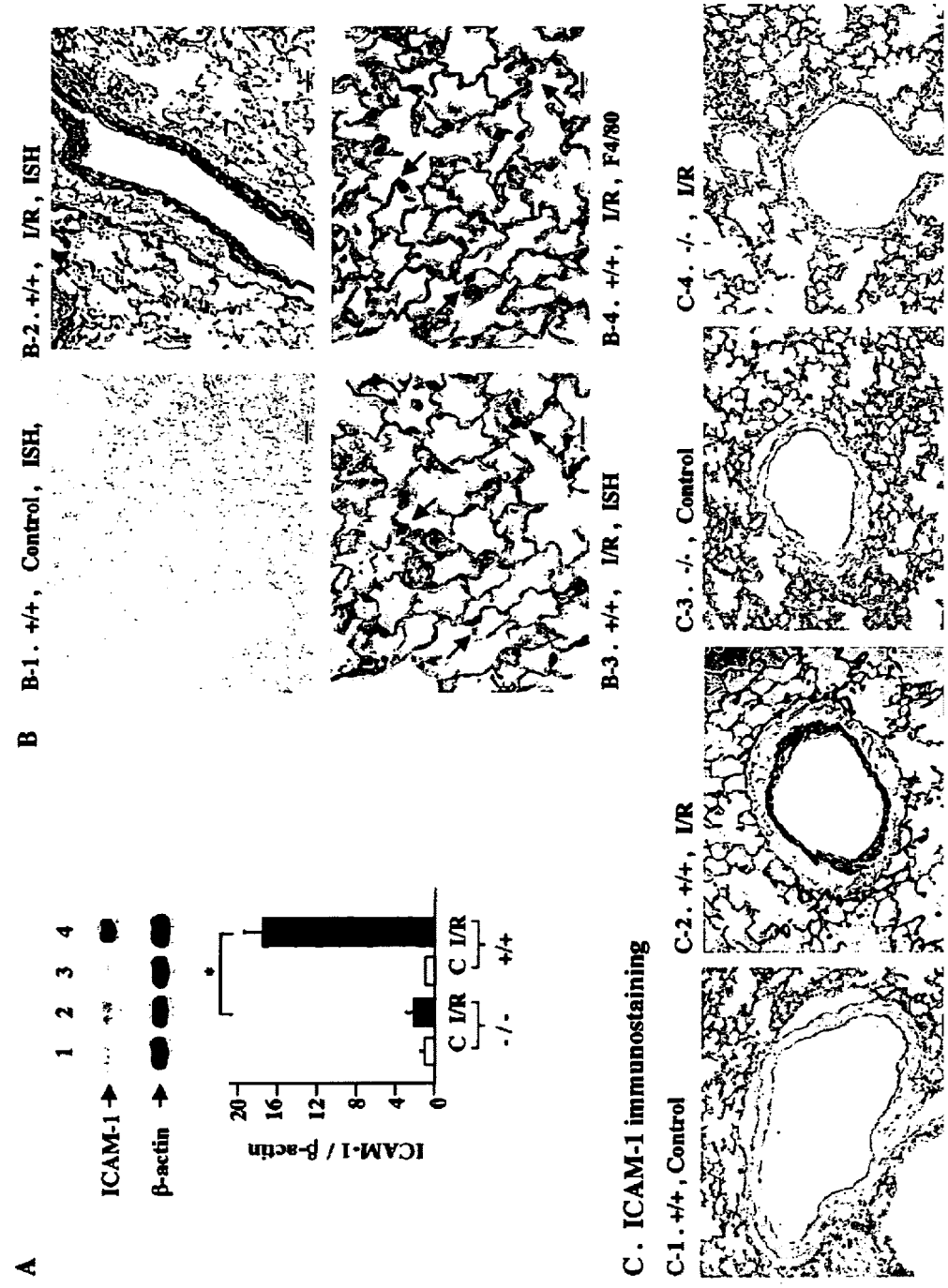

Figure 4 A-C
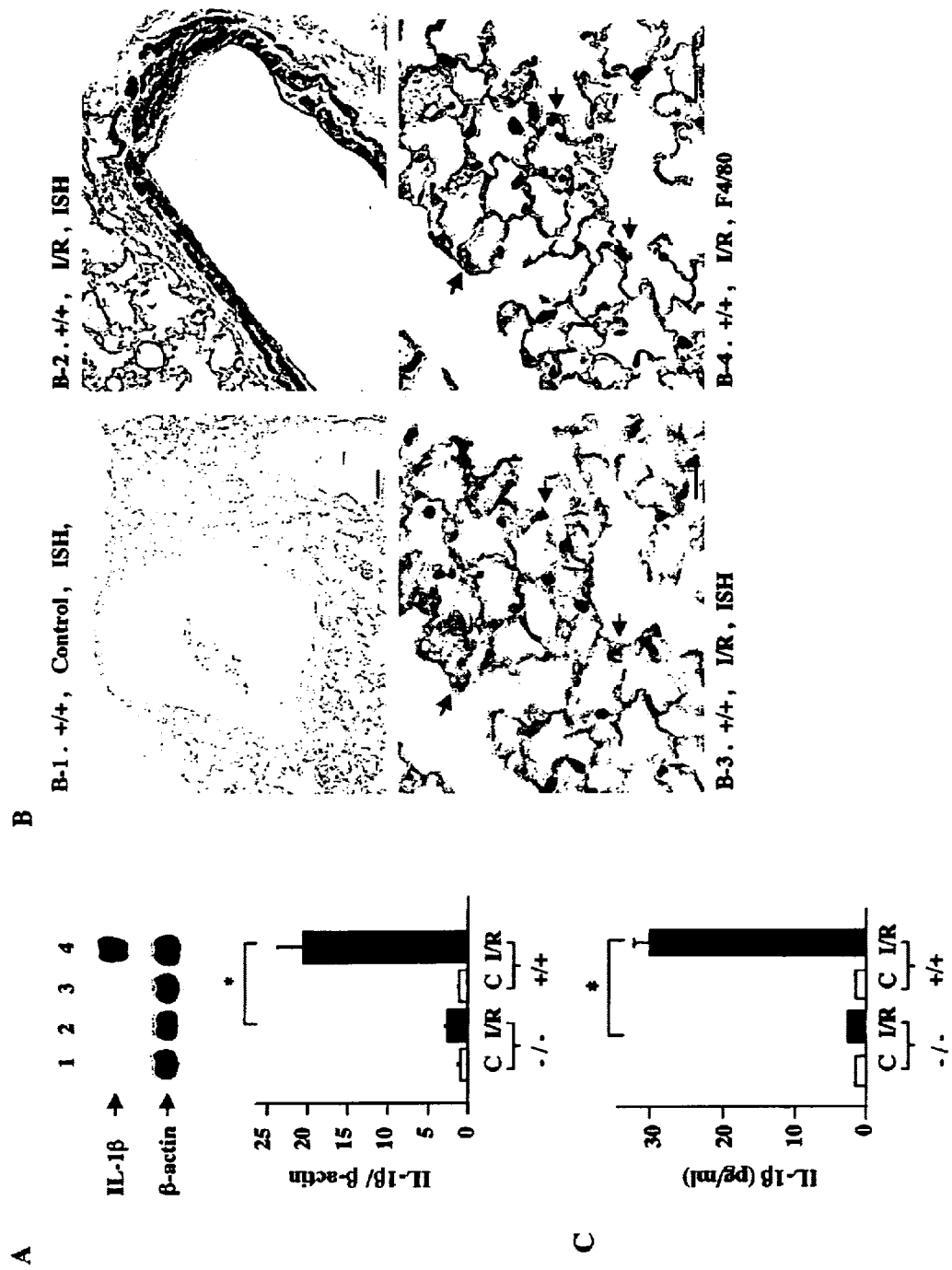

Figure 4 D-F
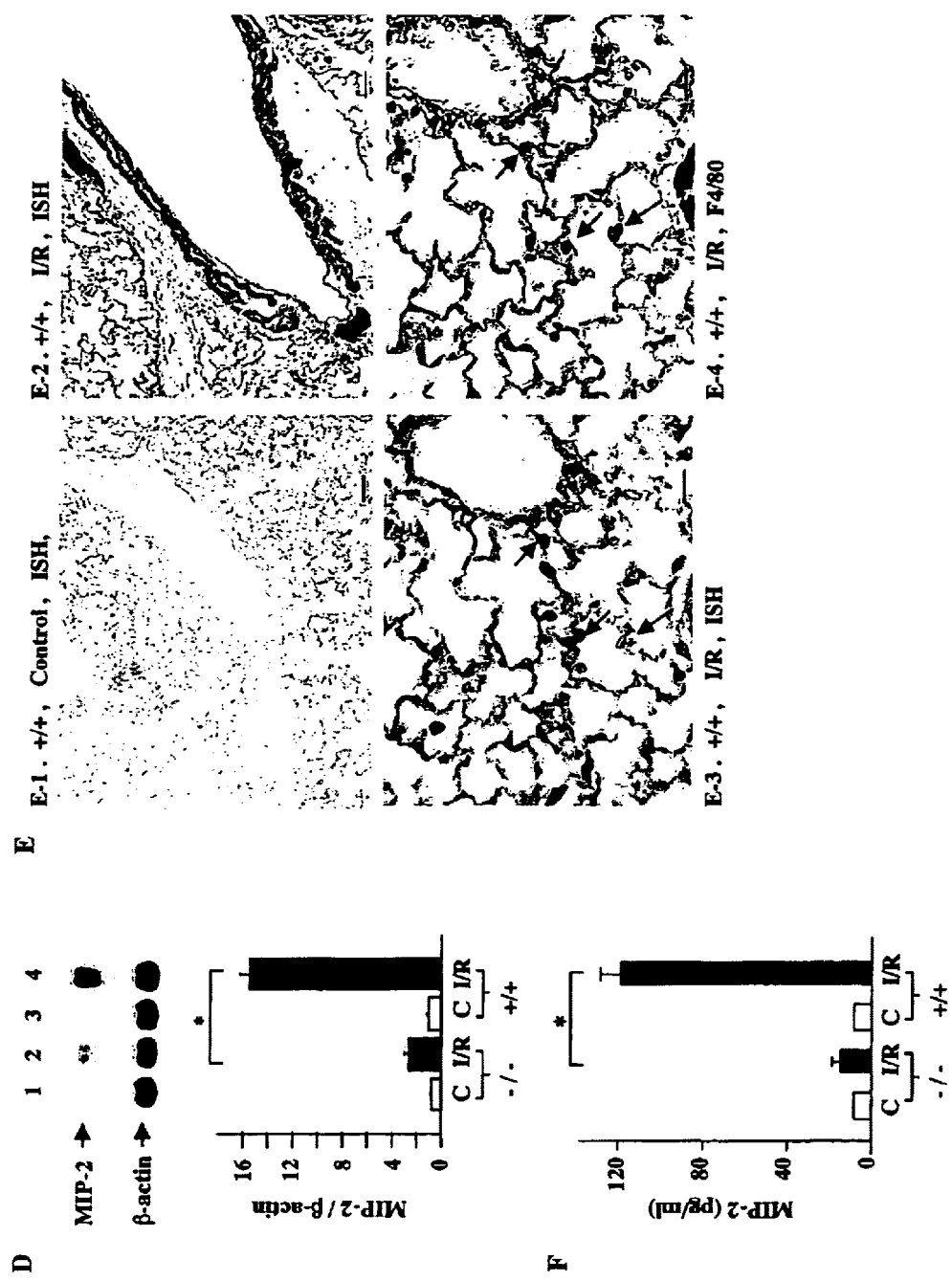

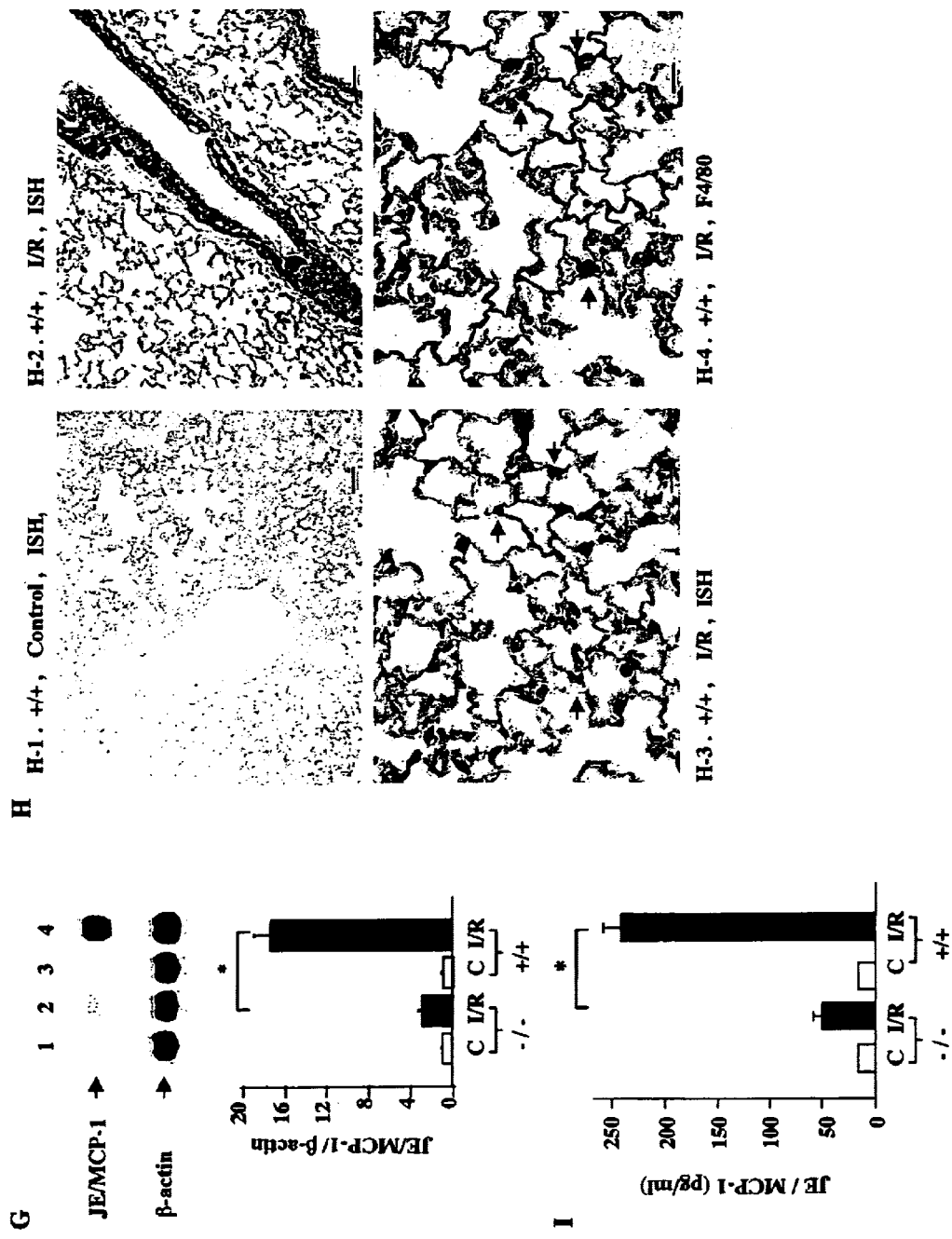
Figure 4 G-I

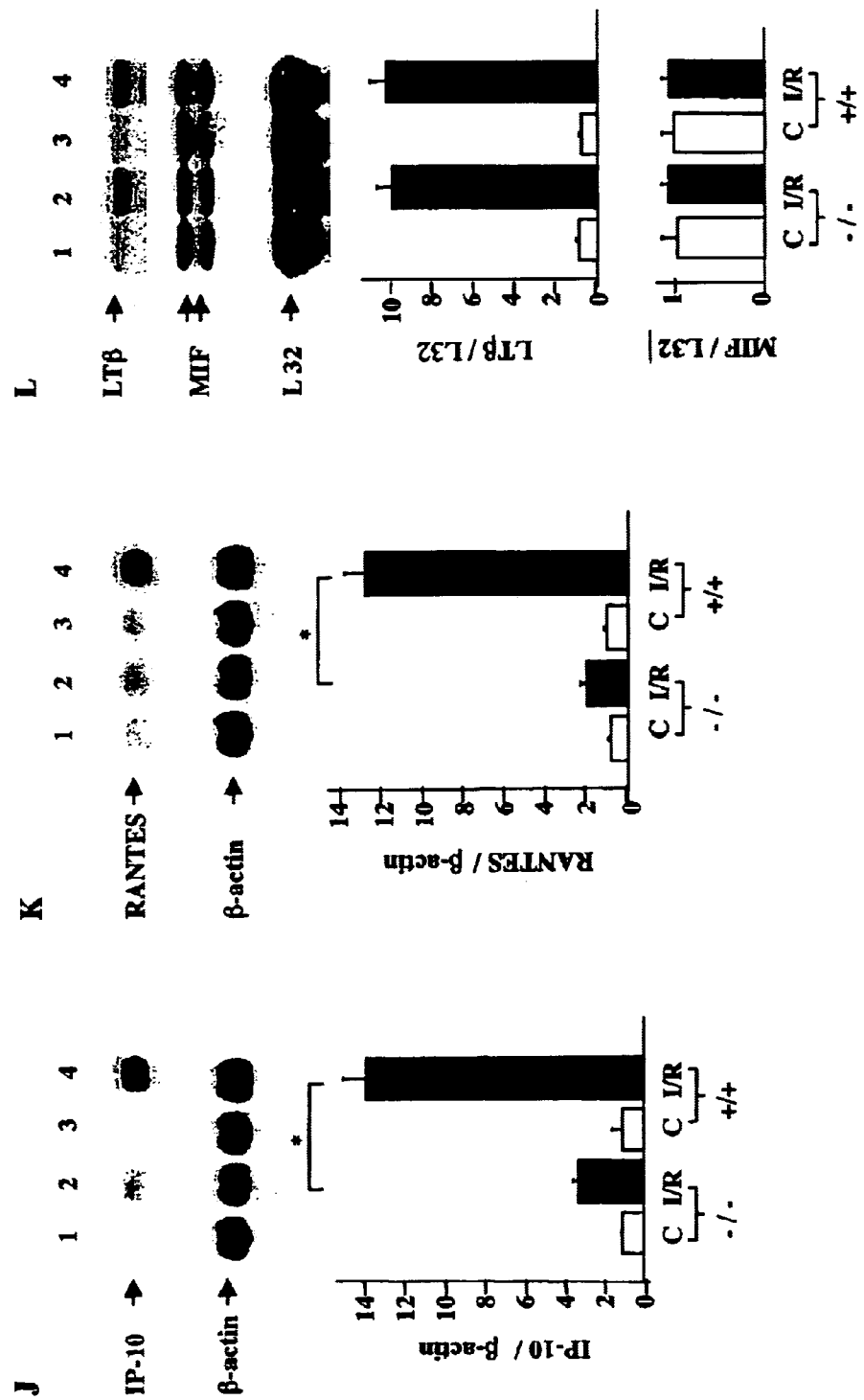
Figure 4 J-L

Figure 5 A-B
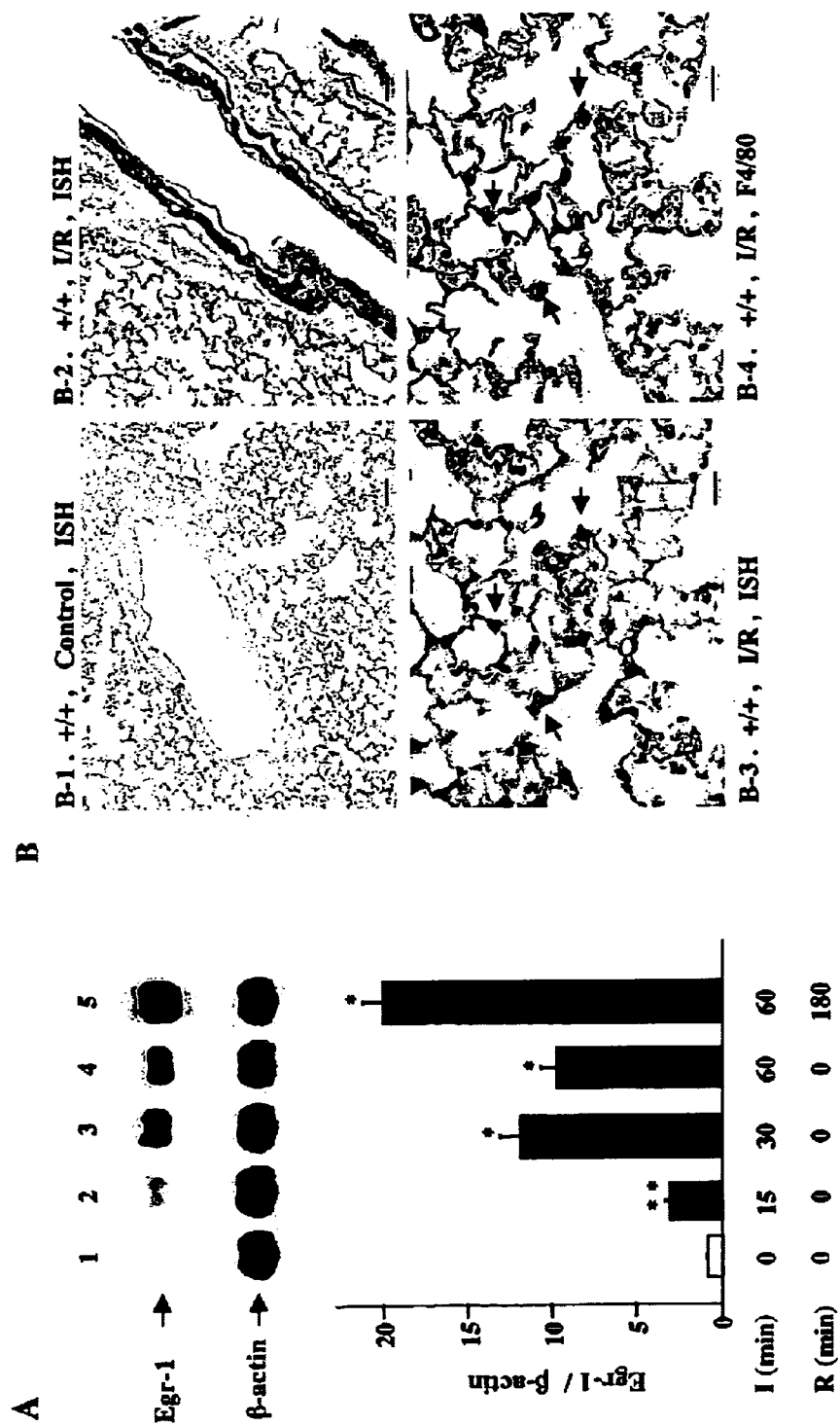

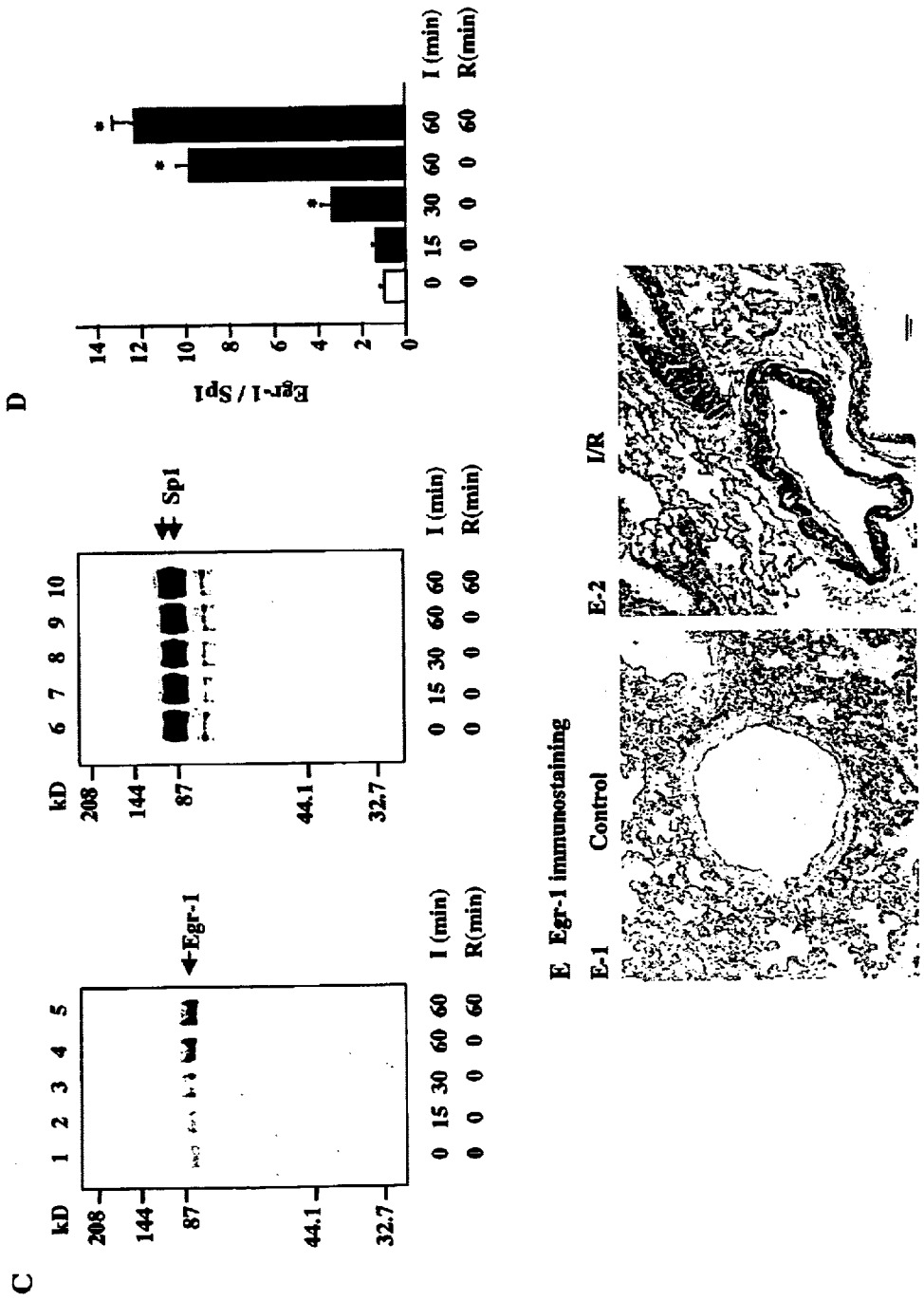
Figure 5 C-E

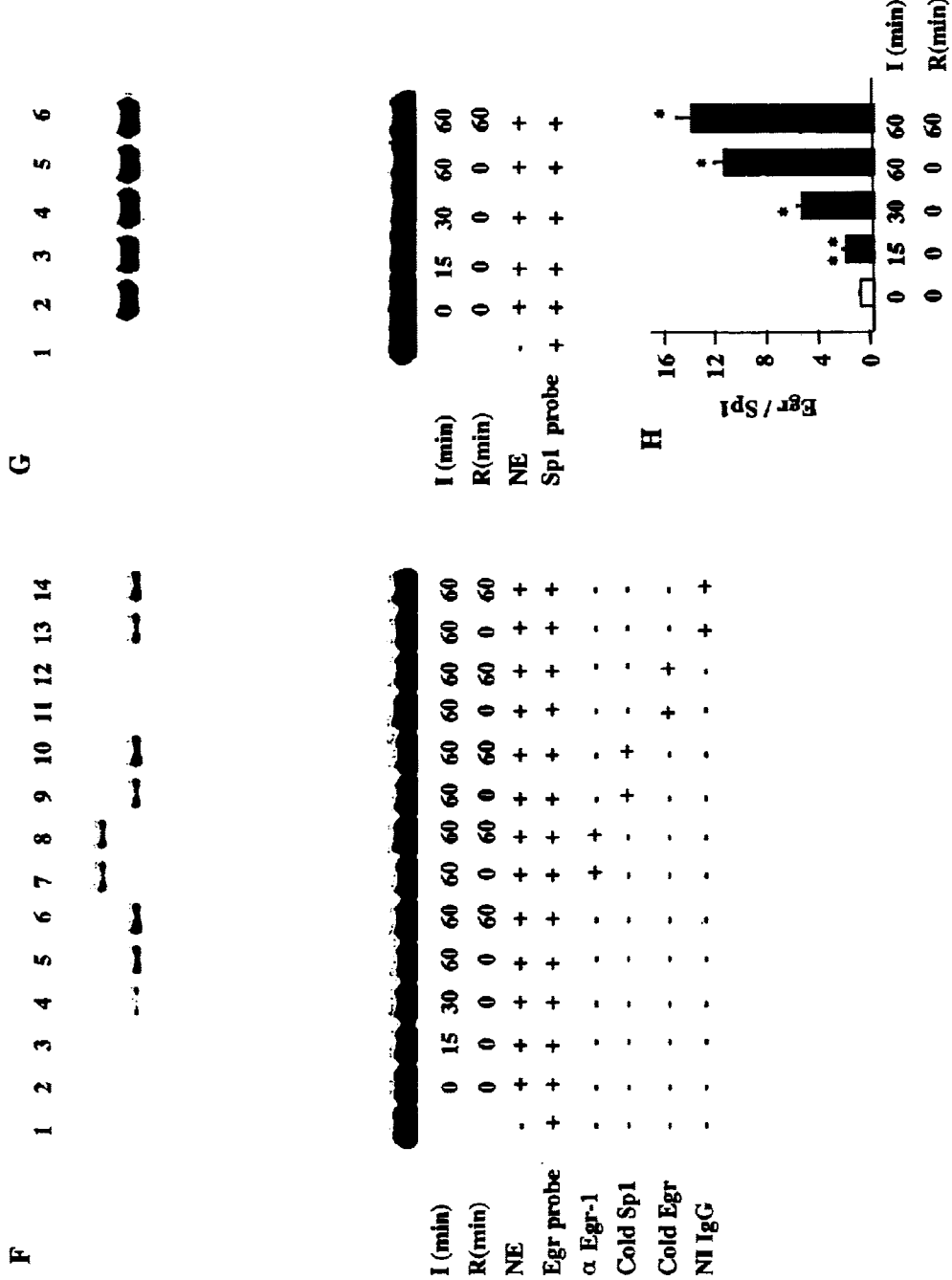
Figure 5 F-H

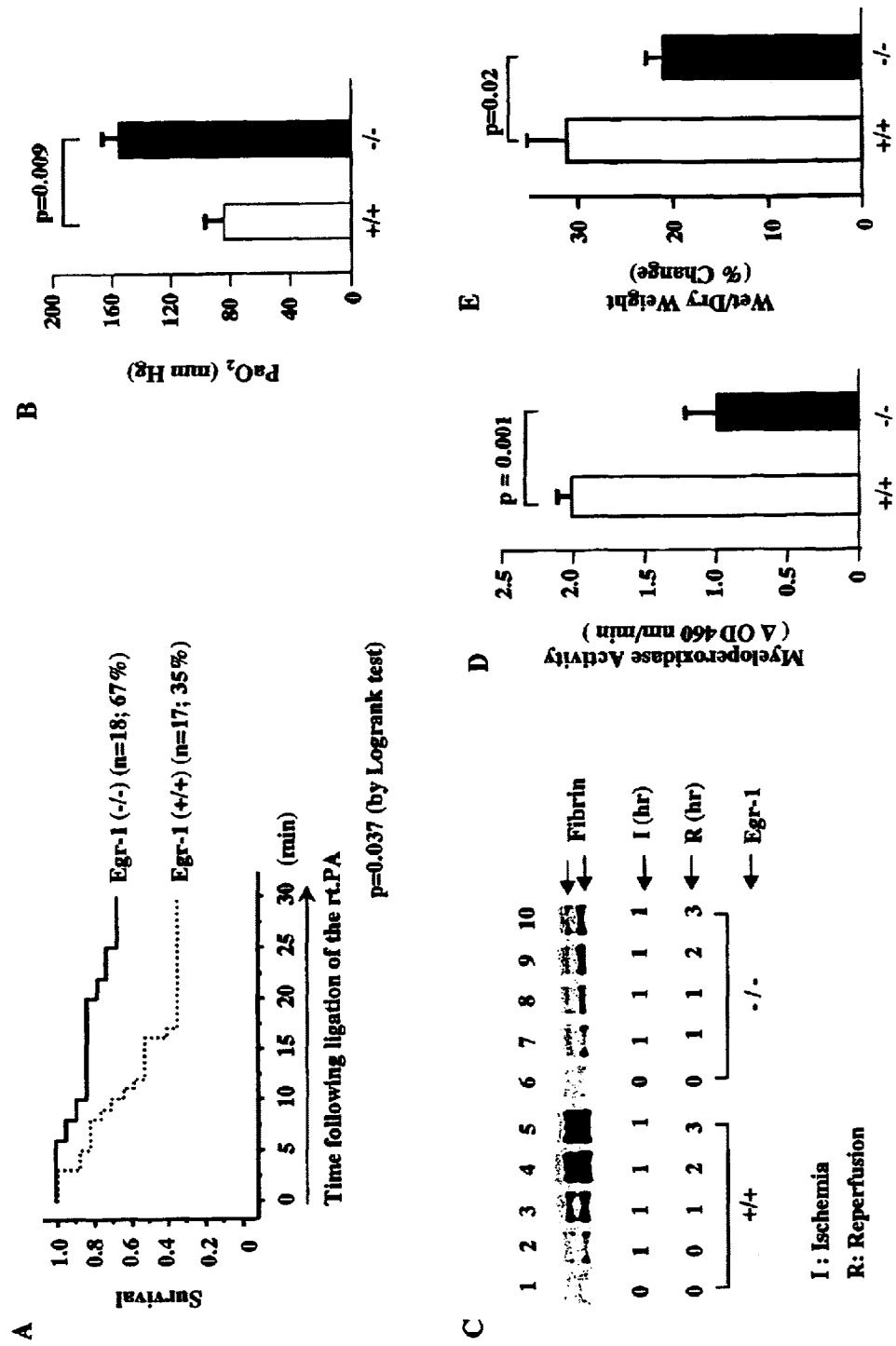
Figure 6 A-E

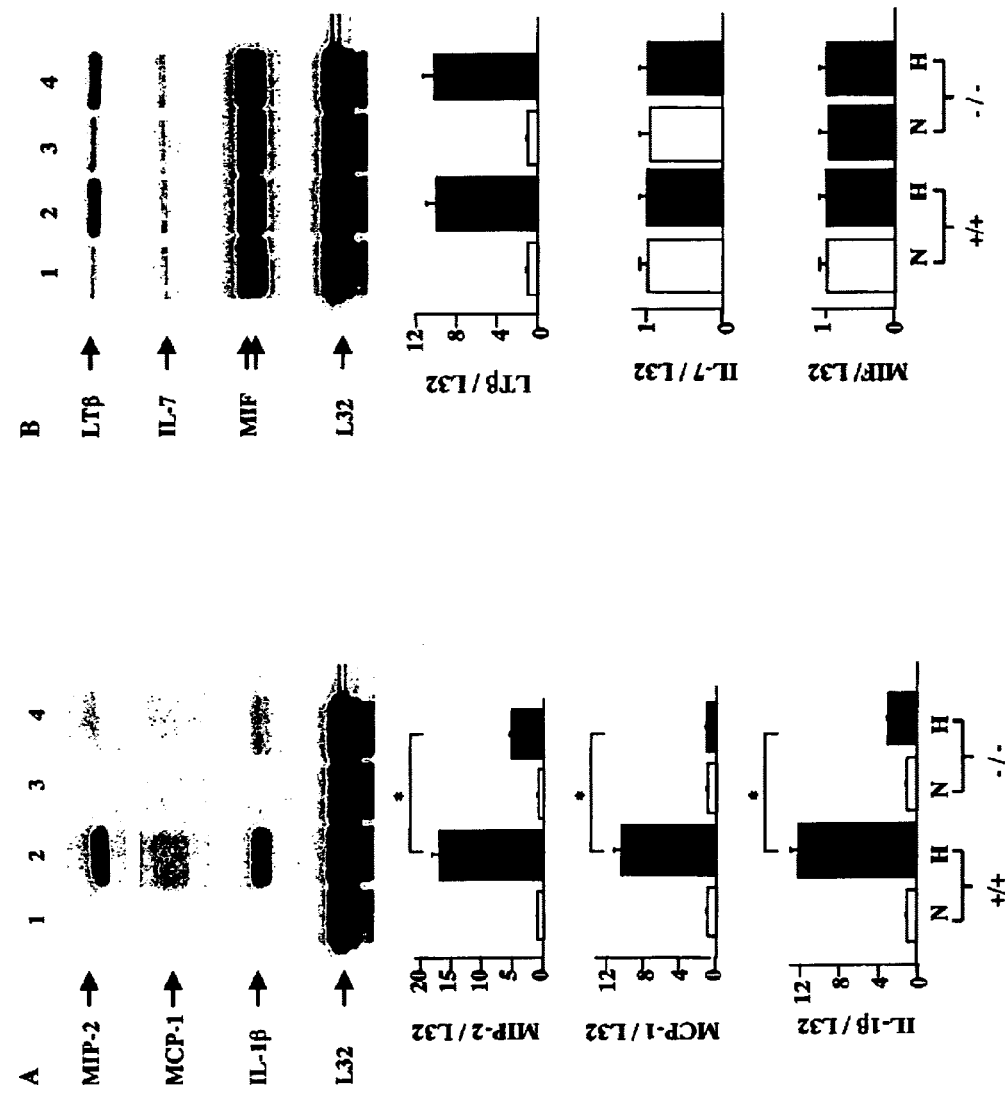
Figure 7 A-B

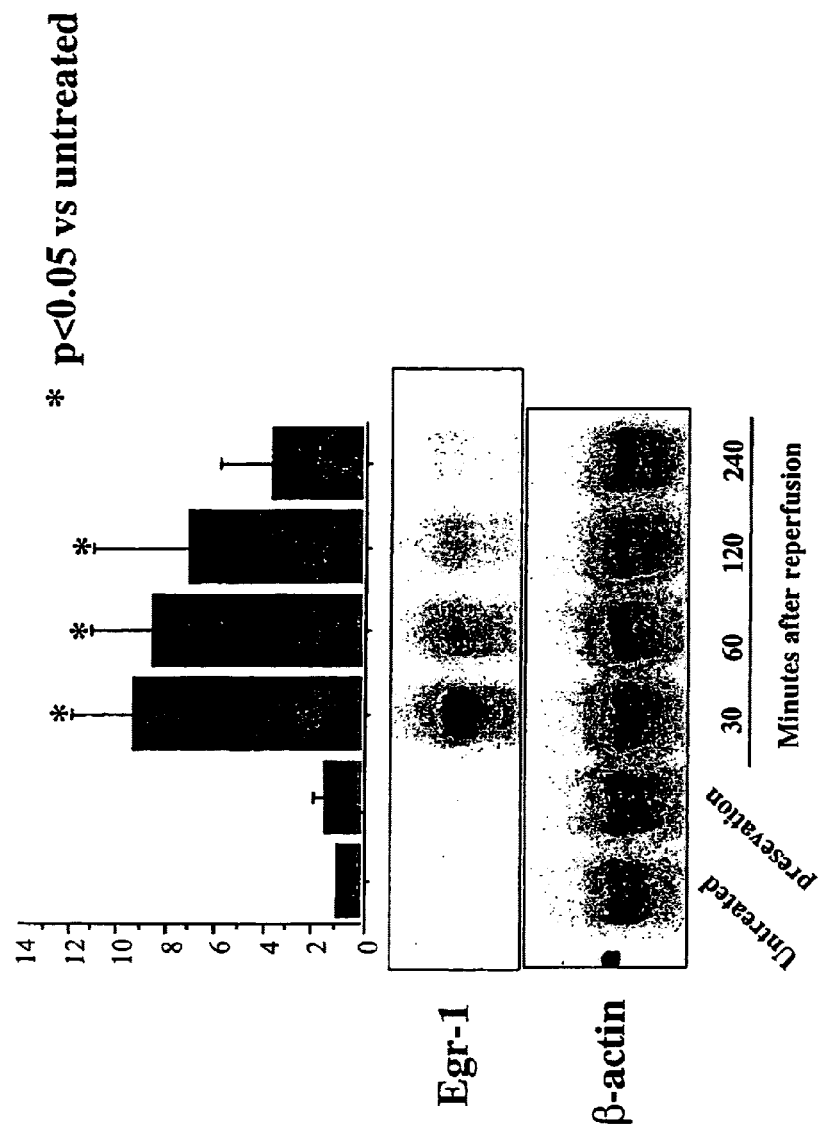

SEQUENCE LISTING

```
<160> NUMBER OF SEQ ID NOS: 6

<210> SEQ ID NO 1
<211> LENGTH: 15
<212> TYPE: DNA
<213> ORGANISM: Homo sapiens

<400> SEQUENCE: 1
cttggccgct gccat                                                      15

<210> SEQ ID NO 2
<211> LENGTH: 15
<212> TYPE: DNA
<213> ORGANISM: Homo sapiens

<400> SEQUENCE: 2
taccgtcgcc gtgct                                                      15

<210> SEQ ID NO 3
<211> LENGTH: 543
<212> TYPE: PRT
<213> ORGANISM: Homo sapiens

<400> SEQUENCE: 3

Met Ala Ala Ala Lys Ala Glu Met Gln Leu Met Ser Pro Leu Gln Ile
1               5                   10                  15

Ser Asp Pro Phe Gly Ser Phe Pro His Ser Pro Thr Met Asp Asn Tyr
                20                  25                  30

Pro Lys Leu Glu Glu Met Met Leu Leu Ser Asn Gly Ala Pro Gln Phe
            35                  40                  45

Leu Gly Ala Ala Gly Ala Pro Glu Gly Ser Gly Ser Asn Ser Ser Ser
        50                  55                  60

Ser Ser Ser Gly Gly Gly Gly Gly Gly Gly Gly Ser Asn Ser Ser
65                  70                  75                  80

Ser Ser Ser Ser Thr Phe Asn Pro Gln Ala Asp Thr Gly Glu Gln Pro
                85                  90                  95

Tyr Glu His Leu Thr Ala Glu Ser Phe Pro Asp Ile Ser Leu Asn Asn
            100                 105                 110

Glu Lys Val Leu Val Glu Thr Ser Tyr Pro Ser Gln Thr Thr Arg Leu
        115                 120                 125

Pro Pro Ile Thr Tyr Thr Gly Arg Phe Ser Leu Glu Pro Ala Pro Asn
    130                 135                 140

Ser Gly Asn Thr Leu Trp Pro Glu Pro Leu Phe Ser Leu Val Ser Gly
145                 150                 155                 160
```

```
        -continued

Leu Val Ser Met Thr Asn Pro Pro Ala Ser Ser Ser Ala Pro Ser
                165                 170                 175

Pro Ala Ala Ser Ser Ala Ser Ala Ser Gln Ser Pro Leu Ser Cys
            180                 185                 190

Ala Val Pro Ser Asn Asp Ser Ser Pro Ile Tyr Ser Ala Ala Pro Thr
        195                 200                 205

Phe Pro Thr Pro Asn Thr Asp Ile Phe Pro Glu Pro Gln Ser Gln Ala
210                 215                 220

Phe Pro Gly Ser Ala Gly Thr Ala Leu Gln Tyr Pro Pro Ala Tyr
225                 230                 235                 240

Pro Ala Ala Lys Gly Gly Phe Gln Val Pro Met Ile Pro Asp Tyr Leu
            245                 250                 255

Phe Pro Gln Gln Gln Gly Asp Leu Gly Leu Gly Thr Pro Asp Gln Lys
                260                 265                 270

Pro Phe Gln Gly Leu Glu Ser Arg Thr Gln Gln Pro Ser Leu Thr Pro
        275                 280                 285

Leu Ser Thr Ile Lys Ala Phe Ala Thr Gln Ser Gly Ser Gln Asp Leu
290                 295                 300

Lys Ala Leu Asn Thr Ser Tyr Gln Ser Gln Leu Ile Lys Pro Ser Arg
305                 310                 315                 320

Met Arg Lys Tyr Pro Asn Arg Pro Ser Lys Thr Pro Pro His Glu Arg
            325                 330                 335

Pro Tyr Ala Cys Pro Val Glu Ser Cys Asp Arg Arg Phe Ser Arg Ser
                340                 345                 350

Asp Glu Leu Thr Arg His Ile Arg Ile His Thr Gly Gln Lys Pro Phe
        355                 360                 365

Gln Cys Arg Ile Cys Met Arg Asn Phe Ser Arg Ser Asp His Leu Thr
370                 375                 380

Thr His Ile Arg Thr His Thr Gly Glu Lys Pro Phe Ala Cys Asp Ile
385                 390                 395                 400

Cys Gly Arg Lys Phe Ala Arg Ser Asp Glu Arg Lys Arg His Thr Lys
            405                 410                 415

Ile His Leu Arg Gln Lys Asp Lys Lys Ala Asp Lys Ser Val Val Ala
                420                 425                 430

Ser Ser Ala Thr Ser Ser Leu Ser Ser Tyr Pro Ser Pro Val Ala Thr
        435                 440                 445

Ser Tyr Pro Ser Pro Val Thr Thr Ser Tyr Pro Ser Pro Ala Thr Thr
450                 455                 460

Ser Tyr Pro Ser Pro Val Pro Thr Ser Phe Ser Ser Pro Gly Ser Ser
465                 470                 475                 480

Thr Tyr Pro Ser Pro Val His Ser Gly Phe Pro Ser Pro Ser Val Ala
            485                 490                 495

Thr Thr Tyr Ser Ser Val Pro Pro Ala Phe Pro Ala Gln Val Ser Ser
                500                 505                 510

Phe Pro Ser Ser Ala Val Thr Asn Ser Phe Ser Ala Ser Thr Gly Leu
        515                 520                 525

Ser Asp Met Thr Ala Thr Phe Ser Pro Arg Thr Ile Glu Ile Cys
530                 535                 540

<210> SEQ ID NO 4
<211> LENGTH: 6590
<212> TYPE: DNA
<213> ORGANISM: Homo sapiens

<400> SEQUENCE: 4
```

-continued

```
gcgggctggg gctgtggctc acacctggaa tcccagcact ttgggaggcc gaagtgggtg     60
aatcgcttga gctcaagagt tcaagaccag cctgggcaac acagcgaaac ccctctctac    120
gaaaatacaa aaaaaaaaaa aaaaaagtaa aagccaggcg tggtggcagg cacctgtagt    180
ccaagctact cgagaggagg aggctggagg atcacttgag cctgggaggc ggaggttgca    240
gtgagctcgc gccactgcac tccaacctgg gtgccagcgt gagacccgt ctcagaaaga    300
ataaaaacat taaaaaaaaa atttggctaa gtaccctac cagggagtgg caaaatggac     360
attcagacac aaggccatct cgctgcaac agcctggcct tcctgcccttt gcggcaggag    420
tcctctgaga ggcgcatcac tcctgcccca atggacaact ccgtagacag tgggagtgag    480
ccccccacct ccccagcgga cttgagacgg caggctccga gacgaggag tcctggttca    540
ttaagttggt ttttataaaa aaacatgttt ggaggggggga cagccacaaa gggattaagt   600
ccaagaaagt taccccctcc cccacctaat cccctgacc ccgacctcca gaggctgttg     660
gggtttacag aggccctcac ctcctccctt ccctctcggt gtcgtcaaac accctccttc    720
tccacatttc tctttctgct ttcttttaa atccagaaaa aacagtacct cctctggatt     780
cagagctaga gcaggaggag ccttccttcc cggaatccct gttcccttttg ggggagcaac   840
tgacggttcg tggggcggg gagggttccc cttttttgttt gacccaagga agactgggga   900
atatttcct tagacaccac ccacccctt ttctttttcc ccttcacttt gccaggctgg      960
ggttgaggat tgttatcccg gagtttgggc gcttcggaag tgacggttcc ccggggtttg   1020
aagggggagcc cgggttaagc gcctgttcag ttcgtgctca tgcgtcgaag gctcccccgg  1080
ccttgctccg cgcccagcgc cgcatccggg aggaggagcg aggaggcggc ggaagagccc   1140
gcgcggccgc agtccgggc tgggagtgga gagggaacct ccaggggca gcaccgagcc    1200
gcaaagccgg tcctctcttc gcgcccagcc cggggtcccc agatagccca tagggaagcc   1260
cctctttcgg attcccgcag tgtgggccgg ccctccacct ggactggata aagggggaa    1320
agtgaccct caccacaagg accattatct cctggtgaga acaagaatca ggcctctctt    1380
ggggcaatca gcttccccac ttcggtcccc caaaggtggg ctctttgccg gcggggacta   1440
gggaacagcc tttcggttcc ggggggagcac aggggacccc aggcaccagc agccccatcc  1500
caccgacagg tggcagaggc aaggcagctc actgctatac agtgtcccaa gaaccaagtg   1560
gccgtgactt cctatcctca atttcccagc gacacccgga aagacaccgt gccatagatc   1620
gaggcccggg gtcaaggccc cgcctctcct gggcggcccc tgcccaggcg ggcccagccg   1680
ctcctccccc gcactcccgg ttcgctctca cggtccctga ggtgggcggg cgggcctgga   1740
tgacagcgat agaaccccgg cccgactcgc cctcgccccc gctctgggtc tgggcttccc   1800
cagcctagtt cacgcctagg agccgcctga gcagccgcgc ccagcgccac acgccacgag   1860
ccctccccgc ctgggcgtcc ccggatcccg cgagcgctcg ggctcccggc ttggaaccag   1920
ggaggaggga gggagcgagg gagcaaccag ctcggaccgg aatgcatata gagcaggaag   1980
gatcccccgc cggaacaacc cttatttggg cagcacctta tttggagtgg cccgatatgg   2040
cccggcgctt ccggctctgg gaggagggaa gaaggcggag ggaggggcaa cgcgggaact   2100
ccggagctgc cggtcccgga ggccccggcg gcggctagag ctctaggctt ccccgaagct   2160
gggcgcctgg gatgcgggcc gggccgggcc ctagggtgca ggatggaggt gccgggcgct   2220
gtcggatggg gggcttcacg tcactccggg tcctcccccg gtcctgccat attagggctt   2280
ctgcttccca tatatgccat gtacgtcacg acggaggcgg accgtgccg ttccagaccc    2340
```

-continued

| | |
|---|---|
| ttcaaataga ggcggatccg gggagtcgcg agagatccag ccgcagaact tggggagccg | 2400 |
| ccgccgccat ccgccgccgc agccagcttc cgccgccgca ggaccggccc ctgccccagc | 2460 |
| ctccgcagcc gcggcgcgtc cacgcccgcc cgcgcccagg gcgagtcggg gtcgccgcct | 2520 |
| gcacgcttct cagtgttccc cgcgccccgc atgtaacccg gccaggcccc cgcaacggtg | 2580 |
| tccctgcag ctccagcccc gggctgcacc ccccgcccc gacaccagct ctccagcctg | 2640 |
| ctcgtccagg atggccgcgg ccaaggccga gatgcagctg atgtcccgc tgcagatctc | 2700 |
| tgacccgttc ggatccttc ctcactcgcc caccatggac aactaccta agctggagga | 2760 |
| gatgatgctg ctgagcaacg gggctcccca gttcctcggc ccgccgggg ccccagaggg | 2820 |
| cagcggcagc aacagcagca gcagcagcag cggggcggt ggaggcggcg ggggcggcag | 2880 |
| caacagcagc agcagcagca gcaccttcaa ccctcaggcg gacacgggcg agcagcccta | 2940 |
| cgagcacctg accgcaggta agcagtggcc tacgccgagg gggaacccctt cgccaccat | 3000 |
| cctggcgtcc tgtccttcac cgcaggagtg ctcctggatc ttagaatgag agcccgggttt | 3060 |
| cccttttcatt cctcgcatcc ccagagtcat gtgttagagg gatgccaagg aaccccacac | 3120 |
| agcccacccc ctgccctcat ccctagcgga gcgcagagga ccgagcttt gttttggatg | 3180 |
| gagagctctg gagctgcgtg ggtgggtgga gggggagggc ttgttttgat gagcggggct | 3240 |
| gcgcccccac ctccagtaag acttgccttg ccttgcttgc cgcctgtccc caaggaagga | 3300 |
| ccgtgatcct tggccgtgga tgtcccggca gcccgggttt ggggcgcgc actagccgcg | 3360 |
| gccatggggg tgctggcggg aatccctcgc ccgcacagcc gccgctgcgg agcgctgcga | 3420 |
| gctgcagtgg aggggattc tccgtatttg cgtcactgtt gttgaaatgg gctctgccac | 3480 |
| tggtgcgggt ccaggaacat tgcaatgtgc tgctatcaat tattaactac ctcgggagtc | 3540 |
| aatggtagcc ggcccggtct cttgcctggc agctcgggtc gtcctcgtcc tccagtgatt | 3600 |
| gttttccagt aaccaggcct cccgcttctc tctctcctgc cagagtcttt tcctgacatc | 3660 |
| tctctgaaca acgagaaggt gctggtggag accagttacc ccagccaaac cactcgactg | 3720 |
| cccccccatca cctatactgg ccgcttttc ctggagcctg cacccaacag tggcaacacc | 3780 |
| ttgtggcccg agcccctctt cagcttggtc agtggcctag tgagcatgac caacccaccg | 3840 |
| gcctcctcgt cctcagcacc atctccagcg gcctcctccg cctccgcctc ccagagccca | 3900 |
| cccctgagct gcgcagtgcc atccaacgac agcagtccca tttactcagc ggcacccacc | 3960 |
| ttccccacgc cgaacactga cattttccct gagccacaaa gccaggcctt ccgggctcg | 4020 |
| gcagggacag cgctccagta cccgcctcct gcctaccctg ccgccaaggg tggcttccag | 4080 |
| gttcccatga tccccgacta cctgtttcca cagcagcagg gggatctggg cctgggcacc | 4140 |
| ccagaccaga agcccttcca gggcctggag agccgcaccc agcagccttc gctaacccct | 4200 |
| ctgtctacta ttaaggcctt tgccactcag tcgggctccc aggacctgaa ggccctcaat | 4260 |
| accagctacc agtcccagct catcaaaccc agccgcatgc gcaagtatcc caaccggccc | 4320 |
| agcaagacgc ccccccacga acgcccttac gcttgcccag tggagtcctg tgatcgccgc | 4380 |
| ttctcccgct ccgacgagct cacccgccac atccgcatcc acacaggcca gaagcccttc | 4440 |
| cagtgccgca tctgcatgcg caacttcagc cgcagcgacc acctcaccac ccacatccgc | 4500 |
| acccacacag gcgaaaagcc cttcgcctgc gacatctgtg gaagaaagtt tgccaggagc | 4560 |
| gatgaacgca gaggcatac caagatccac ttgcggcaga aggacaagaa agcagacaaa | 4620 |
| agtgttgtgg cctcttcggc cacctcctct ctctcttcct acccgtcccc ggttgctacc | 4680 |
| tcttacccgt ccccggttac tacctcttat ccatccccgg ccaccacctc atacccatcc | 4740 |

-continued

```
cctgtgccca cctccttctc ctctcccggc tcctcgacct acccatcccc tgtgcacagt      4800
ggcttcccct cccgtcggt ggccaccacg tactcctctg ttcccctgc tttcccggcc        4860
caggtcagca gcttcccttc ctcagctgtc accaactcct tcagcgcctc cacagggctt      4920
tcggacatga cagcaacctt ttctcccagg acaattgaaa tttgctaaag ggaaggggga     4980
aagaaaggga aagggagaa aaagaaacac aagagactta aggacagga ggaggagatg       5040
gccataggag aggagggttc ctcttaggtc agatggaggt tctcagagcc aagtcctccc    5100
tctctactgg agtggaaggt ctattggcca acaatccttt ctgcccactt ccccttcccc     5160
aattactatt ccctttgact tcagctgcct gaaacagcca tgtccaagtt cttcacctct     5220
atccaaagaa cttgatttgc atggattttg gataaatcat ttcagtatca tctccatcat     5280
atgcctgacc ccttgctccc ttcaatgcta gaaaatcgag ttggcaaaat ggggtttggg    5340
cccctcagag ccctgccctg caccccttgta cagtgtctgt gccatggatt tcgtttttct    5400
tggggtactc ttgatgtgaa gataaatttgc atattctatt gtattatttg gagttaggtc    5460
ctcacttggg ggaaaaaaaa aaaaaaaagc caagcaaacc aatggtgatc ctctattttg     5520
tgatgatgct gtgacaataa gtttgaacct tttttttga aacagcagtc ccagtattct     5580
cagagcatgt gtcagagtgt tgttccgtta accttttttgt aaatactgct tgaccgtact    5640
ctcacatgtg gcaaatatg gtttggtttt tcttttttttt ttttgaaagt gtttttttctt   5700
cgtccttttg gtttaaaaag tttcacgtct tggtgccttt tgtgtgatgc cccttgctga    5760
tggcttgaca tgtgcaattg tgagggacat gctcacctct agccttaagg ggggcaggga   5820
gtgatgattt gggggaggct ttgggagcaa aataaggaag agggctgagc tgagcttcgg   5880
ttctccagaa tgtaagaaaa caaatctaa acaaaatct gaactctcaa aagtctattt     5940
ttttaactga aaatgtaaat ttataaatat attcaggagt tggaatgttg tagttaccta     6000
ctgagtaggc ggcgatttt gtatgttatg aacatgcagt tcattatttt gtggttctat     6060
tttactttgt acttgtgttt gcttaaacaa agtgactgtt tggcttataa acacattgaa    6120
tgcgctttat tgcccatggg atatgtggtg tatatccttc caaaaaatta aaacgaaaat    6180
aaagtagctg cgattgggta tgtgtttcct gggttagggg aaggactctg ccctattgag    6240
ggctgtgagg ttttctgaag acttggcctt tagagataca aggatcctcc agccagagtc    6300
aggcccactg tgtgaaactg gagttcgtta tttatgagga ctgagtatgg gtcttcaaat    6360
agggtctcgg tctatccacc caggctggag tgcagtagtg taatcacagt tcactgcagc   6420
tttggtgtct caggctcaag tgatcctccc acctcagcct cctgagtagc tgggactata    6480
ggcacgtgcc accacactcg gttaatgttt atagagacag ggttttgcca tgttgcccag   6540
gctggagttc ttcttgataa tgggcctgtt cctcttcagt ctgttgggtg               6590
```

<210> SEQ ID NO 5
<211> LENGTH: 543
<212> TYPE: PRT
<213> ORGANISM: Homo sapiens

<400> SEQUENCE: 5

```
Met Ala Ala Ala Lys Ala Glu Met Gln Leu Met Ser Pro Leu Gln Ile
 1               5                  10                  15

Ser Asp Pro Phe Gly Ser Phe Pro His Ser Pro Thr Met Asp Asn Tyr
            20                  25                  30

Pro Lys Leu Glu Glu Met Met Leu Leu Ser Asn Gly Ala Pro Gln Phe
        35                  40                  45
```

-continued

```
Leu Gly Ala Ala Gly Ala Pro Glu Gly Ser Gly Ser Asn Ser Ser Ser
     50                  55                  60

Ser Ser Ser Gly Gly Gly Gly Gly Gly Gly Ser Asn Ser Ser
65              70                  75                  80

Ser Ser Ser Ser Thr Phe Asn Pro Gln Ala Asp Thr Gly Glu Gln Pro
                 85                  90                  95

Tyr Glu His Leu Thr Ala Glu Ser Phe Pro Asp Ile Ser Leu Asn Asn
            100                 105                 110

Glu Lys Val Leu Val Glu Thr Ser Tyr Pro Ser Gln Thr Thr Arg Leu
            115                 120                 125

Pro Pro Ile Thr Tyr Thr Gly Arg Phe Ser Leu Glu Pro Ala Pro Asn
            130                 135                 140

Ser Gly Asn Thr Leu Trp Pro Glu Pro Leu Phe Ser Leu Val Ser Gly
145                 150                 155                 160

Leu Val Ser Met Thr Asn Pro Pro Ala Ser Ser Ser Ala Pro Ser
                165                 170                 175

Pro Ala Ala Ser Ser Ala Ser Ala Ser Gln Ser Pro Pro Leu Ser Cys
                180                 185                 190

Ala Val Pro Ser Asn Asp Ser Ser Pro Ile Tyr Ser Ala Ala Pro Thr
            195                 200                 205

Phe Pro Thr Pro Asn Thr Asp Ile Phe Pro Glu Pro Gln Ser Gln Ala
    210                 215                 220

Phe Pro Gly Ser Ala Gly Thr Ala Leu Gln Tyr Pro Pro Pro Ala Tyr
225                 230                 235                 240

Pro Ala Ala Lys Gly Gly Phe Gln Val Pro Met Ile Pro Asp Tyr Leu
                245                 250                 255

Phe Pro Gln Gln Gln Gly Asp Leu Gly Leu Gly Thr Pro Asp Gln Lys
                260                 265                 270

Pro Phe Gln Gly Leu Glu Ser Arg Thr Gln Gln Pro Ser Leu Thr Pro
            275                 280                 285

Leu Ser Thr Ile Lys Ala Phe Ala Thr Gln Ser Gly Ser Gln Asp Leu
290                 295                 300

Lys Ala Leu Asn Thr Ser Tyr Gln Ser Gln Leu Ile Lys Pro Ser Arg
305                 310                 315                 320

Met Arg Lys Tyr Pro Asn Arg Pro Ser Lys Thr Pro Pro His Glu Arg
                325                 330                 335

Pro Tyr Ala Cys Pro Val Glu Ser Cys Asp Arg Arg Phe Ser Arg Ser
            340                 345                 350

Asp Glu Leu Thr Arg His Ile Arg Ile His Thr Gly Gln Lys Pro Phe
            355                 360                 365

Gln Cys Arg Ile Cys Met Arg Asn Phe Ser Arg Ser Asp His Leu Thr
    370                 375                 380

Thr His Ile Arg Thr His Thr Gly Glu Lys Pro Phe Ala Cys Asp Ile
385                 390                 395                 400

Cys Gly Arg Lys Phe Ala Arg Ser Asp Glu Arg Lys Arg His Thr Lys
                405                 410                 415

Ile His Leu Arg Gln Lys Asp Lys Lys Ala Asp Lys Ser Val Val Ala
            420                 425                 430

Ser Ser Ala Thr Ser Ser Leu Ser Ser Tyr Pro Ser Pro Val Ala Thr
            435                 440                 445

Ser Tyr Pro Ser Pro Val Thr Thr Ser Tyr Pro Ser Pro Ala Thr Thr
450                 455                 460
```

| | | | | | | | | | | | | | | |
|---|---|---|---|---|---|---|---|---|---|---|---|---|---|---|
|Ser|Tyr|Pro|Ser|Pro|Val|Pro|Thr|Ser|Phe|Ser|Pro|Gly|Ser|Ser|
|465| | | |470| | | |475| | | |480| | |
|Thr|Tyr|Pro|Ser|Pro|Val|His|Ser|Gly|Phe|Pro|Ser|Pro|Ser|Val|Ala|
| | | | |485| | | |490| | | |495| |
|Thr|Thr|Tyr|Ser|Ser|Val|Pro|Pro|Ala|Phe|Pro|Ala|Gln|Val|Ser|Ser|
| | | |500| | | |505| | | |510| | |
|Phe|Pro|Ser|Ser|Ala|Val|Thr|Asn|Ser|Phe|Ser|Ala|Ser|Thr|Gly|Leu|
| | |515| | | |520| | | |525| | | |
|Ser|Asp|Met|Thr|Ala|Thr|Phe|Ser|Pro|Arg|Thr|Ile|Glu|Ile|Cys|
| |530| | | |535| | | |540| | | | | |

<210> SEQ ID NO 6
<211> LENGTH: 3132
<212> TYPE: DNA
<213> ORGANISM: Homo sapiens

<400> SEQUENCE: 6

```
ccgcagaact tggggagccg ccgccgccat ccgccgccgc agccagcttc cgccgccgca    60
ggaccggccc ctgccccagc ctccgcagcc gcggcgcgtc cacgcccgcc cgcgcccagg   120
gcgagtcggg gtcgccgcct gcacgcttct cagtgttccc cgcgccccgc atgtaacccg   180
gccaggcccc cgcaacggtg tcccctgcag ctccagcccc gggctgcacc ccccgcccc   240
gacaccagct ctccagcctg ctcgtccagg atggccgcgg ccaaggccga gatgcagctg   300
atgtccccgc tgcagatctc tgacccgttc ggatcctttc ctcactcgcc caccatggac   360
aactacccta agctggagga gatgatgctg ctgagcaacg ggctccccca gttcctcggc   420
gccgccgggg ccccagaggg cagcggcagc aacagcagca gcagcagcag cgggggcggt   480
ggaggcggcg ggggcggcag caacagcagc agcagcagca gcaccttcaa ccctcaggcg   540
gacacgggcg agcagcccta cgagcacctg accgcagagt cttttcctga catctctctg   600
aacaacgaga aggtgctggt ggagaccagt taccccagcc aaaccactcg actgccccc   660
atcacctata ctggccgctt tcccctggag cctgcaccca acagtggcaa caccttgtgg   720
cccgagcccc tcttcagctt ggtcagtggc ctagtgagca tgaccaaccc accggcctcc   780
tcgtcctcag caccatctcc agcggcctcc tccgcctccg cctcccagag cccaccccctg   840
agctgcgcag tgccatccaa cgacagcagt cccatttact cagcggcacc caccttcccc   900
acgccgaaca ctgacatttt ccctgagcca aaagccagg ccttcccggg ctcggcaggg   960
acagcgctcc agtacccgcc tcctgcctac cctgccgcca agggtggctt ccaggttccc  1020
atgatccccg actacctgtt tccacagcag caggggatc tgggcctggg caccccagac  1080
cagaagccct tccagggcct ggagagccgc acccagcagc cttcgctaac ccctctgtct  1140
actattaagg cctttgccac tcagtcgggc tcccaggacc tgaaggccct caataccagc  1200
taccagtccc agctcatcaa acccagccgc atgcgcaagt atcccaaccg gccagcaag  1260
acgcccccc acgaacgccc ttacgcttgc ccagtggagt cctgtgatcg ccgcttctcc  1320
cgctccgacg agctcacccg ccacatccgc atccacacag gccagaagcc cttccagtgc  1380
cgcatctgca tgcgcaactt cagccgcagc gaccacctca ccacccacat ccgcacccac  1440
acaggcgaaa agcccttcgc ctgcgacatc tgtggaagaa agtttgccag gagcgatgaa  1500
cgcaagaggc ataccaagat ccacttgcgg cagaaggaca agaaagcaga caaaagtgtt  1560
gtggcctctt cggccacctc ctctctctct tcctacccgt cccggttgc tacctcttac  1620
ccgtcccccgg ttactacctc ttatccatcc ccggccacca cctcataccc atcccctgtg  1680
```

-continued

```
cccacctcct tctcctctcc cggctcctcg acctacccat ccectgtgca cagtggcttc    1740 ccctccccgt cggtggccac cacgtactcc tctgttcccc ctgctttccc ggcccaggtc    1800
agcagcttcc cttcctcagc tgtcaccaac tccttcagcg cctccacagg gctttcggac    1860
atgacagcaa cctttctctcc caggacaatt gaaatttgct aaaggggaaag gggaaagaaa    1920 gggaaaaggg agaaaaagaa acacaagaga cttaaaggac aggaggagga gatggccata    1980
ggagaggagg gttcctctta ggtcagatgg aggttctcag agccaagtcc tccctctcta    2040
ctggagtgga aggtctattg gccaacaatc ctttctgccc acttcccctt ccccaattac    2100
tattcccttt gacttcagct gcctgaaaca gccatgtcca agttcttcac ctctatccaa    2160
agaacttgat ttgcatggat tttggataaa tcatttcagt atcatctcca tcatatgcct    2220
gaccccttgc tcccttcaat gctagaaaat cgagttggca aaatgggggtt tgggcccctc    2280 agagccctgc cctgcaccct tgtacagtgt ctgtgccatg gatttcgttt ttcttggggt    2340
actcttgatg tgaagataat ttgcatattc tattgtatta tttggagtta ggtcctcact    2400
tgggggaaaa aaaaaaaaaa aagccaagca aaccaatggt gatcctctat tttgtgatga    2460
tgctgtgaca ataagtttga acctttttttt ttgaaacagc agtcccagta ttctcagagc    2520
atgtgtcaga gtgttgttcc gttaaccttt ttgtaaatac tgcttgaccg tactctcaca    2580
tgtggcaaaa tatggtttgg tttttctttt tttttttga aagtgttttt tcttcgtcct    2640
tttggtttaa aaagtttcac gtcttggtgc cttttgtgtg atgccccttg ctgatggctt    2700
gacatgtgca attgtgaggg acatgctcac ctctagcctt aagggggggca gggagtgatg    2760 atttgggggga ggctttggga gcaaaataag gaagagggct gagctgagct tcggttctcc    2820
agaatgtaag aaaacaaaat ctaaaacaaa atctgaactc tcaaaagtct attttttaa    2880 ctgaaaatgt aaatttataa atatattcag gagttggaat gttgtagtta cctactgagt    2940
aggcggcgat ttttgtatgt tatgaacatg cagttcatta ttttgtggtt ctattttact    3000
ttgtacttgt gtttgcttaa acaaagtgac tgtttggctt ataaacacat tgaatgcgct    3060
ttattgccca tgggatatgt ggtgtatatc cttccaaaaa attaaaacga aaataaagta    3120
gctgcgattg gg                                                        3132
```

METHODS FOR SUPPRESSING EARLY GROWTH RESPONSE— 1PROTEIN (EGR-1) TO REDUCE VASCULAR INJURY IN A SUBJECT

The invention disclosed herein was made with Government support under Grant No. HL 42507 from the National Institutes of Health of the U.S. Department of Health and Human Services. Accordingly, the U.S. Government has certain rights in this invention.

BACKGROUND OF THE INVENTION

Throughout this application, various publications are referenced by author and date within the text. Full citations for these publications may be found listed alphabetically at the end of the specification immediately preceding the claims. All patents, patent applications and publications cited herein, whether supra or infra, are hereby incorporated by reference in their entirety. The disclosures of these publications in their entireties are hereby incorporated by reference into this application in order to more fully describe the state of the art as known to those skilled therein as of the date of the invention described and claimed herein.

It has long been hypothesized that ischemia primes mechanisms leading to reperfusion injury and sets the stage for an exaggerated, maladaptive vascular response eventuating in tissue damage. Hypoxemia, a central component of the ischemic vascular milieu, has been defined as a key factor initiating vascular injury. To date, the cellular response to oxygen deprivation has largely been defined by studies of the transcription factor HIF (Hypoxia-Inducible Factor)-1. Activation of HIF-1 by hypoxia/hypoxemia facilitates metabolic adaptation to environmental challenge; glucose uptake by the noninsulin-dependent glucose transporter (GLUT1) is enhanced, and expression of glycolytic enzymes, erythropoietin and Vascular Endothelial Growth Factor (VEGF) is amplified. However, another facet of the cellular response to hypoxia has been revealed by the deposition of fibrin in lung vasculature consequent to induction of procoagulant tissue factor.

SUMMARY OF THE INVENTION

The invention provides a method for reducing damage to an ischemic tissue which comprises contacting cells of the tissue with an inhibitor of Early Growth Response Factor-1 Protein (Egr-1). In addition, the invention provides a method for reducing vascular injury during reperfusion of an ischemic tissue in a subject which comprises contacting the tissue with a compound which inhibits expression of Early Growth Response Factor-1 (Egr-1) protein in the tissue so as to reduce vascular injury in the tissue during reperfusion. wherein the inhibitor is a nucleic acid consisting essentially of the polynucleotide sequence 5'-CTTGGCCGCTGCCAT-3' (SEQ ID NO:1). In one embodiment of the invention, the subject has suffered a stroke, or a myocardial infarction. In another embodiment of the invention, the subject is undergoing or has undergone angioplasty, cardiac surgery, vascular surgery, or organ transplantation.

BRIEF DESCRIPTION OF THE FIGURES

FIGS. 1A, 1B1–B4, 1C1–C4, 1D, 1E1–E4, 1F1–F4. Ischemia/reperfiision induces tissue factor and PAI-1: effect of Egr-1. Mice underwent left lung I/R or no instrumentation (C=control), and lungs were harvested for Northern blotting (FIGS. 1A, 1D), in situ hybridization (FIGS. 1B1–B4, 1E1–E4), and immunohistocheniical analysis (1C1–C4, 1F1–F4). FIGS. 1A, 1B1–B4, 1C1–C4 Tissue factor. Total RNA was prepared from lung subjected to I/R and Northern blotting was performed (10 μg/lane) with $^{32}$p-labelled cDNA probes for tissue factor (TF) and β-actin (FIG. 1A; upper panel). In the lower panel, densitometric analysis of three autoradiograms from three different experiments is shown, below the representative autoradiogram displayed in the upper panel. The intensity of the tissue factor mRNA band was normalized according to the intensity of the β-actin band in that lane. Other assays involving autoradiograms were similarly analyzed in the figures below. In situ hybridization (ISH) was performed with a digoxigenin-labelled riboprobe for tissue factor (FIGS. 1B1–B4) with tissue from wild-type mice: control lung (FIG. 1B-1) or I/R lung (FIG. 1B-2, 3). FIG. 1B-4 shows F4/80 staining of a section adjacent to that shown in FIG. 1B-3. Arrows denote cells in which TF mRNA and F4/80 immunoreactivity were colocalized (this same format is employed for all ISH figures below). FIGS. 1C1–C4. Immunostaining was performed with anti-tissue factor IgG using tissue from wild-type mice, control(FIG. 1C-1) or I/R lung (FIG. 1C-2), or Egr-1 null mice, control (FIG. 1C-3) or I/R lung (FIG. 1C-4). D–F. PAI-1. Northern blotting (FIG. 1D), ISH (FIGS. 1E1–E4) and immunostaining (FIGS. 1F1–1F4) were performed to detect PAI-1 transcripts (FIG. 1D, FIG. 1E1–E3; E4 shows F4/80 staining of a section adjacent to that in E-3) and antigen (FIG. 1F1–F4). The origin of samples is the same as in A–C. * indicates p<0.01 in panels FIGS. 1A, 1D. The bar in panels FIGS. 1B–1C and FIGS. 1E, 1F indicates: 5 μm (FIG. 1B-1, 2; 1C1-4; 1E-1, 2; 1F1-4), and 2 μm (1B-3, 4; 1E-3, 4). Results of representative experiments with=5 mice in each group are shown, and experiments were repeated three times. Beside each micrograph mouse genotype, with respect to Egr-1 (+/+, wild-type and Egr-1 null), is indicated along with the experimental condition (control [C]= uninstrumented; I/R=ischemia/reperfusion).

FIGS. 2A, 2B1–2B4, 2C1–2C4. Ischemia/reperfusion induces VEGF.: effect of Egr-1- Mice underwent left lung I/R or no instrumentation (C=control), and lung was harvested for Northern blotting (FIG. 2A), ISH (FIGS. 2B1–2B4), and immunohistochemistry [FIGS. 2C1–2C4] for VEGF. Northern blotting was performed on total RNA from control or I/R lung (10 μg/lane) with 32P-labelled CDNA probes for VEGF and β-actin (FIG. 2A). * indicates p<0.01. ISH was performed with a digoxigenin-labelled riboprobe for VEGF (FIG. 2B1–2B4) with tissue from wild-type mice: control lung (FIG. 2B-1) or I/R lung (FIG. 2B-2, 3). FIG. 2B-4 shows F4/80 staining of a section adjacent to that shown in FIG. 2B-3. Immunostaining was performed with anti-VEGF IgG using tissue from wild-type mice, control (FIG. 2C-1) or I/R lung (FIG. 2C-2), or from Egr-1 null mice, control (FIG. 2C-3) or I/R lung (FIG 2C-4). The bar indicates 5 μm (FIG. 2B-1, 2; FIG. 2C1-4) and 2 Am (FIG. 2B-3, 4). Results of representative experiments with=5 mice in each group are shown, and each experiment was repeated three times.

FIGS. 3A, 3B1–B4, 3C1–C4. Ischemia/reperfusion induces ICAM-1: effect of Egr-1. Mice underwent left lung I/R or no instrumentation (C=control), and lungs were harvested for Northern blotting (A), ISH (B) and immunohistochemistry (C) for ICAM-1. Northen blotting was performed on total RNA from control or I/R lung (10 μg/lane) with 32P-labelled cDNA probes for ICAM-1 and β-actin (A). * indicates p<0.01. ISH was performed with a digoxigenin-labelled riboprobe for ICAM-1 and tissue from wild-type mice: control lung (B-1) or I/R lung (B-2, 3). B-4 shows F4/80 staining of a section adjacent to that shown in B-3. Immunostaining was performed with anti-ICAM-1 IgG using tissue from wild-type mice, control (C-1) or I/R lung(C-2), or Egr-1 null mice, control (C-3) or I/R lung (C-4). The bar indicates 5 μm (B-1, 2; CI-4) and 2 μm (B-3, 4). Results of representative experiments with=5 mice in each group are shown, and each experiment was repeated three times.

FIGS. 4A, 4B1–B4, 4C, 4D, 4E1–E4, 4F, 4G, 4H1–4H4, 4I, 4J, 4K and 4L. Ischemia/reperfusion induces IL-1β and chemokines: effect of Egr-1. A–C. Expression of IL-1β. Mice underwent left lung I/R or no instrumentation (C=control), and lungs were harvested for Northern blotting (A), ISH (B) and ELISA [C] for IL-1β. Northern blotting was performed on total RNA from control or L/R lung (10 μg/lane) with 32P-labelled cDNA probes for EL-IB and B-actin (A). ISH was performed with a digoxigenin-labelled riboprobe for IL-1β (B) with tissue from wild-type mice: control lung (B-1) or I/R lung (B-2, 3). B-4 shows F4/80 staining of a section adjacent to that shown in B-3. In C, ELISA for IL-IB was performed on sera harvested after the 3 hr reperfusion period from wild-type or Egr-1 null mice subjected to I/R or from uninstrumented (C=control) mice. D–F. Expression of MIP-2 was determined by Northern analysis (D), ISH (E) and ELISA (F) as described for IL-1β except that MIP-2 cDNA/riboprobe and a MIP-2 ELISA were used. G-1. Expression of JE/MCP-1 was determined by Northern analysis (G), ISH (H) and ELISA (1) as described for IL-Iβ except that JE/MCP-1 cDNA/riboprobe and a JE/MCP-1 ELISA were used. .1-K. Expression of IP-10 and RANTES mRNA. Northern analysis was performed on total RNA from control or I/R lung (10 μg/lane) with 32P-labelled CDNA probes for IP-10 (J), RANTES (K) and B-actin (J,K). L. Expression of LTβ, MIF, and L32 mRNA. Ribonuclease protection assays were performed on RNA from control or I/R lung of wild-type or Egr-1 null mice to detect LTB, MIF or L32. The bar indicates 5 μm (panels 1–2 in B,E,H) and 2 μm (panels 3–4 in B,E,H). Results of representative experiments with =5 mice in each group are shown, and experiments were repeated three times. Beside each micrograph mouse genotype, with respect to Egr-1 (+/+, wild-type and −/−, Egr-1 null), is indicated along with the experimental condition (C [control]=uninstumented; I/R=ischemia/ reperfusion). indicates p<0.01.

FIGS. 5A, 5B1–5B4, 5C, 5D, 5E1–5E2, 5F, 5G and 5H. Ischemia/reperfusion induces and activates Egr-1 in murine lung. Wild-type mice underwent left lung ischemia for the indicated time or the full protocol of I/R, or no instrumentation (control), and lungs were harvested. Northern blotting was performed on total RNA from control or I/R lung (10 μg/lane) with 32P-labelled cDNA probes for Egr-1 and B-actin (A). ISH was performed with a digoxigenin-labelled riboprobe for Egr-1 (B) using tissue from wild-type mice: control (B-1) or LIR lung (B-2, 3). B-4 shows F4/80 staining of a section adjacent to that shown in B-3. C. Inununoblotting was performed using nuclear extracts from control or I/R lung of wild type mice (10 Ag protein/lane) with anti-Egr-I IgG (lanes 1–5) or anti-Spl IgG (lanes 6–10). Migration of simultaneously run molecular weight standards is shown on the far left of each gel. In D, analysis of data similar to that displayed in C (3 representative experiments) is shown. E. Immunostaining was performed with anti-Egr-1 IgG using tissue from wild-type mice, control lung (E-1) or I/R lung (E-2). F. EMSA was performed using 32P-labelled Egr probe and nuclear extract (NE; 10 jig protein/lane) from wild-type mice, either control or I/R lung. Where indicated, 100-fold excess unlabelled (cold) Egr or Sp 1 probe was added to nuclear extracts, or anti-Egr-1 IgG or nonimmune IgG (2 μg/ml in each case) was added to extracts from I/R lung. Lanes indicate: 1, free probe; 2, nuclear extract from uninstrumented (control) mice; 3–5, nuclear extracts from lung subjected to 15, 30 and 60 min of ischemia; 6, nuclear extract from lung subject to I/R; 78, nuclear extracts identical to those in 5 (60 min ischemia) and 6 (I/R), respectively, incubated with anti-Egr-1 IgG (aEgr-1); 9–10, nuclear extracts as in 5–6, respectively, but excess unlabelled (cold) Spl probe added during the incubation period; 11–12, nuclear extracts identical to those in 5–6, respectively, with excess unlabelled (cold) Egr probe; and, 13–14, same as 7–8, but noninimune (NI) IgG was used in place of anti-Egr-1 IgG. G. EMSA with 32P-labelled Sp I probe and the indicated nuclear extracts. In H, analysis of data similar to that shown in panels F–G (three representative experiments) is shown. The bar indicates 5 μm (B-1, 2; D-1, 2) and 2 μm (B-3, 4). *p<0.01 and **p<0.05.

FIGS. 6A, 6B, 6C, 6D, and 6E. Murine model of lung ischemia/reperfusion: effect of Egr-1. Mice were subjected to the left lung I (ischemia; 1 hr)/R (reperfusion; 3 hr) protocol as described in the text, blood flow to the uninstrumented right lung was blocked, and mortality was determined after 30 min with only the left lung in the circulation (A). In other experiments, arterial oxygenation was determined after I/R and the 30 min observation period (B). In panel C, after the indicated period of ischemia or I/R, animals received systemic heparin and the ischemic lung was processed for detection of fibrin by immunoblotting. In panels D–E, after I/R, myeloperoxidase activity (D) and the ratio of wet/dry lung weight (E) in the ischemic lung were determined. In B–E, N=5 for each group. +/+ refers to wild-type genotype for Egr-1 and −/− refers to homozygous Egr-1 null mice. Results of representative experiments are shown, and each experiment was repeated three times.

FIGS. 7A, 7B. Hypoxia induces Egr-1-dependent expression of mRNA for IL-1β, MIP-2, and JE/MCP-1, whereas expression of transcripts for LTβ, MIF, IL-7 and L32 remain unchanged. Mice were exposed to hypoxia (H) or the ambient atmosphere (N=normoxia), and total RNA was isolated from the lung and subjected to ribonuclease protection assay to detect transcripts for EL-1β, IL-7, MIP-2, JE/MCP-1. MIF, LTβ and L32. Results of representative experiments with =5 mice in each group are shown, and each experiment was repeated three times. *p<0.01.

FIG. 8. Northern Blotting; Egr-1/b-actin. Northern blotting of Egr-1 in untreated rat lung tissue, preserved but not transplanted lung tissue, and lung tissue following preservation/transplantation and reperfusion. Data are normalized to beta actin for control.

DETAILED DESCRIPTION OF THE INVENTION

Figure 9:
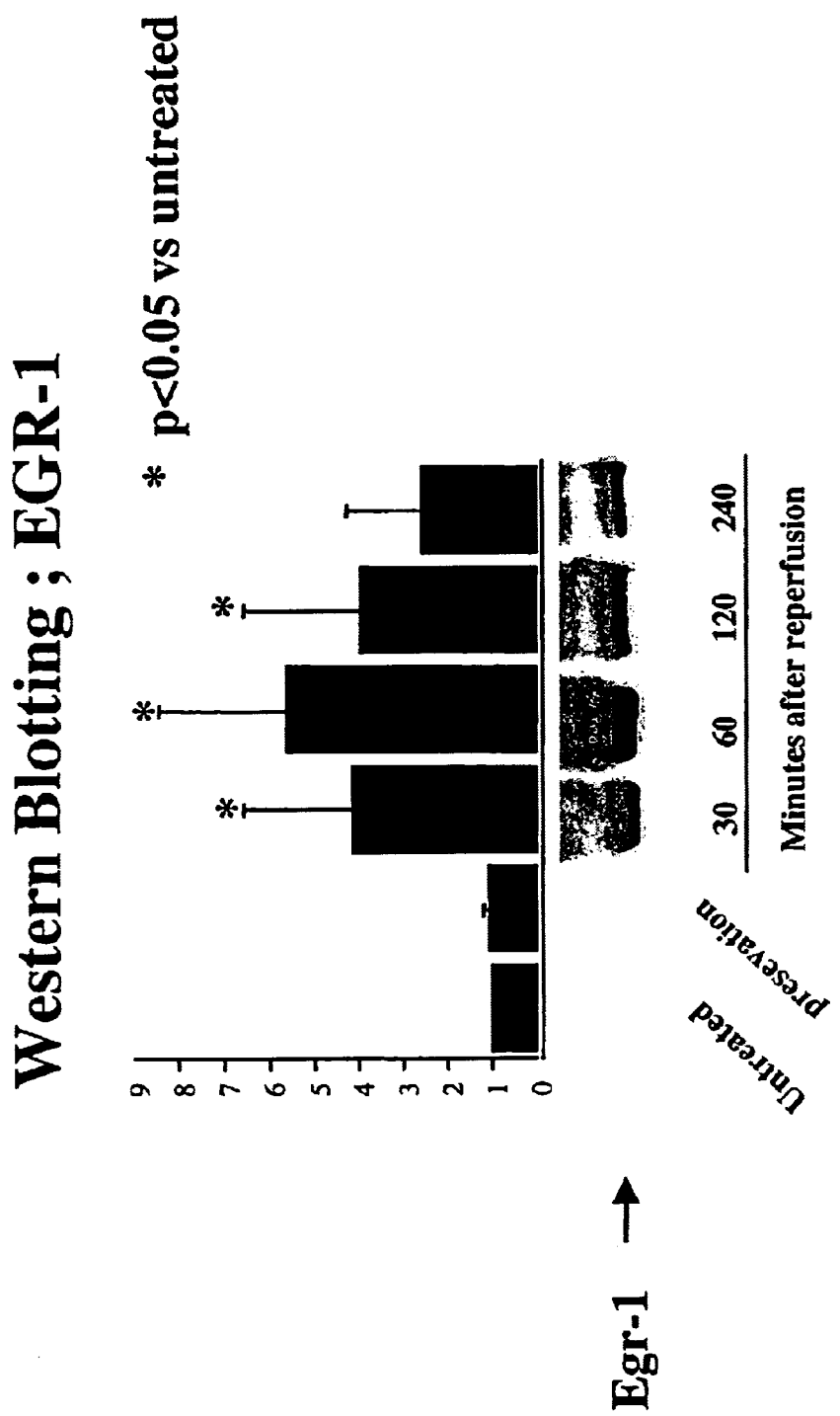
FIG. 9. Western Blotting; EGR-1. Western blotting of Egr-1 in untreated rat lung tissue, preserved but not transplanted lung tissue, and lung tissue following preservation/transplantation and reperfusion.

The present invention provides a method for reducing damage to an ischemic tissue which comprises contacting cells of the tissue with an inhibitor of Early Growth Response Factor-1 Protein (Egr-1).

In one embodiment of the invention, the inhibitor is an organic molecule having a molecular weight from about 500 daltons to about 50 kilodaltons. In another embodiment, the inhibitor is a nucleic acid. In another embodiment of the invention, the inhibitor is a compound which inhibits activity of Early Growth Response Factor-1 Protein (Egr-1) conjugated to a carrier.

In one embodiment of the invention, the inhibitor is a compound which inhibits expression of the Early Growth Response Factor-1 Protein (Egr-1) in the cells of the tissue. In another embodiment, the inhibitor is a nucleic acid molecule which comprises a polynucleotide sequence complementary to the polynucleotide sequence of Early Growth Response Factor-1 MRNA.

In another embodiment of the invention, the inhibitor is a peptide, a peptidomimetic compound, a nucleic acid molecule, a small molecule, an organic compound, an inorganic compound, or an antibody or a fragment thereof. In another embodiment of the invention, the carrier is a pharmaceutically acceptable carrier.

In another embodiment of the invention, the tissue is vascular tissue. In another embodiment of the invention, the tissue is a lung, a heart, a kidney, a vein, an artery, a stomach, a colon, a liver, skin, an eye, a pancreas, a finger, a brain, a toe or a limb. In another embodiment of the invention, the contacting of the cells with the inhibitor occurs in vitro. In another embodiment of the invention, the ischemic tissue is to be transplanted into a subject. In another embodiment of the invention, the tissue has been subjected to reduced or interrupted blood flow. In another embodiment of the invention, the damage to the ischemic tissue comprises cell death, abnormal cell function, abnormal cell growth, or inability for cell to maintain normal function. In another embodiment of the invention, the inhibitor is a nucleic acid consisting essentially of the polynucleotide sequence 5'-CTTGGCCGCTGCCAT-3' (SEQ ID NO:1).

The present invention also provides for a method for reducing vascular injury during reperfusion of an ischemic tissue in a subject which comprises contacting the tissue with a compound which inhibits expression of Early Growth Response Factor-1 (Egr-1) protein in the tissue so as to reduce vascular injury in the tissue during reperfusion.

In one embodiment of the invention, the tissue is an ischemic tissue. In another embodiment of the invention, the tissue is an organ which is to be transplanted into the subject. In another embodiment of the invention, the tissue is a lung, a heart, a kidney, a vein, an artery, a stomach, a colon, a liver, skin, an eye, a pancreas, a brain, a finger, a toe or a limb. In another embodiment of the invention, the compound is a nucleic acid which comprises a polynucleotide sequence complementary to the polynucleotide sequence of Early Growth Response Factor-1 MRNA.

In another embodiment of the invention, the compound is a peptide, a peptidomimetic compound, a nucleic acid molecule, a small molecule, an organic compound, an inorganic compound, or an antibody or a fragment thereof. In another embodiment of the invention, the subject has suffered a stroke, or a myocardial infarction. In another embodiment of the invention, the subject is undergoing angioplasty, cardiac surgery, vascular surgery, or organ transplantation. In another embodiment of the invention, the vascular surgery is coronary artery surgery. In another embodiment of the invention, the vascular injury comprises cell death, abnormal cell function, abnormal cell growth, or inability for cell to maintain normal function.

In another embodiment of the invention, the inhibitor is a nucleic acid consisting essentially of the polynucleotide sequence 5'-CTTGGCCGCTGCCAT-3' (SEQ ID NO:1). In another embodiment of the invention, the inhibitor is contacted with the tissue before, during or after reperfusion of the ischemic tissue.

In one embodiment of the present invention, the tissue is from a subject which is suffering from an ischemic disorder. In another embodiment of the invention, the ischemic disorder comprises a peripheral vascular disorder, a pulmonary embolus, a venous thrombosis, a myocardial infarction, a transient ischemic attack, unstable angina, a reversible ischemic neurological deficit, sickle cell anemia or a stroke disorder.

In another embodiment, the ischemic disorder is iatogenically induced. In another embodiment, the subject is undergoing angioplasty, heart surgery, lung surgery, spinal surgery, brain surgery, vascular surgery, abdominal surgery, or organ transplantation surgery. In another embodiment, the organ transplantation surgery comprises heart, lung, pancreas or liver transplantation surgery.

In one embodiment of the invention, the inhibitor is administered to the subject, or contacted with the tissue over a period of time in order to inhibit the activity of Egr-1 protein in the cells of the tissue.

In another embodiment, the period of time comprises from about 5 days before surgery or onset of the disorder to about 5 days after surgery or the onset of the disorder. In another embodiment, the period of time comprises from about 1 hour before surgery or the onset of the disorder to about 12 hours after surgery or the onset of the disorder. In another embodiment, the period of time comprises from about 12 hours before surgery or the onset of the disorder to about 1 hour after surgery or the onset of the disorder. In another embodiment, the period of time comprises from about 1 hour before surgery or the onset of the disorder to about 1 hour after surgery or the onset of the disorder.

As used herein, the "ischemic disorder" encompasses and is not limited to a peripheral vascular disorder, a venous thrombosis, a pulmonary embolus, a myocardial infarction, a transient ischemic attack, lung ischemia, unstable angina, a reversible ischemic neurological deficit, adjunct thromolytic activity, excessive clotting conditions, reperfusion injury, sickle cell anemia, a stroke disorder or an iatrogenically induced ischemic period such as angioplasty.

In one embodiment of the present invention, the subject is undergoing heart surgery,. angioplasty, lung surgery, spinal surgery, brain surgery, vascular surgery, abdominal surgery, or organ transplantation surgery. The organ transplantation surgery may include heart, lung, pancreas or liver transplantation surgery.

The tissue referred to herein is made up of cells. The cell may be a eukaryotic cell. The cell may be a cell of a subject. The subject may be a human. The cell may be a neuronal cell, an endothelial cell, a glial cell, a microglial cell, a smooth muscle cell, a somatic cell, a bone marrow cell, a liver cell, an intestinal cell, a germ cell, a myocyte, a mononuclear phagocyte, an endothelial cell, a tumor cell, a lymphocyte cell, a mesangial cell, a retinal epithelial cell, a retinal vascular cell a ganglion cell or a stem cell. The cell may also be other kinds of cells not explicitly listed herein. The cell may be any human cell. The cell may be a normal cell, an activated cell, a neoplastic cell, a diseased cell or an infected cell.

In one embodiment, the inhibitor comprises a peptide, a peptidomimetic compound, a nucleic acid molecule, a small molecule, an organic compound, an inorganic compound, or an antibody or a fragment thereof. The inhibitor may be an isolated peptide having an amino acid sequence which is a fragment of the complete Egr-1 amino acid sequence and so that the fragment works as a competitive inhibitor of the naturally occuring Egr-1 protein. The inhibitor may be any of the compounds or compositions described herein.

The inhibitor may be an antisense nucleic acid molecule which has a sequence which is the complement of the mRNA sequence of Egr-1. The inhibitor may be an antisense nucleic acid which is of a length from about 9 nucleotides long (i.e., a polynucleotide consisting of 9 bases) to about 35 nucleotides (i.e. a polynucleotide consisting of 35 bases) long. The nucleic acid could also be of a much longer length. The length of an antisense nucleic acid molecule is generally shorter than an average coding sequence. If, however, the inhibitor is a nucleic acid which does not work as an antisense molecule, than the length, of course, would be much longer.

The inhibitor could also be a chimeric nucleic acid which comprises at least a portion of the Egr-1 coding sequence linked in frame to a nucleic acid which encodes a targeting protein (i.e., a protein which can specifically move to and bind to a particular location in the cell).

In another embodiment of the invention, the inhibitor is a mutein (i.e., a mutated Egr-1 protein). This mutein would include changes, additions, deletions, substitutions to the normally occurring Egr-1 amino acid sequence so that the resultant mutein would lack the acitivty of a normal Egr-1 protein. This mutein would retain acitivity which is required to maintain its ability to act as a competitive inhibitor. For example, one such mutein may retain the ability to bind but lack an enzymatic activity.

The practice of the present invention will employ, unless otherwise indicated, conventional techniques of molecular biology, microbiology, virology, recombinant DNA technology, and immunology, which are within the skill of the art. Such techniques are explained fully in the literature. See, e.g., Sambrook, Fritsch & Maniatis, Molecular Cloning: A Laboratory Manual, Second Edition (1989); DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); and Handbook of Experimental Immunology, Vols. I–IV (D. M. Weir and C. C. Blackwell eds., 1986, Blackwell Scientific Publications).

As used in this specification and the appended claims, the singular forms "a," "an" and "the" include plural references unless the content clearly dictates otherwise.

In another embodiment of the invention, the "introducing" is carried out by a means selected from the group consisting of adenovirus infection, liposome-mediated transfer, topical application to the cell, and microinjection.

In another embodiment of the invention, the administering is carried out via injection, oral administration, or topical administration.

In another embodiment of the invention, the carrier is an aqueous carrier, a liposome, or a lipid carrier.

The present invention provides a pharmaceutical composition which comprises an effective amount of an inhibitor of Egr-1 protein and a pharmaceutically acceptable carrier. In one embodiment, the carrier comprises a diluent. In another embodiment, the carrier comprises an appropriate adjuvant, a herpes virus, a liposome, a microencapsule, a polymer encapsulated cell or a retroviral vector. In another embodiment, the carrier is an aerosol, intravenous, oral or topical carrier.

In one embodiment, the inhibitor of the invention inhibits Egr-1 protein activity. In another embodiment, the inhibitor inhibits mRNA translation, DNA transcription or initiation of DNA transcription.

One embodiment of the present invention is a peptidomimetic compound which is an inhibitor of Egr-1 protein activity or inhibitor of Egr-1 expression, wherein the compound has a bond, a peptide backbone or an amino acid component replaced with a suitable mimic. Examples of unnatural amino acids which may be suitable amino acid mimics include β-alanine, L-α-amino butyric acid, L-γ-amino butyric acid, L-α-amino isobutyric acid, L-ϵ-amino caproic acid, 7-amino heptanoic acid, L-aspartic acid, L-glutamic acid, cysteine (acetamindomethyl), N-ϵ-Boc-N-α-CBZ-L-lysine, N-ϵ-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, Boc-L-thioproline. (Blondelle, et al. 1994; Pinilla, et al. 1995).

Also provided by the invention are pharmaceutical compositions comprising therapeutically effective amounts of polypeptide products of the invention together with suitable diluents, preservatives, solubilizers, emulsifiers, adjuvants and/or carriers. An "effective amount" as used herein refers to that amount which provides a therapeutic effect for a given. condition and administration regimen. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. The choice of compositions will depend on the physical and chemical properties of the protein having the activity of a Factor IXa compound. For example, a product which includes a controlled or sustained release composition may include formulation in lipophilic depots (e.g., fatty acids, waxes, oils). Also comprehended by the invention are particulate compositions coated with polymers (e.g., poloxamers or poloxamines) and the compound coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal, oral, injection or infusion by intravenous, intraperitoneal, intracerebral, intramuscular, intraocular, intraarterial or intralesional.

The present invention incorporates U.S. Pat. Nos. 5,446,128, 5,422,426 and 5,440,013 in their entireties as references which disclose the synthesis of peptidomimetic compounds and methods related thereto. The compounds of the present invention may be synthesized using these methods. The present invention provides for peptidomimetic compounds which have substantially the same three-dimensional structure as those compounds described herein.

In addition to the compounds disclosed herein having naturally-occurring amino acids with peptide or unnatural linkages, the present invention also provides for other structurally similar compounds such as polypeptide analogs with unnatural amino acids in the compound. Such compounds may be readily synthesized on a peptide synthesizer available from vendors such as Applied Biosystems, Dupont and Millipore.

As used herein, the term "pharmaceutically acceptable carrier" encompasses any of the standard pharmaceutically accepted carriers, such as phosphate buffered saline solution, water, emulsions such as an oil/water emulsion or a triglyceride emulsion, various types of wetting agents, tablets, coated tablets and capsules. An example of an acceptable triglyceride emulsion useful in intravenous and intraperitoneal administration of the compounds is the triglyceride emulsion commercially known as Intralipid®.

Typically such carriers contain excipients such as starch, milk, sugar, certain types of clay, gelatin, stearic acid, talc, vegetable fats or oils, gums, glycols, or other known excipients. Such carriers may also include flavor and color additives or other ingredients.

When administered, compounds are often cleared rapidly from the circulation and may therefore elicit relatively short-lived pharmacological activity. Consequently, frequent injections of relatively large doses of bioactive compounds may by required to sustain therapeutic efficacy. Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability. of the compound, and greatly reduce the immunogenicity and reactivity of the compound. As a result, the desired in vivo biological activity may be achieved by the administration of such polymer-compound adducts less frequently or in lower doses than with the unmodified compound.

Attachment of polyethylene glycol (PEG) to compounds is particularly useful because PEG has very low toxicity in mammals (Carpenter et al., 1971). For example, a PEG adduct of adenosine deaminase was approved in the United States for use in humans for the treatment of severe combined immunodef iciency syndrome. A second advantage afforded by the conjugation of PEG is that of effectively reducing the immunogenicity and antigenicity of heterologous compounds. For example, a PEG adduct of a human protein might be useful for the treatment of disease in other mammalian species without the risk of triggering a severe immune response. The compound of the present invention capable of alleviating symptoms of a cognitive disorder of memory or learning may be delivered in a microencapsulation device so as to reduce or prevent an host immune response against the compound or against cells which may produce the compound. The compound of the present invention may also be delivered microencapsulated in a membrane, such as a liposome.

Polymers such as PEG may be conveniently attached to one or more reactive amino acid residues in a protein such as the alpha-amino group of the amino terminal amino acid, the epsilon amino groups of lysine side chains, the sulfhydryl groups of cysteine side chains, the carboxyl groups of aspartyl and glutamyl side chains, the alpha-carboxyl group of the carboxy-terminal amino acid, tyrosine side chains, or to activated derivatives of glycosyl chains attached to certain asparagine, serine or threonine residues.

Numerous activated forms of PEG suitable for direct reaction with proteins have been described. Useful PEG reagents for reaction with protein amino groups include active esters of carboxylic acid or carbonate derivatives, particularly those in which the leaving groups are N-hydroxysuccinimide, p-nitrophenol, imidazole or 1-hydroxy-2-nitrobenzene-4-sulfonate. PEG derivatives containing maleimido or haloacetyl groups are useful reagents for the modification of protein free sulfhydryl groups. Likewise, PEG reagents containing amino hydrazine or hydrazide groups are useful for reaction with aldehydes generated by periodate oxidation of carbohydrate groups in proteins.

Definitions

As used herein "nucleic acid molecule" includes both DNA and RNA and, unless otherwise specified, includes both double-stranded and single-stranded nucleic acids. Also included are hybrids such as DNA-RNA hybrids. Reference to a nucleic acid sequence can also include modified- bases as long as the modification does not significantly interfere either with binding of a ligand such as a protein by the nucleic acid or Watson-Crick base pairing. Two DNA or polypeptide sequences are "substantially homologous" when at least about 80% (preferably at least about 90%, and most preferably at least about 95%) of the nucleotides or amino acids match over a defined length of the molecule. As used herein, "substantially homologous" also refers to sequences showing identity to the specified DNA or polypeptide sequence. DNA sequences that are substantially homologous can be identified in a Southern hybridization, experiment under, for example, stringent conditions, as defined for that particular system. Defining appropriate hybridization conditions is within the skill of the art. See, e.g., Sambrook et al., supra; DNA Cloning, vols I & II, supra; Nucleic Acid Hybridization, supra.

A DNA "coding sequence" or a "nucleotide sequence encoding" a particular protein, is a DNA sequence which is transcribed and translated into a polypeptide in vivo or in vitro when placed under the control of appropriate regulatory sequences. The boundaries of the coding sequence are determined by a start codon at the 5'-(amino) terminus and a translation stop codon at the 3'-(carboxy) terminus. A coding sequence can include, but is not limited to, procaryotic sequences, cDNA from eucaryotic mRNA, genomic DNA sequences from eucaryotic (e.g., mammalian) sources, viral RNA or DNA, and even synthetic nucleotide sequences. A transcription termination sequence will usually be located 3' to the coding sequence.

DNA "control sequences" refers collectively to promoter sequences, polyadenylation signals, transcription termination sequences, upstream regulatory domains, enhancers, and the like, untranslated regions, including 5'-UTRs and 3'-UTRs, which collectively provide for the transcription and translation of a coding sequence in a host cell.

"Operably linked" refers to an arrangement of nucleotide sequence elements wherein the components so described are configured so as to perform their usual function. Thus, control sequences.operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence. A cell has been "transformed" by exogenous DNA when such exogenous DNA has been introduced inside the cell membrane. Exogenous DNA may or may not be integrated (covalently linked) into chromosomal DNA making up the genome of the cell. In procaryotes and yeasts, for example, the exogenous DNA may be maintained on an episomal element, such as a plasmid. In eucaryotic cells, a stably transformed cell is generally one in which the exogenous DNA has become integrated into the chromosome so that it is inherited by daughter cells through chromosome replication, or one which includes stably maintained extrachromosomal plasmids. This stability is demonstrated by the ability of the eucaryotic cell to establish cell lines or clones comprised of a population of daughter cells containing the exogenous DNA.

A "heterologous" region of a DNA construct is an identifiable segment of DNA within or attached to another DNA molecule that is not found in association with the other molecule in nature. One example of a heterologous coding sequence is a construct where the coding sequence itself is not found in nature (e.g., synthetic sequences having codons different from the native gene). Likewise, a chimeric sequence, comprising a heterologous structural gene and a gene encoding an Egr-1 protein or a portion of an Egr-1 protein, linked to a endothelial cell specific promoter will be considered heterologous since such chimeric constructs are not normally found in nature. Allelic variation or naturally occurring mutational events do not give rise to a heterologous region of DNA, as used herein.

Vectors

Especially preferred are virus based vectors. In the case of eukaryotic cells, retrovirus or adenovirus based vectors are preferred. Such vectors contain all or a part of a viral genome, such as long term repeats ("LTRs"), promoters (e.g., CMV promoters, SV40 promoter, RSV promoter), enhancers, and so forth. When the host cell is a prokaryote, bacterial viruses, or phages, are preferred. Exemplary of such vectors are vectors based upon, e.g., lambda phage. In any case, the vector may comprise elements of more than one virus.

The resulting vectors are transfected or transformed into a host cell, which may be eukaryotic or prokaryotic. The gene transfer vector of the present invention may additionally comprise a gene encoding a marker or reporter molecule to more easily trace expression of the vector.

The invention provides for a gene transfer vector which comprises a nucleic acid which encodes a Egr-1 protein. The gene transfer vector may contain more than one gene encoding the same or different foreign polypeptides or RNAs. The gene transfer vector may be any construct which is able to replicate within a host cell and includes plasmids, DNA viruses, retroviruses, as well as isolated nucleotide molecules. Liposome-mediated transfer of the gene transfer vector may also be carried out in the present invention. Examples of such plasmids which can be employed in the present invention include pGL3-based plasmids (Promega). An example of such DNA viruses which can be employed in the present invention are adenoviruses. Adenoviruses have attracted increasing attention as expression vectors, especially for human gene therapy (Berkner, Curr. Top. Microbiol. Immunol., 158:39–66 (1992)).

Examples of such adenovirus serotypes which can be employed in the present invention are well-known in the art and include more than 40 different human adenoviruses, e.g., Ad12 (subgenus A), Ad3 and Ad7 (Subgenus B), Ad2 and Ad5 (Subgenus C), Ad8 (Subgenus D), Ad4 (Subgenus E), Ad40 (Subgenus F) (Wigand et al, In: Adenovirus DNA, Doerfler, Ed., Martinus Nijhoff Publishing, Boston, pp. 408–441 (1986)). Ad5 of subgroup C is the preferred adenovirus employed in the present invention. This is because Ad5 is a human adenovirus about which a great deal of biochemical and genetic information is known, and it has historically been used for most constructions employing adenovirus as a vector. Also, adenoviral vectors are commercially available, e.g., pCA3 (Microbix Biosystems Inc.).

Methods for producing adenovirus vectors are well-known in the art (Berkner et al, Nucleic Acids Res., 11:6003–6020 (1983); van Doren et al, Mol. Cell. Biol., 4:1653–1656 (1984); Ghosh-Choudhury et al, Biochem. Biophys. Res. Commun., 147:964–973 (1987); McGrory et al, Virol., 163:614–617 (1988); and Gluzman et al, In: Eurkaryotic Viral Vectors, Ed. Gluzman, Y. pages 187–192, Cold Spring Harbor Laboratory (1982)).

Preferred vectors for use in the methods of the present invention are viral including adenoviruses, retroviral, vectors, adeno-associated viral (AAV) vectors.

The viral vector selected should meet the following criteria: 1) the vector must be able to infect cells of an ischemic tissue of a subject (wherein the subject can be a human in one embodiment) and thus viral vectors having an appropriate host range must be selected; 2) the transferred gene should be capable of persisting and being expressed in a cell for an extended period of time; and 3) the vector should be safe to the host and cause minimal cell transformation. Retroviral vectors and adenoviruses offer an efficient, useful, and presently the best-characterized means of introducing and expressing foreign genes efficiently in mammalian cells. These vectors have very broad host and cell type ranges, express genes stably and efficiently. The safety of these vectors has been proved by many research groups. In fact many are in clinical trials.

Other virus vectors that may be used for gene transfer into cells for correction of disorders include retroviruses such as Moloney murine leukemia virus (MoMuLV); papovaviruses such as JC, SV40, polyoma, adenoviruses; Epstein-Barr Virus (EBV); papilloma viruses, e.g. bovine papilloma virus type I (BPV); vaccinia and poliovirus and other human and animal viruses.

Adenoviruses have several properties that make them attractive as cloning vehicles (Bachettis et al.: Transfer of gene for thymidine kinase-deficient human cells by purified herpes simplex viral DNA. PNAS USA, 1977 74:1590;

Berkner, K. L.: Development of adenovirus vectors for expression of heterologous genes. Biotechniques, 1988 6:616; Ghosh-Choudhury G., et al., Human adenovirus cloning vectors based on infectious bacterial plasmids. Gene 1986; 50:161; Hag-Ahmand Y., et al., Development of a helper-independent human adenovirus vector and its use in the transfer of the herpes simplex virus thymidine kinase gene. J Virol 1986; 57:257; Rosenfeld M., et al., Adenovirus-mediated transfer of a recombinant alpha..sub.1'-antitrypsin gene to the lung epithelium in vivo. Science 1991; 252:431).

For example, adenoviruses possess an intermediate sized genome that replicates in cellular nuclei; many serotypes are clinically innocuous; adenovirus genomes appear to be stable despite insertion of foreign genes; foreign genes appear to be maintained without loss or rearrangement; and adenoviruses can be used as high level transient expression vectors with an expression period up to 4 weeks to several months. Extensive biochemical and genetic studies suggest that it is possible to substitute up to 7–7.5 kb of heterologous sequences for native adenovirus sequences generating viable, conditional, helper-independent vectors (Kaufman R. J.; identification of the component necessary for adenovirus translational control and their utilization in CDNA expression vectors. PNAS USA, 1985 82:689).

AAV is a small human parvovirus with a single stranded DNA genome of approximately 5 kb. This virus can be propagated as an integrated provirus in several human cell types. AAV vectors have several advantage for human gene therapy. For example, they are trophic for human cells but can also infect other mammalian cells; (2) no disease has been associated with AAV in humans or other animals; (3) integrated AAV genomes appear stable in their host cells; (4) there is no evidence that integration of AAV alters expression of host genes or promoters or promotes their rearrangement; (5) introduced genes can be rescued from the host cell by infection with a helper virus such as adenovirus.

HSV-1 vector system facilitates introduction of virtually any gene into non-mitotic cells (Geller et al. an efficient deletion mutant packaging system for a defective herpes simplex virus vectors: Potential applications to human gene therapy and neuronal physiology. PNAS USA, 1990 87:8950).

Another vector for mammalian gene transfer is the bovine papilloma virus-based vector (Sarver N, et al., Bovine papilloma virus DNA: A novel eukaryotic cloning vector. Mol Cell Biol 1981; 1:486).

Vaccinia and other poxvirus-based vectors provide a mammalian gene transfer system. Vaccinia virus is a large double-stranded DNA virus of 120 kilodaltons (kd) genomic size (Panicali D, et al., Construction of poxvirus as cloning vectors: Insertion of the thymidine kinase gene from herpes simplex virus into the DNA. of infectious vaccine virus. Proc Natl Acad Sci USA 1982; 79:4927; Smith et al. infectious vaccinia virus recombinants that express hepatitis B virus surface antigens. Nature, 1983 302:490.)

Retroviruses are packages designed to insert viral genes into host cells (Guild B, et al., Development of retrovirus vectors useful for expressing genes in cultured murine embryonic cells and hematopoietic cells in vivo. J Virol 1988; 62:795; Hock R. A., et al., Retrovirus mediated transfer and expression of drug resistance genes in human hemopoietic progenitor cells. Nature 1986; 320:275).

The basic retrovirus consists of two identical strands of RNA packaged in a proviral protein. The core surrounded by a protective coat called the envelope, which is derived from the membrane of the previous host but modified with glycoproteins contributed by the virus.

Markers and amplifiers can also be employed in the subject expression systems. A variety of markers are known which are useful in selecting for transformed cell lines and generally comprise a gene whose expression confers a selectable phenotype on transformed cells when the cells are grown in an appropriate selective medium. Such markers for mammalian cell lines include, for example, the bacterial xanthine-guanine phosporibosyl transferase gene, which can be selected for in medium containing mycophenolic acid and xanthine (Mulligan et al. (1981) Proc. Natl. Acad. Sci. USA 78:2072–2076), and the aminoglycoside phosphotransferase gene (specifying a protein that inactivates the antibacterial action of neomycin/kanamycin derivatives), which can be selected for using medium containing neomycin derivatives such as G418 which are normally toxic to mammalian cells (Colbere-Garapin et al. (1981) J. Mol. Biol. 150:1–14). Useful markers for other eucaryotic expression systems, are well known to those of skill in the art.

Infection can be carried out in vitro or in vivo. In vitro infection of cells is performed by adding the gene transfer vectors to the cell culture medium. When infection is carried out in vivo, the solution containing the gene transfer vectors may be administered by a variety of modes, depending on the tissue which is to be infected. Examples of such modes of administration include injection of gene transfer vectors into the skin, topical application onto the skin, direct application to a surface of epithelium, or instillation into an organ (e.g., time release patch or capsule below the skin or into a tumor). Expression can be amplified by placing an amplifiable gene, such as the mouse dihydrofolate reductase (dhfr) gene adjacent to the coding sequence. Cells can then be selected for methotrexate resistance in dhfr-deficient cells. See, e.g. Urlaub et al. (1980) Proc. Natl. Acad. Sci. USA 77:4216–4220; Rungold et al. (1981) J. Mol. and Appl. Genet. 1:165–175.

The above-described system can be used to direct the expression of a wide variety of procaryotic, eucaryotic and viral proteins, including, for example, viral glycoproteins suitable for use as vaccine antigens, immunomodulators for regulation of the immune response, hormones, cytokines and growth factors, as well as proteins useful in the production of other biopharmaceuticals.

It may also be desirable to produce mutants or analogs of the proteins of interest, such as the Egr-1 protein. Such a mutant or analog provided by the present invention would have the ability to act as a competitive inhibitor of the Egr-1 protein itself. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; DNA Cloning, Vols. I and II, supra; Nucleic Acid Hybridization, supra.

The transformation procedure used depends upon the host to be transformed. Mammalian cells can conveniently be transformed using, for example, DEAE-dextran based procedures, calcium phosphate precipitation (Graham, F. L. and Van der Eb, A. J. (1973) Virology 52:456–467), protoplast fusion, liposome-mediated transfer, polybrene-mediated transfection and direct microinjection of the DNA into nuclei. Bacterial cells will generally be transformed using calcium chloride, either alone or in combination with other divalent cations and DMSO (Sambrook, Fritsch & Maniatis, Molecular Cloning: A Laboratory Manual, Second Edition (1989)). DNA can also be introduced into bacterial cells by electroporation. Methods of introducing exogenous DNA into yeast hosts typically include either the transformation of spheroplasts or transformation of intact yeast cells treated with alkali cations.

The constructs can also be used in gene therapy or nucleic acid immunization, to direct the production of the desired gene product in vivo, by administering the expression constructs directly to a subject for the in vivo translation thereof. See, e.g. EPA Publication No. 336,523 (Dreano et al., published Oct. 11, 1989). Alternatively, gene transfer can be accomplished by transfecting the subject's cells or tissues with the expression constructs ex vivo and reintroducing the transformed material into the host. The constructs can be directly introduced into the host organism, i.e., by injection (see International Publication No. WO/90/11092; and Wolff et al., (1990) Science 247:1465–1468). Liposome-mediated gene transfer can also be accomplished using known methods. See, e.g., Hazinski et al., (1991) Am. J. Respir. Cell Mol. Biol. 4:206–209; Brigham et al. (1989) Am. J. Med. Sci. 298:278–281; Canonico et al. (1991) Clin. Res. 39:219A; and Nabel et al. (1990) Science 249:1285–1288. Targeting agents, such as antibodies directed against surface antigens expressed on specific cell types, can be covalently conjugated to the liposomal surface so that the nucleic acid can be delivered to specific tissues and cells for local administration.

Human Gene Therapy and Diagnostic Use of Vector

There are several protocols for human gene therapy which have been approved for use by the Recombinant DNA Advisory Committee (RAC) which conform to a general protocol of target cell infection and administration of transfected cells (see for example, Blaese, R. M., et al., 1990; Anderson, W. F., 1992; Culver, K. W. et al., 1991).

In addition, U.S. Pat. No. 5,399,346 (Anderson, W. F. et al., Mar. 21, 1995, U.S. Ser. No. 220,175) describes procedures for retroviral gene transfer. The contents of these support references are incorporated in their entirety into the subject application. Retroviral-mediated gene transfer requires target cells which are undergoing cell division in order to achieve stable integration hence, cells are collected from a subject often by removing blood or bone marrow. It may be necessary to select for a particular subpopulation of the originally harvested cells for use in the infection protocol. Then, a retroviral vector containing the gene(s) of interest would be mixed into the culture medium. The vector binds to the surface of the subject's cells, enters the cells and inserts the gene of interest randomly into a chromosome. The gene of interest is now stably integrated and will remain in place and be passed to all of the daughter cells as the cells grow in number. The cells may be expanded in culture for a total of 9–10 days before reinfusion (Culver et al., 1991). As the length of time the target cells are left in culture increases, the possibility of contamination also increases, therefore a shorter protocol would be more beneficial.

The basic tasks in the present method of the invention are selecting the proper vector vehicle to deliver the Egr-1 inhibitor to the body and achieving appropriate inhibition of activity of the Egr-1 protein. The present invention provides packaging the inhibitors in such a way that they can be injected directly or administered directly into the bloodstream or relevant organs of patients who need them. The packaging will protect the inhibitor (e.g., foreign DNA) from elimination by the immune system and direct it to appropriate tissues or cells.

The methods described below are merely for purposes of illustration and are typical of those that might be used. However, other procedures may also be employed, as is understood in the art. Most of the techniques used to construct vectors and the like are widely practiced in the art, and most practitioners are familiar with the standard resource materials which describe specific conditions and procedures. However, for convenience, the following paragraphs may serve as a guideline.

General Methods for Vector Construction

Construction of suitable vectors containing the desired therapeutic gene coding and control sequences employs standard ligation and restriction techniques, which are well understood in the art (see Maniatis et al., in Molecular Cloning: A Laboratory Manual, Cold Spring Harbor Laboratory, New York (1982)). Isolated plasmids, DNA sequences, or synthesized oligonucleotides are cleaved, tailored, and religated in the form desired.

Site-specific DNA cleavage is performed by treating with the suitable restriction enzyme (or enzymes) under conditions which are generally understood in the art, and the particulars of which are specified by the manufacturer of these commercially available restriction enzymes (See, e.g. New England Biolabs Product Catalog). In general, about 1 $\mu$g of plasmid or DNA sequences is cleaved by one unit of enzyme in about 20 $\mu$l of buffer solution. Typically, an excess of restriction enzyme is used to insure complete digestion of the DNA substrate.

Incubation times of about one hour to two hours at about 37 degree. C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in Methods in Enzymology 65:499–560 (1980). Restriction cleaved fragments may be blunt ended by treating with the large fragment of E. coli DNA polymerase I (Klenow) in the presence of the four deoxynucleotide triphosphates (dNTPs) using incubation times of about 15 to 25 min at 20.degree. C. to 25.degree. C. in 50 mM Tris (pH 7.6) 50 mM NaCl, 6 mM MgCl.sub.2, 6 mM DTT and 5–10.mu.M dNTPs. The Klenow fragment fills in at 5' sticky ends but chews back protruding 3' single strands, even though the four dNTPs are present. If desired, selective repair can be performed by supplying only one of the dNTPs, or with selected dNTPs, within the limitations dictated by the nature of the sticky ends. After treatment with Klenow, the mixture is extracted with phenol/chloroform and ethanol precipitated. Treatment under appropriate conditions with Sl nuclease or Bal-31 results in hydrolysis of any single-stranded portion.

Ligations are performed in 10–50 $\mu$l volumes under the following standard conditions and temperatures using T4 DNA ligase. Ligation protocols are standard (D. Goeddel (ed.) Gene Expression Technology: Methods in Enzymology (1991)). In vector construction employing "vector fragments", the vector fragment is commonly treated with bacterial alkaline phosphatase (BAP) or calf intestinal alkaline phosphatase (CIP) in order to remove the 5' phosphate and prevent religation of the vector. Alternatively, religation can be prevented in vectors which have been double digested by additional restriction enzyme digestion of the unwanted fragments.

Suitable vectors include viral vector systems e.g. ADV, RV, and AAV (R. J. Kaufman "Vectors used for expression in mammalian cells" in Gene Expression Technology, edited by D. V. Goeddel (1991). Many methods for inserting functional DNA transgenes into cells are known in the art.

For example, non-vector methods include nonviral physical transfection of DNA into cells; for example, microinjection (DePamphilis et al., BioTechnique 6:662–680 (1988)); liposomal mediated transfection (Felgner et al., Proc. Natl. Acad. Sci. USA, 84:7413–7417 (1987), Felgner and Holm, Focus 11:21–25 (1989) and Felgner et al., Proc. West. Pharmacol. Soc. 32: 115–121 (1989)) and other methods known in the art.

Administration of Modified Vectors Into Subject

One way to get DNA into a target cell is to put it inside a membrane bound sac or vesicle such as a spheroplast or liposome, or by calcium phosphate precipitation ($CaPO_4$) (Graham F. and Van der Eb, A., Virology 52:456 1973; Schaefer-Ridder M., et al., Liposomes as gene carriers: Efficient transduction of mouse L cells by thymidine kinase gene. Science 1982; 215:166; Stavridis J. C., et al., Construction of transferrin-coated liposomes for in vivo transport of exogenous DNA to bone marrow erythroblasts in rabbits. Exp Cell Res 1986; 164:568–572).

A vesicle can be constructed in such a way that its membrane will fuse with the outer membrane of a target cell. The vector of the invention in vesicles can home into the cancer cells.

The spheroplasts are maintained in high ionic strength buffer until they can be fused through the mammalian target cell using fusogens such as polyethylene glycol.

Liposomes are artificial phospholipid vesicles. Vesicles range in size from 0.2 to 4.0 micrometers and can entrap 10% to 40% of an aqueous buffer containing macromolecules. The liposomes protect the DNA from nucleases and facilitate its introduction into target cells. Transfection can also occur through electroporation. Before administration, the modified vectors are suspended in complete PBS at a selected density for injection. In addition to PBS, any osmotically balanced solution which is physiologically compatible with the subject may be used to suspend and inject the modified vectors into the host.

For injection, the cell suspension is drawn up into the syringe and administered to anesthetized recipients. Multiple injections may be made using this procedure. The viral suspension procedure thus permits administration of genetically modified vectors to any predetermined site in the skin, is relatively non-traumatic, allows multiple administrations simultaneously in several different sites or the same site using the same viral suspension. Multiple injections may consist of a mixture of therapeutic genes.

Survival of the Modified Vectors So Administered

Expression of a gene is controlled at the transcription, translation or post-translation levels. Transcription initiation is an early and critical event in gene expression. This depends on the promoter and enhancer sequences and is influenced by specific cellular factors that interact with these sequences. The transcriptional unit of many prokaryotic genes consists of the promoter and in some cases enhancer or regulator elements (Banerji et al., Cell 27:299 (1981); Corden et al., Science 209:1406 (1980); and Breathnach and Chambon, Ann. Rev. Biochem. 50:349 (1981)). For retroviruses, control elements involved in the replication of the retroviral genome reside in the long terminal repeat (LTR) (Weiss et al., eds., In: The molecular biology of tumor viruses: RNA tumor viruses, Cold Spring Harbor Laboratory, Cold Spring Harbor, N.Y. (1982)). Moloney murine leukemia virus (MLV) and Rous sarcoma virus (RSV) LTRs contain promoter and enhancer sequences (Jolly et al., Nucleic Acids Res. 11:1855 (1983); Capecchi et al., In: Enhancer and eukaryotic gene expression, Gulzman and Shenk, eds., pp. 101–102, Cold Spring Harbor Laboratories, Cold Spring Harbor, N.Y.).

Promoter and enhancer regions of a number of non-viral promoters have also been described (Schmidt et al., Nature 314:285 (1985); Rossi and de Crombrugghe, Proc. Natl. Acad. Sci. USA 84:5590–5594 (1987)).

In addition to using viral and non-viral promoters to drive therapeutic gene expression, an enhancer sequence may be used to increase the level of therapeutic gene expression. Enhancers can increase the transcriptional activity not only of their native gene but also of some foreign genes (Armelor,,Proc. Natl. Acad. Sci. USA 70:2702 (1973)).

The most effective mode of administration and dosage regimen for the molecules of the present invention depends upon the exact location and integrity of the ischemic tissue to be treated, the subject's health and response to treatment and the judgment of the treating physician. Accordingly, the dosages of the compounds (inhibitors) should be titrated to the individual subject. The compounds may be delivered directly or indirectly via another cell, autologous cells are preferred, but heterologous cells are encompassed within the scope of the invention.

The interrelationship of dosages for animals of various sizes and species and humans based on $mg/m^2$ of surface area is described by Freireich, E. J., et al. Cancer Chemother., Rep. 50 (4):219–244 (1966). Adjustments in the dosage regimen may be made to optimize the tumor cell growth inhibiting and killing response, e.g., doses may be divided and administered on a daily basis or the dose reduced proportionally depending upon the situation (e.g., several divided dose may be administered daily or proportionally reduced depending on the specific therapeutic situation).

It would be clear that the dose of the molecules of the invention required to achieve cures may be further reduced with schedule optimization.

This invention is illustrated in the Experimental Details section which follows. These sections are set forth to aid in an understanding of the invention but are not intended to, and should not be construed to, limit in any way the invention as set forth in the claims which follow thereafter.

EXPERIMENTAL DETAILS

EXAMPLE 1

Early Grouth Response (EGR-1) is a Master Switch in the Pathogenesis of Ischemic Stress Abbreviations used: Egr, early growth response; EMSA, electrophoretic mobility shift assay; ICAM, intercellular adhesion molecule; HIF, hypoxia inducible factor; IL, interleukin; I/R, ischemia/reperfusion; ISH, in situ hybridization; JE/MCP-1, macrophage chemotactic protein-1; L32, ribosomal structural protein; LTβ, lymphotoxin β; MIF, macrophage migration inhibitory factor; MIP, macrophage inflammatory protein; MP, mononuclear phagocyte; PAI, plasminogen activator inhibitor; TF, tissue factor; and, VEGF, vascular endothelial growth factor.

Activation of the zinc finger transcription factor Early growth response (Egr)-1[1-2], initially linked to developmental processes [3], is shown here to function as a master switch tripped by ischemia to trigger expression of pivotal regulators of coagulation, inflammation and vascular hyperpermeability. Deletion of the Egr-1 gene strikingly diminished expression of these mediators of vascular injury in a murine model of lung ischemia/reperfusion, and enhanced animal survival and organ function. Rapid activation of Egr-1 in response to oxygen deprivation primes the vasculature for dysfunction manifest during reperfusion. These studies define a central role for Egr-I activation in the pathogenesis of tissue damage in ischemia.

It has long been hypothesized that ischemia primes mechanisms leading to reperfusion injury and sets the stage for an exaggerated, maladaptive vascular response eventuating in tissue damage. Hypoxemia, a central component of the ischemic vascular milieu, has been defined as a key factor initiating vascular injury. To date, the cellular response to oxygen deprivation has largely been defined by studies of the transcription factor HIF (Hypoxia-Inducible Factor)-1[4-6]. Activation of HIF-1 by hypoxia/hypoxemia facilitates metabolic adaptation to environmental challenge; glucose uptake by the noninsulin-dependent glucose transporter (GLUT1) is enhanced, and expression of glycolytic enzymes, erythropoietin and Vascular Endothelial Growth Factor (VEGF) is amplified[4-6]. However, another facet of the cellular response to hypoxia has been revealed by the deposition of fibrin in lung vasculature consequent to induction of procoagulant tissue factor[7]. As tissue factor expression depended on hypoxia-mediated activation of Egr-1 within minutes of oxygen deprivation (and was independent of HIF-1)[7,8], we tested the hypothesis that induction/activation of Egr-1 might link a broad spectrum of mechanisms underlying vascular dysfunction early in ischemia to events triggering tissue injury during later reperfusion.

Results

Egr-1 regulation of coagulation-related cofactors and VEGF. Because of its rich vascular network, the lung provided an ideal model system to assess the role of Egr-1 in susceptibility to ischemia-induced vascular dysfunction. Egr-1 null mice[9] and age/strain-matched littermate controls were subjected to left lung ischemial[10]. We first sought evidence for Egr-1-mediated regulation of a range of procoagulant and proinflammatory factors. Transcripts for tissue factor (TF), the trigger of the procoagulant pathway in vivo, increased ~15-fold in the I/R lung of wild-type mice ($p<0.01$) compared with Egr-1 null mice in whom only ~3-fold enhancement was seen (FIG. 1A). In situ hybridization (ISH) showed virtually undetectable tissue factor MRNA in lungs of control (noninstrumented) wild-type mice (FIG. 1B-1), whereas after I/R, transcripts were evident in lung vasculature (FIG. 1B-2) and mononuclear phagocytes (MPs) (FIG. 1B-3; B-4 shows colocalization with F4/80 immunoreactivity, a MP marker, in an adjacent section). Consistent with these results, immunostaining showed low levels of tissue factor antigen in uninstrumented lungs from wild-type mice (FIG. 1C-1), whereas I/R caused striking induction of tissue factor antigen in the vasculature (FIG. IC-2) and MPs. In contrast, the I/R lung from Egr-1 null mice displayed virtually no increase in tissue factor antigen compared with wild-type mice (FIG. 1C-3, 4).

An important determinant of fibrin deposition is its clearance by the fibrinolytic system. Plasminogen activator inhibitor (PAI)-1 is the major inhibitor of tissue- and urokinase-type plasminogen activators[11,12]. Lung I/R in wild-type mice induced ~12-fold increase in mRNA for PAI-1 ($p<0.01$) compared with Egr-1 null animals in whom only ~3-fold increase was observed (FIG. 1D). ISH showed elevated PAI-1 transcripts in lung vasculature (FIG. 1E-2) and MPs (IE-3, 4) of wild-type mice after I/R, compared with uninstrumented controls (FIG. 1E-1). By immunostaining, enhanced PAI-1 antigen was closely associated with the vasculature in lungs of wild-type mice subject to I/R (FIG. IF-2; PAI-1 antigen was also present in MPs), compared with low levels of PAI-I in lungs from control animals (FIG. IF-1). Similar studies with Egr-1 null mice showed low levels of PAI-1 antigen in the lung even with I/R (FIG. IF-4; F-3 shows uninstrumented lung from an Egr-1 null animal). Thus, the two critical determinants of vascular fibrin formation/deposition, expression of tissue factor and PAI-1, are regulated by Egr-1 in I/R.

Egr-1 was next investigated for its potential to regulate expression of another key vascular homeostatic mediator, VEGF. The latter was first-identified by its effect on vascular permeability, in addition to its angiogenic properties[13,14]. Rapid induction of VEGF has been observed -in models of cerebral ischemia[15] and, clinically, in myocardial infarction[16]. Furthermore, antagonism of VEGF has been shown to reduce stroke volume, and associated tissue edema, in a murine model[17], consistent with a pathogenic role for this angiogenic factor in ischemic tissue injury. The lung of wild-type mice subject to I/R demonstrated ~11-fold induction of VEGF mRNA ($p<0.01$), in contrast to Egr-1 null mice in whom there was only ~2.6-fold increase (FIG. 2A). By ISH, although VEGF transcripts were virtually undetectable in lungs from control wild-type mice (FIG. 2B-1), following I/R, the lung showed a striking increase in VEGF mRNA in the vasculature (FIG. 2B-2) and in MPs (FIG. 2B-3, 4). VEGF antigen in wild-type mice was localized to the vasculature of the reperfused lung (FIG. 2C-2), versus undetectable levels in control lung (FIG. 2C-1). In contrast, the I/R lung from Egr-1 null mice displayed undetectable antigen (FIG. 2C-4; C-3 shows lung from a control Egr-1 null mouse). These data demonstrate a previously unrecognized role for Egr-1 in regulation of VEGF subsequent to I/R injury.

Egr-I regulation of ICAM-1, and cytokine/chemokines. A central facet of tissue injury in I/R results from exaggeration of the inflammatory response. An increase of ~17-fold in MRNA for Intercellular Adhesion Molecule (ICAM)-I was observed in the lung from wild-type mice subject to I/R ($p<0.01$) versus only ~2.2-fold increase in the I/R lung from Egr-1 null mice (FIG. 3A). The striking induction of ICAM-1 in wild-type mice is consistent with its known role in ischemic tissue damage. ISH demonstrated low levels of ICAM-1 mRNA in uninstrumented lungs from wild type mice (FIG. 3B-1), whereas the I/R lung displayed strong expression of ICAM-1 transcripts in the vasculature (FIG. 3B-2) and MPs (FIG. 3B-3, 4). ICAM-1 antigen in wild-type mice was prominent in the vasculature of the reperfused lung (FIG. 3C-2), whereas only low levels of ICAM-1 immunoreactivity were observed in control lung (FIG. 3C-1). In contrast to these results in wild type mice, the I/R lung of Egr-1 null animals displayed only low levels of ICAM-1 antigen (FIG. 3C-4; C-3 shows a control Egr-1 null mouse).

Furthermore, proinflammatory cytokines and chemokines have been proposed to contribute importantly to tissue injury in I/R, both through their direct effects and by induction of cofactors/cell adhesion molecules such as tissue factor, PAI-1 and ICAM-1. For example, induction of Interleukin (IL)-1 has been noted in the immediate reperfusion period in a heterotopic mouse transplant model, and administration of IL-1 receptor antagonist improved graft survival[19]. Enhanced expression of IL-1 also occurs in models of tissue ischemia, including those involving renal, hepatic, brain and peripheral nerve[20-23]. Interleukin (IL)-1$\beta$ mRNA was increased ~21-fold in the I/R lung of wild-type mice ($p<0.01$) compared with Egr-1 null animals in which only ~2.6 fold enhancement was seen (FIG. 4A). ISH localized IL-1$\beta$ transcripts to the vasculature (FIG. 4B2) and MPs (FIG. 4B-3, 4) of the reperfused lung. This distribution of IL-1$\beta$ mRNA was strikingly similar to that observed for tissue factor transcripts (FIG. 1B). IL-1$\beta$ mRNA levels were low in lungs from wild-type mice not undergoing the I/R protocol (FIG. 4B-1). Consistent with elevated IL-1β transcripts after I/R, ELISA of sera from wild-type mice subjected to lung I/R displayed ~20-fold increase in IL-1β antigen (FIG. 4C; p<0.01). In contrast, Egr-1 null mice showed only low levels of IL-1β in response to I/R; IL-1β antigen was barely above the baseline in mouse sera (FIG. 4C).

Indeed, this pattern of vascular and MP expression of IL-1β, which occurred in an Egr-1-dependent manner, included multiple chemokines. For example, upregulation of Macrophage inflammatory Protein (MIP)-2, a CXC chemokine with prominent effects on neutrophils[24,25], has previously been demonstrated in renal, hepatic and hindlimb ischemia models[20,26-21]. Furthermore, MIP-2 has been shown to have a pathogenic role in ischemic hindlimb injury[29]. Northern analysis showed ~16-fold induction of MIP-2 transcripts in the I/R lung from wild-type mice (p<0.01), whereas Egr-1 null mice showed only ~3-fold increase (FIG. 4D). Such MIP-2 transcripts in the reperfused lung from wild-type mice were localized to the vasculature (FIG. 4E-2), as well as to MPs (FIG. 4E-3, 4), by ISH, whereas only low levels of M1P-2 mRNA were observed in uninstrumented mice (FIG. 4E-1). ELISA demonstrated ~15-fold rise in MIP-2 antigen in sera of wild-type mice undergoing lung L/R (FIG. 4F; p<0.01), whereas MIP-2 antigen was barely above the limit of detection in Egr-1 null mice. Induction of Macrophage Chemotactic Protein (JE/MCP)-1, a CC chemokine well-known for its chemotactic and activating effects on monocytes[24,25], has been shown in a model of cerebral ischemia in rats[30]. Transcripts for JE/MCP-1 were ~17-fold increased in the I/R lung of wild-type mice (p<0.01) versus only a slight increase in Egr-1 null mice (FIG. 4G). ISH again showed the predominant site for JE/MCP-1 transcripts to be the vasculature (FIG. 4H-2) and MPs (FIG. 4H-3, 4), whereas little expression was observed in lungs from control mice (FIG. 4H-1). A 15-fold elevation in JE/MCP-1 antigen was detected in sera from wild-type mice subjected to lung I/R (p<0.01), whereas Egr-1 null mice showed only ~2.5-fold increase (FIG. 4I).

These data demonstrate that in I/R, Egr-1 mediates induction of IL-1β and chemokines from both CC and CXC classes. Such mediators amplify pathogenicity by recruiting/activating cellular targets in the blood, such as neutrophils, monocytes and lymphocytes, as well as cells of the vessel wall, including endothelium and smooth muscle cells. The power of this mechanism was further shown by studies demonstrating Egr-1-dependent induction of transcripts for other chemokines, such as IP-10, a CXC chemokine[24,25] previously reported to be expressed in cerebral and hepatic ischemia[26,11], and RANTES, a CC chemokine[24,25]. In the I/R lung from wild-type mice, Northern analysis showed ~14-fold increase in IP-10 (FIG. 4J; p<0.01) and ~13-fold increase in RANTES transcripts (FIG. 4K; p<0.01). In contrast, the I/R lung from Egr-1 null animals showed little increase in either IP-10 or RANTES transcripts (FIG. 4J-K). Studies of transcripts for chemokine receptors (CCR1, 2, 3 & 5, CXCR2, CXCR4) demonstrated detectable levels which remained the same or increased in the I/R lung, indicating the likelihood that the chemokines produced under these conditions were capable of exerting their effects on cellular properties. It is important to note that the Egr-1 genotype of the animals did not affect all genes whose expression was induced by I/R. For example, in the I/R lung, transcripts for Lymphotoxin β (LTβ) increased comparably with tissue from wild-type and Egr-1 null mice, as demonstrated by ribonuclease protection assays (FIG. 4L; ~10-fold in each case). Furthermore, expression of other proinflammatory genes was not affected by I/R, as demonstrated by the lack of change in levels of transcripts for Macrophage Migration Inhibitory Factor (MIF) in wild-type and Egr-1 null mice with or without I/R (FIG. 4L; note, L32 is a ribosomal structural protein used as a control).

Expression of Egr-1 in lung I/R. Based on our observations concerning Egr-1 regulation of gene expression in I/R, we anticipated that Egr-1 induction and activation would occur early during the ischemic period. Northern analysis of RNA harvested from wild-type mice displayed increased Egr-1 transcripts in the ischemic lung within 15 min (~3.3-fold; p<0.05; FIG. 5A), which rose further in the ischemic period (~10–13-fold; p<0.01), and were even more elevated by reperfusion (~20-fold; p<0.01). In contrast, MRNA for another transcription factor, Sp1, was not significantly altered in the I/R lung. ISH of the L/R lung from wild-type mice localized Egr-1 mRNA to the vasculature (FIG. 5B-2) and MPs (FIG. 5B-3, 4) compared with uninstrumented controls (FIG. 5B-1). Consistent with these data, immunoblotting of nuclear extracts prepared from lung tissue of wild-type mice with anti-Egr-1 IgG (FIG. 5C) showed an immunoreactive band of increased intensity by 30 min (FIG. 5C, lane 2; 5D shows quantitation), compared with uninstrumented controls (lane 1). This band was further enhanced by 60 min of ischemia (lane 4;=10-fold; p<0.01) and even more by subsequent reperfusion (lane 5;=12-fold; p<0.01). In contrast, there was no change in levels of Sp1 in nuclear extracts from the I/R lung (FIG. 5C, lanes 6–10). Immunostaining showed virtually undetectable Egr-1 in control lungs (FIG. 5E-1), whereas the I/R lung displayed striking expression of Egr-1 antigen in the vasculature (FIG. 5E-2) and MPs. Electrophoretic mobility shift analysis (EMSA) with Egr probe and nuclear extracts prepared from I/R. lung of wild-type mice (FIG. 5F; 5H shows quantitation) demonstrated a clearly enhanced gel shift band within 30 min of ischemia (FIG. 5F, lane 4) whose intensity increased over the 60 min ischemic period (lane 5) and was slightly further enhanced by I/R (lane 6), compared with a virtually undetectable signal in control mice (lane 2). That this gel shift band was due to Egr-1 interaction with its cognate DNA binding site was shown in supershift assays with anti-Egr-1 IgG (lane 7–8), but not nonimmune IgG (lane 9–10), and by competition assays in which unlabeled Egr probe blocked (lane 11–12), but unlabeled Sp 1 probe did not block appearance of the gel shift band (lane 13–14). In contrast, EMSA with Sp1 probe and nuclear extracts from lung subject to I or I/R did not display a change in intensity of the gel shift band (FIG. 5G, lanes 2–6), and, thus, Sp1 was used to standardize the change in intensity of the Egr-1 gel shift band (FIG. 5H). These data are consistent with the previously observed association of Egr-1 induction and/or activation with renal and cardiac ischemia[32-34]. However, by themselves, such studies cannot establish a causal relationship between Egr-1 and ischemic damage.

Effect of Egr-1 on the outcome of lung I/R. The critical test of these concepts, then, was whether tissue injury in Egr-1 null mice would be diminished in response to lung L/R. Following a 1 hr period, in which blood flow to the left lung was blocked, perfusion was restored for 3 hrs. Then, function of the ischemic/reperfused (I/R) left lung was assessed after preventing blood flow to the light lung (i.e., the animal was dependent on the lung subject to I/R). Compared with wild-type mice, mortality was reduced (p=0.037) and arterial oxygen tension was increased (p=0.009) in Egr-1 null mice (FIG. 6A–B). Two other parameters closely linked to lung injury, fibrin deposition and leukocyte sequestration, were decreased in Egr-1 null mice (FIG. 6C–D). Compared with control/uninstrumented mice, in whom tissue fibrin content remained. low (FIG. 6C, lane 1), time dependent fibrin deposition, detected by immunoblotting of plasmin-digested tissue extracts, was observed in the left lung of wild-type mice by 1 hr of ischemia (FIG. 6C, lane 2). Fibrin deposition in the I/R lung was further amplified during the next 3 hrs of reperfusion (FIG. 6C, lane 3–5). In contrast, fibrin in the I/R lung of Egr-1 null mice was present at much reduced levels (FIG. 6C, lanes 7–10). Leukocyte accumulation, a hallmark of reperfusion injury[35], was also evident in the I/R lung from wild-type mice, based on measurement of myeloperoxidase activity in tissue extracts. Myeloperoxidase activity in I/R lung was significantly reduced in Egr-1 null mice (FIG. 6D; p=0.00 1). Finally, vascular permeability in the reperfused lung, based on a ratio of wet/dry weight, was also decreased in Egr-1 null mice compared with wild-type controls (FIG. 6E; p=0.026). These data suggested that Egr-1 did participate in regulating activation of coagulation, leukocyte accumulation, and vascular permeability in the I/R lung, each of which has an important impact on end-organ function.

Triggering of Egr-1 activation in ischemia program the cytokine/chemokine response to I/R. Taken together, our findings suggested that rapid expression and activation of Egr-1 in the ischemic lung at the earliest stages of oxygen deprivation might serve as the trigger for subsequent induction of mediators regulating vascular and leukocyte/NV properties. To assess this, animals underwent normobaric hypoxia (6% oxygen) without reperfusion and lung RNA was analyzed one hour later to detect IL-1β, MIP-2, and JE/MCP-1 transcripts by ribonuclease protection assays (FIG. 7A). In each case, the level of cytokine/chemokine mRNA was strongly elevated in wild-type mice exposed to hypoxia (~12-, 17- and 10-fold, respectively; p<0.0 1, in each case) compared with minimal to absent expression in mice lacking Egr-1. ISH showed mRNA for IL-1β and these chemokines (MIP-2 and JE/MCP-1) to be localized in the vasculature and MPs, analogous to the distribution of these transcripts in the lung subjected to I/R. In contrast to this suppression of Egr-1-mediated events in the knockut mice, levels of transcripts for LTβ were comparably increased in wild-type and Egr-1 null mice subjected to hypoxia (~10-fold-in each case), and there was no effect of hypoxia on mRNA for MIF, L32 or IL-7 (FIG. 7B).

Discussion

These data provide insight into a previously unidentified role for Egr-1 as a master switch regulating a range of effector mechanisms underlying ischemic stress. The approximately parallel induction of tissue factor, PAI-1, ICAM-1 and VEGF, as well as IL-1β and chemokines (both ELR, such as IP-10, and ELR+, such as MIP-2)[24-25], with respect to the timing and sites for their expression, is consistent with rapid Egr-1 induction/activation early in hypoxia, rather than a mechanism in which one mediator, such as IL-1β, is expressed proximally and causes downstream expression of the others. However, following I/R, the lung is bathed in an environment rich in IL-1β, JE/MCP-1 and VEGF, and these factors (as well as others) could certainly amplify fibrin accumulation, initiated by a more proximal effect of Egr-1 on expression of tissue factor and PAI-1[16-11]. Similarly, the ICAM-1 promoter has been shown to have functional Egr-1 DNA binding motifs[39], allowing for direct induction of ICAM-1 by Egr-1, which may be augmented by the action of IL-1β and chemokines in the ischemic lung[36]. Although in vitro studies have shown VEGF expression to be under control of both HIF-1[40] and Egr-1[41], the Egr-1 null mouse subject to ischemia did not display enhanced VEGF expression, consistent with the proposed central role for Egr-1 in ischemic stress.

There are several possible mechanisms through which Egr-1 could exert such global effects in IR. First, the Egr-1 DNA binding motif is present in a range of genes relevant to vascular homeostasis and dysfunction[42], and lack of Egr-1 could directly attenuate expression of the respective mRNAs. Second, absence of Egr-1 might allow its corepressors, especially the inducible molecule Nab-2[43], to interact with other transcription factors affecting regulation of a spectrum of genes. Additional mechanisms can be envisioned whereby deletion of Egr-1 destabilizes yet to be identified complexes of transcriptional regulators in which its participation facilitates assembly and function. Although further studies will be required to dissect such underlying mechanisms, our results highlight a prominent role for Egr-1 in the pathogenesis of ischemic stress. Indeed, rapid activation and induction of Egr-1 after oxygen deprivation suggest that early in ischemia molecular events programming the vascular response during reperfusion, in fact, are well underway. These data contrast with NF-KB, another transcription factor contributing to control of the host response in ischemia[44,45], but one which also has important protective properties[46,47].

Finally, in view of the virtually normal phenotype of Egr-1 null mice[9] (i.e., no essential homeostatic processes are interrupted), our data suggest that short-term antagonism of Egr-1 may provide an unexpected therapeutic target to diminish maladaptive host responses incited by acute ischemia.

Methods

Murine model of L/R. Egr-1 null and wild-type mice were subjected to the I/R procedure according to protocols approved by the IACUC at Columbia University, and in accordance with the AALAC guidelines. Both Egr-1 null and wild-type controls (8–12 weeks old) were in a similar mixed background (129xC57BL6). Left lung ischemia was performed as described[10].

Survival experiments. The surgical operator was blinded by a colleague in the laboratory as to mouse genotype. For all groups, the experimental procedures were as follows. After one hour of ischemia, followed by 3 hours of reperfusion, the contralateral (right) hilum was permanently ligated, so that the animal's survival and gas exchange depended solely on the reperfused left lung for 30 min. Survival during this period was defined as described[10], and is shown in FIG. 6A. Arterial blood gas analysis (sampled from the left ventricle) was performed in mice which survived the 30 min period after right hilar ligation. Wet/dry lung ratio was determined in mice subjected to I/R and sacrificed immediately thereafter. The left hilum was ligated and then the left lung (including residual blood) was harvested and weighed (wet weight). The lung specimen was desiccated at 80° C. for 24 hrs and weighed again as dry weight. Wet weight was divided by dry weight to calculate the wet/dry ratio[10].

Myeloperoxidase activity in lung homogenized in hexadecyltrimethylammonium bromide followed by three freeze/thaw cycles to release the enzyme from leukocyte granules was measured as described[48].

Immunocytochemical studies were performed on formalin-fixed, paraffin-embedded pieces of lung using the following primary antibodies: goat anti-mouse VEGF IgG (20 μg/ml; R&D), sheep anti-mouse PAI-1 IgG (2 μg/ml;

American Diagnostica), goat anti-mouse IL-1β IgG (2 μg/ml; R&D), rabbit anti-Egr-1 IgG (8 μg/ml; Santa Cruz), rat F4/80 monoclonal antibody (10 μg/ml; PharMingen), rabbit anti-tissue factor IgG (63 μg/ml)[7], and hamster anti-murine ICAM-1 IgG (10 μg/ml; PharNfingen). Secondary antibodies (affinity-purified alkaline phosphatase-conjugated antirabbit, anti-sheep, anti-goat and anti-rat IgG's, and biotinylated anti-hamster IgG) and substrates were employed as described previously[8]. In each case, studies were performed with the same species and concentration of nonimmune IgG and specific antibody. Results are shown with the specific antibody, and studies with nonimmune IgG displayed only background levels of staining.

In situ hybridization. Murine cDNA's for IL-1β, MIP-2, JE/MCP-1, VEGF, ICAM-1, PAI-1, Egr-1 and tissue factor were prepared by RT-PCR with primers whose sequence was selected based on Genebank. After DNA sequencing, the cDNA's were cloned into PCR-II (InVitrogen) or pGEMT Vector (Promega). Plasmids were then linearized for in vitro run-off synthesis to prepare sense and antisense RNA probes, and in situ hybridization was performed on lung as described[49]. Sections were counterstained with methylene green (1%; Sigma). In each case, experiments were performed with sense and antisense riboprobes for the indicated marker. Data are displayed with the antisense probe, and studies with the sense probe showed only background staining.

Northern analysis. Total RNA was extracted from lung, followed by electrophoresis, transfer to Duralon-UV membranes (Stratagene) and hybridization with $^{32}$P-labeled CDNA probes for mouse Egr-1[8], tissue factor[7], ICAM-1 (ATCC), RANTES (ATCC), IP-10 (ATCC), JE/MCP-1, IL-1β, MIP-2, and VEGF (for the latter three, cDNA's were subcloned as described above). Northern blots were also hybridized with $^{32}$p-labeled β-actin as an internal control for RNA loading. Autoradiograms were analyzed by densitometric scanning from at least three different experiments (a representative autoradiogram is shown in the figures). Absorption values were normalized to the B-actin band, and data shown are mean±SEM. Ribonuclease protection assays employed total RNA isolated from the lung and probes for the indicated chemokines/cytokines provided by the manufacturer (Riboquant, PharNlingen).

Western blotting of tissue samples for fibrin was performed on lung harvested from animals treated with heparin (10 U/g body weight, resulting in an APTT>300 s) prior to sacrifice[7]. Tissue was subjected to immunoblotting with anti-fibrin antibody as described[7]. Immunoblotting for Egr-1 and Sp1 employed nuclear extracts prepared from lung as described[7].

ELISAs for IL-1β, MIP-2, and JE/MCP-1 were performed using kits purchased from R&D for murine forms of these mediators. Samples of sera under each experimental condition were obtained from five different mice.

EMSA for Egr-1 utilized nuclear extracts prepared from lungs of mice subjected to the indicated procedure followed by gel shift assay with double-stranded oligonucleotide $^{32}$p-labeled probes for Egr or Sp1 (Santa Cruz) as described[8]. For competition studies, an 100-fold molar excess of unlabeled probes for either Egr (Santa Cruz Biotechnology) or Sp1 (Promega) was added. Supershift assays employed anti-Egr-1 IgG and nonimmune IgG (2 μg/ml in each case), also obtained from Santa Cruz.

Induction of hypoxia in mice was performed in animals subjected to normobaric hypoxia (N=5 per experimental condition unless indicated otherwise) for 4 hrs using a previously described chamber with a final oxygen concentration of 5.5–6.5%[7]. Hypoxia resulted in tachypnea and reduced activity, compared with normoxic counterparts, but no mortality occurred.

For statistical analysis, myeloperoxidase activity data were analyzed using the Mann-Whitney U test for unpaired variables, animal survival after lung I/R was evaluated by contingency analysis using the $X^2$ statistic, and serum values of IL-1β, MIP-2 and JE/MCP-1 were analyzed by ANOVA.

Example 2

Egr-1 Suppression in Isogeneic Rat Lung Transplant Model System

Figure 10:
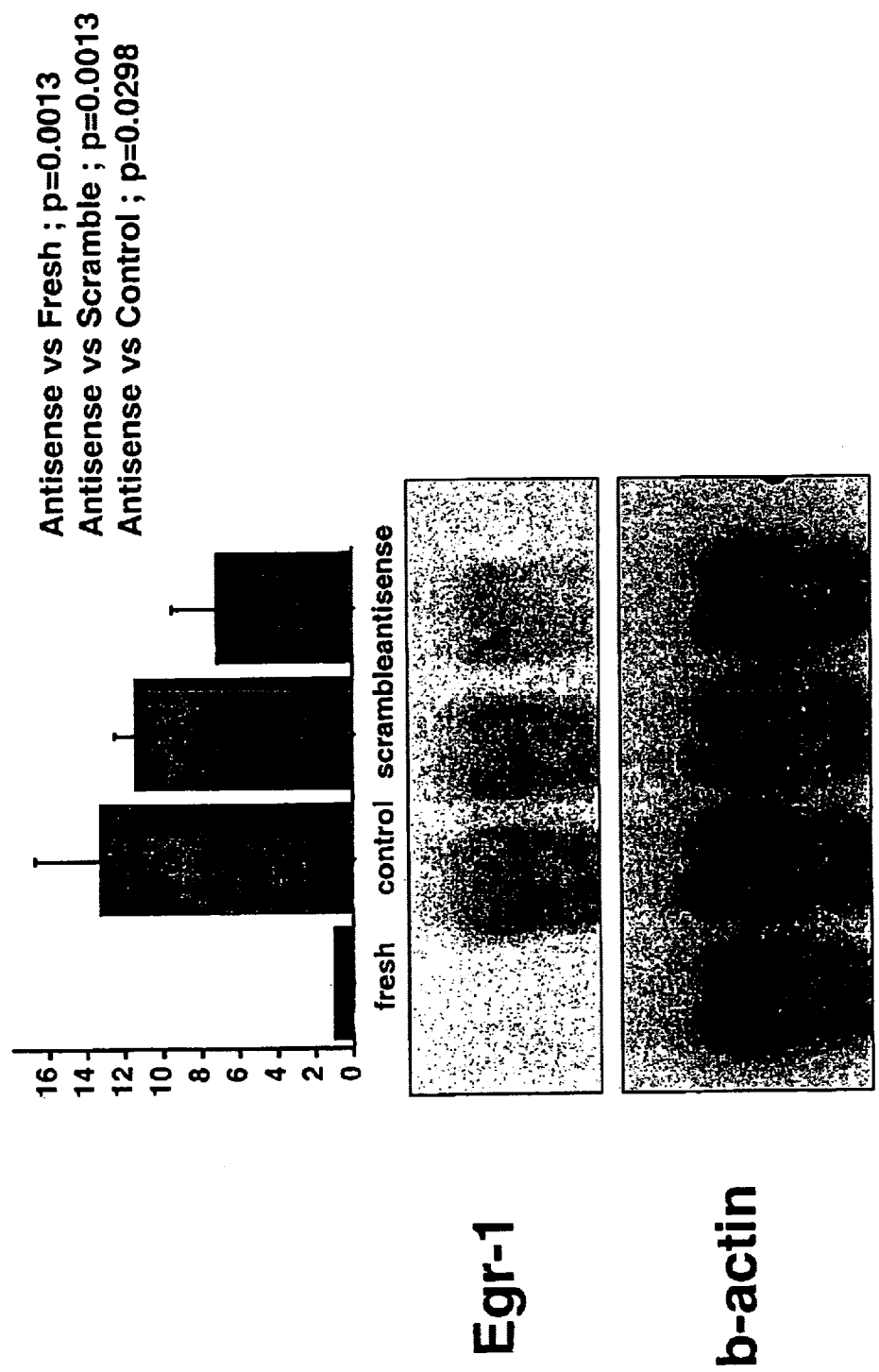
FIG. 10. Northern Blotting; Egr-1/b-actin. Effect of cationic liposomal carrier (control), scrambled sequence Egr-1 oligodeoxyribonucleotide, or antisense Egr-1 oligodeoxyribonucleotide on Egr-1 mRNA expression after lung transplantation. Fresh denotes nontransplanted lung tissue. Data are normalized to beta actin for control.
Figure 11:
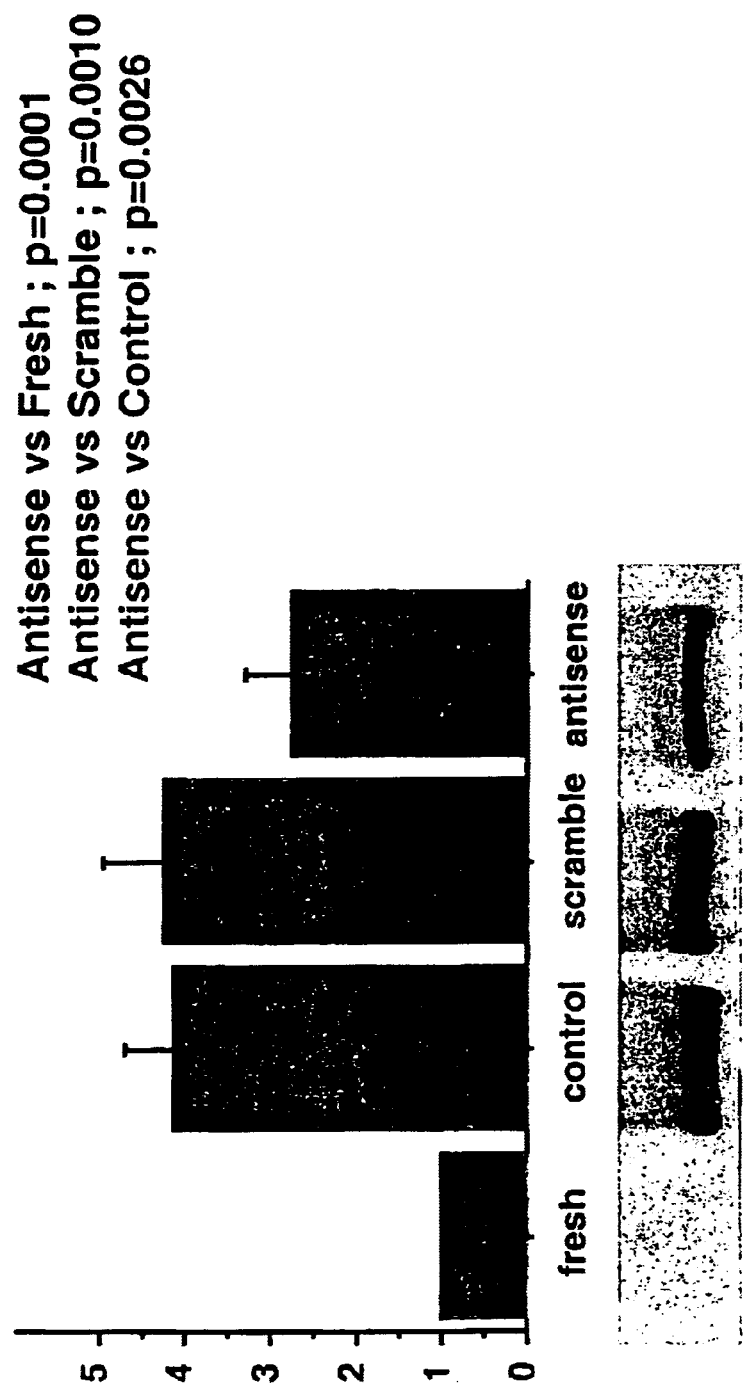
FIG. 11. Western Blotting; EGR-1. Effect of cationic liposomal carrier (control), scrambled sequence Egr-1 oligodeoxyribonucleotide, or antisense Egr-1 oligodeoxyribonucleotide on Egr-1 protein expression after lung transplantation. Fresh denotes nontransplanted lung tissue.
Figure 12:
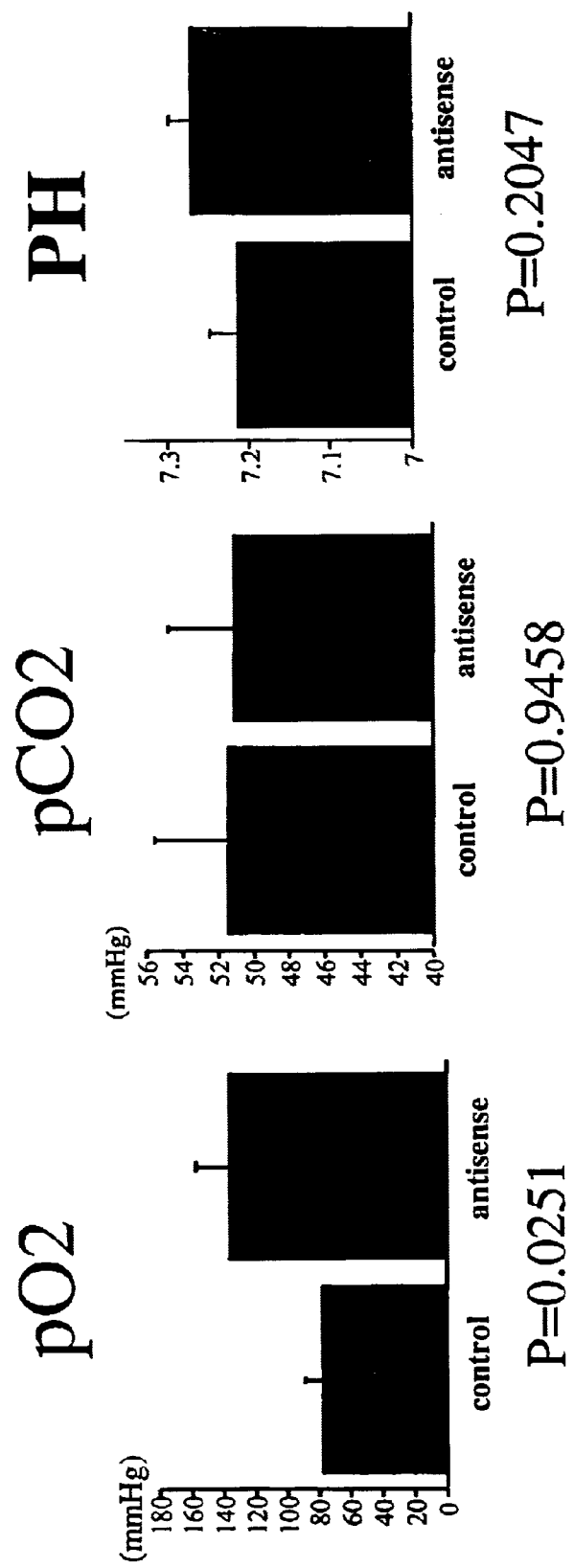
FIG. 12. Effect of control (carrier) or Egr-I antisense oligodeoxyribonucleotide on gas exchange following left lung transplantation and circulatory exclusion of the right (nontransplanted) lung.
Figure 13:
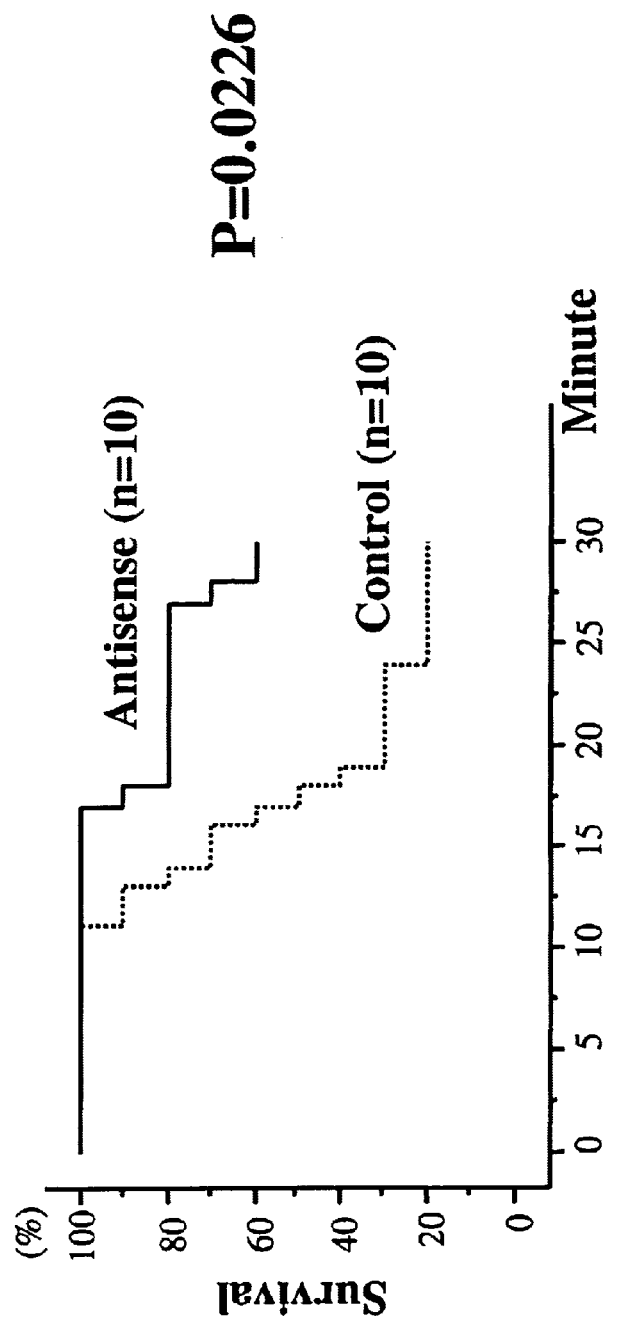
FIG. 13. Survival Rate. Effect of control (carrier) or Egr-1 antisense oligodeoxyribonucleotide on recipient survival following left lung transplantation and circulatory exclusion of the right (nontransplanted) lung.

In an orthotopic, isogeneic rat lung transplant model, Egr-1 expression was studied and the role of suppressing its expression evaluated. Although Egr-1 only increases slightly during hypotherriiic lung preservation, it increases briskly albeit briefly during reperfusion (FIG. 8, Northern blot showing a brisk rise in Egr-1 mRNA following lung reperfusion; FIG. 9, a western blot showing a brisk rise in Egr-1 protein following lung reperfusion). To detect the functional significance of this increase in Egr-1 mRNA and protein in the reperfused lungs, an antisense Egr-1 oligodeoxytibonucleotide was constructed and given into the blood vessels of the donor rat lung using a cationic liposomal carrier, as described in the Methods section. Control (cationic liposomal carrier alone) and a scrambled oligodeoxyribonucleotide (with the same nucleotides, but in random order as the antisense compound), were used to control for non-sequence specific effects of the carrier or the antisense Egr-1 oligodeoxyribonucleotide. The antisense compound reduced the expression of Egr-1 mRNA by nearly half (FIG. 10), and similarly reduced the amount of Egr-1 protein as detected by inimunoblotting (FIG. 11). When antisense compound was given to the donor rat prior to lung preservation, the function of the graft after transplantation (measured by arterial oxygenation in the recipient which depends entirely upon the transplanted lung) is improved only by the antisense Eg-1 oligodeoxyribonucleotide (FIG. 12). Survival of the recipient rat following lung transplantation is improved only by the the antisense Egr-1 oligodeoxyribonucleotide (FIG. 13). These data show that Egr-1 expression rises briskly during reperfusion of an ischemic tissue, and that suppressing its expression can have functionally beneficial and improve survival of the entire organism following an ischemic challenge. Because an isogeneic (identical strain) transplant model was used, these results are broadly applicable to ischemia in general, and not restricted just to the transplant setting.

Materials and Preparation of Antisense Egr-1 and Lung Transplant Model (Used in FIGS. 8–13):

Materials:

Preservation solution: For all transplant experiments, the basic preservation solution consisted of modified Euro-Collins solution obtained from Baxter Healthcare (Deerfield, Ill.; Na$^+$10 mEq/L, K$^+$11 5 mEq/L, C1-15 mEq/L, HPO$_4^2$-85 mEq/L, H$_2$PO$_4$-15 mEq/L, HCO$_3$-10 mEq/L), modified by adding 10 mL of 10% magnesium sulfate and 50 mL of 50% glucose solution per liter. This represents the standard formulation used in clinical lung transplantation.

Sense and antisense oligonucleotides: Sense and antisense phosphorothioate oligonucleotides were chemically synthesized and HPLC-purified (GIBCO BRL, Grand Island, N.Y.). Egr-1 antisense oligonucleotide was 5'-CTTGGCCGCTGCCAT-3'(SEQ ID NO:1). The complementary sense sequence used was 5'-TACCGTCGCCGTGCT-3' (SEQ ID NO:2). Cationic liposomal carrier: To transfect the oligonucleotides into cells or pulmonary grafts, a cationic liposomal carrier was used which has demonstrated efficacy and lack of toxicity[7] in pulmonary endothelial cells. The liposome formulation chosen for these experiments was the cationic lipid N-[1-(2, 3-dioleyloxy) propyl]-N,N,N-trimethylammonium chloride (DOTMA), and dioleoyl phosphotidylethanolamine (DOPE) (GIBCO BRL) to enhance the oligonucleotide uptake by cells.

Other Materials: Unless otherwise specified, chemicals were purchased from either Sigma Chemical Co. (St. Louis, Mo.) or Boerhinger Mannheim Co. (Indianapolis, Ind.)

Lung transplant experiments: Donor Lung Harvest: Inbred male Lewis rats (250–300 gms) were used for experiments. Donor rats were given 500 units of heparin intravenously, and following ligation of the right pulmonary artery (PA) (to restrict delivery of preservation solution to the donor lung used for grafting), 7 mL of 4° C. preservation solution was administered into the main PA at a constant infusion pressure of 20 mm Hg. The left lung was then harvested, a cuff was placed on each vascular stump and the left bronchus, and the lung was submerged for 4 hours in preservation solution maintained at 4° C. Transplantation was performed using gender/strain/size matched recipient rats which were anesthetized, intubated, and ventilated with 100% $O_2$ using a rodent ventilator. Orthotopic left lung transplantation was performed as described 9 through a left thoracotomy using a rapid cuff technique for all anastomoses, with warm ischemic times maintained below 5 minutes. The hilar cross-clamp was released, re-establishing blood flow and ventilation to the transplanted lung.

For all experiments, the preservation duration was 4 hours. For those experiments in which oligonucleotides were studied, the base preservation solution was supplemented with lipofectin (350 [Lg/0.8 mL of EuroCollins), which was allowed to equilibrate for 45 minutes at room temperature, followed by the addition of either the sense or the antisense oligonucleotide construct (350 μg in an additional 0.8 mL of EuroCollins); this 1.6 mL mixture was allowed to incubate at room temperature for 30 minutes, after which 5.4 mL of EuroCollins solution was added, and the entire mixture chilled to 4° C. This was prepared fresh for each experiment.

After lung transplantation, the right (nontransplanted lung was excluded from the circulation with a ligature, and the function of the left (transplanted) lung was measured. Gas exchange was determined by measuring arterial oxygen tension ($PO^2$, mm Hg). using a model ABL-30 gas analyzer from a sample of left atrial blood taken at the final time point at which the recipient was alive (up to 30 minutes). Thirty minutes following ligation of the native right PA, survival was assessed, and transplanted lung was cross-clamped to divide it into equal parts, with one portion being excised, rinsed briskly in physiologic saline, and snap frozen in liquid nitrogen until the time of assays for Egr-1 protein or MRNA expression.

Immunoblotting for Egr-I Protein: For the lung transplant experiments, integral membrane proteins were extracted. Lung tissue was homogenized in TBS buffer containing protease inhibitors, and protein concentrations were determined according to the Bradford method. Samples were prepared for nonreduced SDS-PAGE, with equal amounts of protein (20 μg) loaded onto on 7.5% Tris-Glycine gel, subjected to electrophoresis, and electrophoretically transferred onto a nitrocellulose membrane. After overnight blocking with nonfat dry milk, the membrane was incubated for 3 hours at room temperature with a 1:1000 dilution (in nonfat dry milk) of anti-Egr-1 IgG, washed thrice, followed by a 1 hour room temperature incubation with a 1:1000 dilution of a horseradish peroxidase-conjugated secondary IgG. Sites of primary antibody binding were visualized by the enhanced chemiluminescence method (for the cell culture experiments) in which blots were developed with Diaminobenzidine in Tris buffer (50 mM). Blots were scanned into a Macintosh computer for subsequent densitometric analysis.

Northern blotting for Egr-1 mRNA: For analysis of Egr-1 mRNA, total cellular RNA was extracted using an RNA isolation kit. To detect Egr-1 mRNA, equal amounts of RNA (20 μg) were loaded onto a 0.8%. agarose gel containing 2.2 M formaldehyde for size fractionation, and then transferred overnight by capillary pressure to nylon membranes with 2OX SSC buffer (GIBCO BRL). An Egr-1 cDNA probe was labelled with $\alpha$-$^{32}$P-dCTP by random primer labelling, hybridized to blots at 68° C. for 1 hour in hybridization solution, washed twice with 2X SSC/0.1% SDS for 15 minutes at room temperature, and once with 0. 1X SSC/ 0.1% SDS for 30 minutes at 60° C. Blots were developed with X-Omat AR film exposed with an intensifying light screen at −70° for 3 to 7 days. Membranes were subsequently stripped to reprobe for β-actin by boiling in 0.1X SSC/0.1% SDS; the membrane was then hybridized with a β-actin cDNA probe (and developed as described above). Blots were scanned into a Macintosh computer, and Molecular Analysis software used to calculate the density of each band.

Sequences: The following are several Egr-1 nucleic acid and protein sequences which are available in GenBank.
LOCUS HSA243425 6590 bp
DNA PRI 03-JUL-2000
DEFINITION Homo sapiens EGR1 gene for early growth response protein 1.
ACCESSION AJ243425VERSION AJ243425.1 GI:5420378
KEYWORDS early growth response protein 1; EGR1 gene.
SOURCE human.
ORGANISM Homo sapiens Eukaryota; Metazoa; Chordata; Craniata; Vertebrata; Euteleostomi; Mammalia; Eutheria; Primates; Catarrhini; Homninidae; Homo.
REFERENCE 1 (bases 1 to 6590)
AUTHORS Slade, J. P. and Carter, D. A.
TITLE Cyclical expression of egr-1/NGFI-A in the rat anterior pituitary: A molecular signal for ovulation?
JOURNAL J. Neuroendocrinol. 12 (7), 671–676 (2000)
MEDLINE 20307414
REFERENCE 2 (bases 1 to 6590)
AUTHORS Slade, J. P.
TITLE Direct Submission
JOURNAL Submitted (25-JUN-1999) Slade J. P., School of Biosciences, Cardiff University, PO BOX 911, Museum Avenue, Cardiff, CF1 3US, UNITED KINGDOM
FEATURES Location/Qualifiers source 1..6590/organism= "Homo sapiens"/db_xref="taxon:9606" /clone="ATCC 65848" mRNA join(2370..2957,3644..6198)/gene= "EGR1"/product="early growth response protein 1" exon 2370..2957/gene="EGR1" /number=1 gene 2370..6198/ gene="EGR1" 5'UTR 2370 . . . 2650/gene="EGR1" CDS join(2651..2957,3644..968)/gene="EGR1"/codon_start= 1/product="early growth response protein 1"/protein_id= "CAB46678.1"/db_xref="GI:5420379"
/translation=
MAAAKAEMQLMSPLQISDPFGSFPHSPT-MDNYPKLEEMMLLSNG APQFLGAAGAPEGSG-SNSSSSSSGGGGGGGGGSNSSSSSSTFNPQADTGEQ PYEHLTA ESFPDISLNNEKVLVETSYPSQTTRLP-
PITYTGRFSLEPAPNSGNTLWPEPLFSLVSG LVSMT-
NPPASSSSAPSPAASSASASQSP-
PLSCAVPSNDSSPIYSAAPTFPTPNTDIFP
EPQSQAFPGSAGTALQYPPPAYPAAKGG-
FQVPMIPDYLFPQQQGDLGLGTPDQKPFQG LES-
RTQQPSLTPLSTIKAFATQSGSQDL-
KALNTSYQSQLIKPSRMRKYPNRPSKTPPH
ERPYACPVESCDRRFSRSDELTRHIR-
IHTGQKPFQCRICMRNFSRSDHLTTHIRTHTG EKP-
FACDICGRKFARSDERKRHTKIHLRQKD-
KKADKSVVASSATSSLSSYPSPVATSY
PSPVTTSYPSPATTSYPSPVPTSF-
SSPGSSTYPSPVHSGFPSPSVATTYSSVPPAFPA
QVSSFPSSAVTNSFSASTGLSDMTATFSPRTIEIC
(SEQ ID NO:3)
intron 2958..3643/gene="EGR1"/number=exon 3644..6198/
gene="EGR1"/number=2 3'UTR 4969..6177/gene=
"EGR1" polyA_signal 6178..6183/gene="EGR1"
BASE COUNT 1351 a 2048 c 1784 g 1407 t
ORIGIN
1 gcgggctggg gctgtggctc acacctggaa tcccagcact ttgggaggcc
gaagtgggtg
61 aatcgcttga gctcaagagt tcaagaccag cctgggcaac acagcgaaac
ccctctctac
121 gaaaatacaa aaaaaaaaa aaaagtaa aagccaggcg tggtggcagg
cacctgtagt
181 ccaagctact cgagaggagg aggctggagg atcacttgag cctgg-
gaggc ggaggttgca
241 gtgagctcgc gccactgcac tccaacctgg gtgccagcgt gagac-
cccgt ctcagaaaga
301 ataaaaacat taaaaaaaa atttggctaa ggtaccctac cagggagtgg
caaaatggac
361 attcagacac aaggccatct gcgctgcaac agcctggcct tcctgcccct
gcggcaggag
421 tcctctgaga ggcgcatcac tcctgcccca atggacaact ccgtagacag
tgggagtgag
481 ccccccacct cccccagcgga cttgagacgg caggctccga gacgagg-
gag tcctggttca
541 ttaagttggt ttttataaaa aaacatgttt ggaggggga cagccacaaa
gggattaagt
601 ccaagaaagt taccccctcc cccacctaat cccctgacc ccgacctca
gaggctgttg
661 gggtttacag aggccctcac ctcctcctt ccctctcggt gtcgtcaaac
accctcttc
721 tccacattc tctttctgct ttcttttaa atccagaaaa aacagtacct
cctctggatt
781 cagagctaga gcaggaggag ccttccttcc cggaatccct gttccctttg
ggggagcaac
841 tgacggttcg tggggcggg gagggttccc cttttgttt gacccaagga
agactgggga
901 atattttcct tagacaccac ccacccctt ttcttttcc ccttcacttt gccag-
gctgg
961 ggttgaggat tgtatccccg gagtttgggc gcttcggaag tgacggttcc
ccggggtttg
1021 aaggggagcc cgggttaagc gcctgttcag ttcgtgctca tgcgtc-
gaag gctccccgg
1081 ccttgctccg cgcccagcgc cgcatccggg aggaggagcg aggag-
gcggc ggaagagccc
1141 gcgcggccgg agtccggggc tgggagtgga gagggaacct
ccaggggca gcaccgagcc
1201 gcaaagccgg tcctctcttc gcgcccagcc cggggtcccc agatagc-
cca taggaagcc
1261 cctctttcgg attcccgcag tgtgggccgg ccctccacct ggactggata
aaggggggaa
1321 agtgacccct caccacaagg accattatct cctggtgaga acaa-
gaatca ggcctctctt 1381 ggggcaatca gcttccccac ttcggtcccc caaaggtggg
ctctttgccg gcggggacta
1441 gggaacagcc tcggttcc gggggagcac aggggacccc aggcac-
cagc agccccatcc
1501 caccgacagg tggcagaggc aaggcagctc actgctatac agtgtc-
ccaa gaaccaagtg
1561 gccgtgactt cctatcctca atttcccage gacacccgga aagacac-
cgt gccatagatc
1621 gaggcccggg gtcaaggccc cgcctctcct gggcggcccc tgc-
ccaggcg ggcccagccg
1681 ctcctccccc gcactcccgg ttcgctctca cggtccctga
ggtgggcggg cgggcctgga
1741 tgacagcgat agaaccccgg cccgactcgc cctcgccccc
gctctgggtc tgggcttccc
1801 cagcctagtt cacgcctagg agccgcctga gcagccgcgc
ccagcgccac acgccacgag
1861 ccctccccgc ctgggcgtcc ccggatcccg cgagcgctcg ggctc-
ccgcc ttggaaccag
1921 ggaggaggga gggagcgagg gagcaaccag ctcggaccgg aat-
gcatata gagcaggaag
1981 gatcccccgc cggaacaacc cttatttggg cagcaccta tttggagtgg
cccgatatgg
2041 cccggcgctt ccggctctgg gaggagggaa aaggcggag
ggaggggcaa cgcgggaact
2101 ccggagctgc cggtcccgga ggccccggcg gcggctagag ctctag-
gctt ccccgaagct
2161 ccggcgctgg gatgcgggcc gggccgggcc ctagggtgca ggatg-
gaggt gccgggcgct
2221 gtcggatggg gggcttcacg tcactccggg tcctccccg gtcctgc-
cat attagggctt
2281 ctgcttccca tatatgccat gtacgtcacg acggaggcgg acccgt-
gccg ttccagaccc
2341 ttcaaataga ggcggatccg gggagtcgcg agagatccag ccgca-
gaact tggggagccg
2401 ccgccgccat ccgccgccgc agccagcttc gccgccgca ggac-
cggccc ctgccccagc
2461 ctccgcagcc gcggcgcgtc cacgcccgcc cgcgcccagg
gcgagtcggg gtcgccgcct
2521 gcacgcttcc cagtgttccc cgcgccccgc atgtaacccg gccaggc-
ccc cgcaacggtg
2581 tcccctgcag ctccagcccc gggctgcacc ccccgcccc gacac-
cagct ctccagcctg
2641 ctcgtccagg atggccgcgg ccaaggccga gatgcagctg atgtc-
cccgc tgcagatctc
2701 tgacccgttc ggatcctttc ctcactcgcc caccatggac aactacccta
agctggagga
2761 gatgatgctg ctgagcaacg gggctcccca gttcctcggc gccgc-
cgggg ccccagaggg
2821 cagcggcagc aacagcagca gcagcagcag cggggcggt ggag-
gcggcg ggggcggcag
2881 caacagcagc agcagcagca gcaccttcaa ccctcaggcg
gacacgggcg agcagcccta
2941 cgagcacctg accgcaggta agcagtggcc tacgccgagg
gggaaccctt tcgccaccat
3001 cctggcgtcc tgtccttcac cgcaggagtg ctcctggatc ttagaatgag
agccgggttt
3061 cccttttcatt cctcgcatcc ccagagtcat gtgttagagg gatgccaagg
aaccccacac
3121 agcccacccc ctgccctcat ccctagcgga gcgcagagga
ccgagctttt gttttggatg
3181 gagagctctg gagctgcgtg ggtgggtgga gggggagggc
ttgttttgat gagcggggct
3241 gcgccccac ctccagtaag acttgccttg ccttgcttgc cgcctgtccc
caaggaagga
3301 ccgtgatcct tggccgtgga tgtcccggca gcccgggttt
ggggcgcgc actagccgcg
3361 gccatggggg tgctggcggg aatccctcgc ccgcacagcc gccgct-
gcgg agcgctgcga 3421 gctgcagtgg aggggattc tcgtatttg cgtcactgtt gttgaaatgg gctctgccac
3481 tggtgcgggt ccaggaacat tgcaatgtgc tgctatcaat tattaactac ctcgggagtc
3541 aatggtagcc ggcccggtct cttgcctggc agctcgggtc gtc-ctcgtcc tccagtgatt
3601 gttttccagt aaccaggcct cccgcttctc tctctcctgc cagagtcttt tcctgacatc
3661 tctctgaaca acgagaaggt gctggtggag accagttacc ccagccaaac cactcgactg
3721 cccccatca cctatactgg ccgcttttcc ctggagcctg cacccaacag tggcaacacc
3781 ttgtggcccg agccctctt cagcttggtc agtggcctag tgagcatgac caacccaccg
3841 gcctcctcgt cctcagcacc atctccagcg gcctcctccg cctccgcctc ccagagccca
3901 cccctgagct gcgcagtgcc atcaacgac agcagtccca tttact-cagc ggcacccacc
3961 ttccccacgc cgaacactga cattttccct gagccacaaa gccaggcctt cccggggctcg
4021 gcagggacag cgctccagta cccgcctcct gcctaccctg ccgc-caaggg tggcttccag
4081 gttccatga tccccgacta cctgtttcca cagcagcagg gggatctggg cctgggcacc
4141 ccagaccaga agcccttcca gggcctggag agccgcaccc agcagc-cttc gctaaccct
4201 ctgtctacta ttaaggcctt tgccactcag tcgggctccc aggacctgaa ggccctcaat
4261 accagctacc agtcccagct catcaaaccc agccgcatgc gcaag-tatcc caaccggcc
4321 agcaagacgc cccccacga acgcccttac gcttgcccag tggagtc-ctg tgatcgccgc
4381 ttctcccgct ccgacgagct cacccgccac atccgcatcc acacag-gcca gaagcccttc
4441 cagtgccgca tctgcatgcg caacttcagc cgcagcgacc acctcac-cac ccacatccgc
4501 acccacacag gcgaaaagcc cttcgcctgc gacatctgtg gaa-gaaagtt tgccaggagc
4561 gatgaacgca agaggcatac caagatccac ttgcggcaga agga-caagaa agcagacaaa
4621 agtgttgtgg cctctccggc cacctcctct ctctcttcct acccgtcccc ggttgctacc
4681 tcttacccgt ccccggttac tacctcttat ccatcccgg ccaccaccc atacccatcc
4741 cctgtgccca cctccttctc ctctcccggc tcctcgacct acccatcccc tgtgcaragt
4801 ggcttcccct cccgtcggt ggccaccacg tactcctctg ttccccctgc mcccggcc
4861 caggtcagca gcttccctc ctcagctgtc accaactcct tcagcgcctc cacagggctt
4921 tcggacatga cagcaaccctt ttctcccagg acaattgaaa tttgctaaag ggaaagggga
4981 aagaagggaa aagggagaa aagaaacac aagagactta aaggacagga ggaggagatg
5041 gccataggag aggaggggttc ctcttaggtc agatggaggt tctca-gagcc aagtcctccc
5101 tctctactgg agtggaaggt ctattggcca acaatccttt ctgcccactt cccttcccc
5161 aattactatt cccttttgact tcagctgcct gaaacagcca tgtccaagtt cttcacctct
5221 atccaaagaa cttgatttgc atggattttg gataaatcat ttcagtatca tctccatcat
5281 atgcctgacc ccttgctccc ttcaatgcta gaaaatcgag ttggcaaaat gggggtttggg
5341 cccctcagag ccctgccctg caccttgta cagtgtctgt gccatggatt tcgttctc
5401 tggggtactc ttgatgtgaa gataaatttgc atattctatt gtattatttg gagttaggtc
5461 ctcacttggg ggaaaaaaaa aaaaaaaagc caagcaaacc aatggtgatc ctctatttg
5521 tgatgatgct gtgacaataa gtttgaacct tttttttga aacagcagtc ccagtattct
5581 cagagcatgt gtcagagtgt tgttccgtta acctttttgt aaatactgct tgaccgtact
5641 ctcacatgtg gcaaaatatg gtttggtttt tctttttttt ttttgaaagt gtttttttctt
5701 cgtccttttg gtttaaaaag tttcacgtct tggtgccttt tgtgtgatgc cccttgctga
5761 tggcttgaca tgtgcaattg tgagggacat gctcacctct agccttaagg ggggcaggga
5821 gtgatgattt gggggaggct ttgggagcaa aataaggaag agggct-gagc tgagcttcgg
5881 ttctccagaa tgtaagaaaa caaatctaa aacaaaatct gaactctcaa aagtctattt
5941 ttttaactga aaatgtaaat ttataaatat attcaggagt tggaatgttg tagttaccta
6001 ctgagtaggc ggcgattttt gtatgttatg aacatgcagt tcattatttt gtggttctat
6061 tttactttgt acttgtgttt gcttaaacaa agtgactgtt tggcttataa aca-cattgaa
6121 tgcgctttat tgcccatggg atatgtggtg tatatccttc caaaaaatta aaacgaaaat
6181 aaagtagctg cgattgggta tgtgtttcct gggttagggg aaggactctg ccctattgag
6241 ggctgtgagg ttttctgaag acttggcctt tagagataca aggatcctcc agccagagtc
6301 aggcccactg tgtgaaactg gagttcgtta tttatgagga ctgagtatgg gtcttcaaat
6361 agggtctcgg tctatccacc caggctggag tgcagtagtg taatca-cagt tcactgcagc
6421 tttggtgtct caggctcaag tgatcctccc acctcagcct cctgagtagc tgggactata
6481 ggcacgtgcc accacactcg gttaatgttt atagagacag ggttttgcca tgttgcccag
6541 gctggagttc ttcttgataa tgggcctgtt cctcttcagt ctgttgggtg // (SEQ ID NO:4)

LOCUS NM_001964 3132 bp mRNA PRI 07-APR-2000
DEFINITION Homo sapiens early growth response 1 (EGR1), mRNA.
ACCESSION NM_001964
VERSION NM 001964.1 GI:4503492
KEYWORDS.
SOURCE human.
ORGANISM Homo sapiens Eukaryota; Metazoa; Chordata; Craniata; *Vertebrata*; Euteleostomi; Mammalia; Eutheria; Primates; CatarThini; Hominidae; *Homo*.
REFERENCE 1 (bases 1 to 3132)
AUTHORS Suggs, S. V., Katzowitz, J. L., Tsai-Morris, C. and Sukhatme,V. P.
TITLE cDNA sequence of the human cellular early growth response gene Egr-1
JOURNAL Nucleic Acids Res. 18 (14), 4283 (1990)
MEDLINE 90332455
REFERENCE 2 (bases 1 to 3132)
AUTHORS Mahlknecht U, Bucala R. Hoelzer D and Verdin E.
TITLE High resolution physical mapping of human HDAC3, a potential tumor suppressor gene in the 5q31 region
JOURNAL Cytogenet. Cell Genet. 86 (34), 237–239 (1999)
MEDLINE 20044614
PUBMED 10575214
COMMENT REFSEQ: The reference sequence was derived from X52541.1. PROVISIONAL RefSeq: This is a provisional reference sequence record that has not yet been subject to human review. The final curated reference sequence record may be somewhat different from this one.
FEATURES Location/Qualifiers source 1..3132/organism= "Homo sapiens"/db_xref="taxon:9606"/chromosome= "5"/map=5q31.1"/clone="hEGR1.364"/cell_type= "fibroblast 303"/tissue_type="foreskin"/clone_lib= "lambda-ZAP" gene 1..3132/gene="EGR1"/note= "KROX-24; NGFI-A; TIS8; ZIF-268"/db_xref= "LocusID:958"/db_xref="MIM:128990" CDS 271..1902/gene ="EGR1"/codon_start=1/product="early growth response 1"/protein_id="NP_001955.1"/db_xref="GI:4503493"
/translation=
"MAAAKAEMQLMSPLQISDPFGSFPHSPT-MDNYPKLEEMMLLSNG APQFLGAAGAPEGSG-SNSSSSSSGGGGGGGGGSNSSSSSSTFNPQADTGEQPYEHLTA-ESFPDISLNNEKVLVETSYPSQTTRLP-PITYTGRFSLEPAPNSGNTLWPEPLFSLVSG LVSMT-NPPASSSSAPSPAASSASASQSP-PLSCAVPSNDSSPIYSAAPTFPTPNTDIFP EPQSQAFPGSAGTALQYPPPAYPAAKGG-FQVPMIPDYLFPQQQGDLGLGTPDQKPFQG LES-RTQQPSLTPLSTIKAFATQSGSQDL-KALNTSYQSQLIKPSRMRKYPNRPSKTPPH ERPYACPVESCDRRFSRSDELTRHIR-IHTGQKPFQCRICMRNFSRSDHLTTHIRTHTG EKP-FACDICGRKFARSDERKRHTKIHLRQKD-KKADKSVVASSATSSLSSYPSPVATSY PSPVTTSYPSPATTSYPSPVPTSF-SSPGSSTYPSPVHSGFPSPSVATTYSSVPPAFPA QVSSFPSSAVTNSFSASTGLSDMTATFSPRTIEIC" (SEQ ID NO:5)
polyA_site 3132/note="polyadenylation site"
BASE COUNT 687 a 1004 c 730 g 711 t
ORIGIN 1 ccgcagaact tggggagccg ccgccgccat ccgccgccgc agccagcttc cgccgccgca 61 ggaccggccc ctgccccagc ctccgcagcc gcggcgcgtc cacgccgcc cgcgcccagg 121 gcgagtcggg gtcgccgcct gcacgcttct cagtgttccc cgcgcccgc atgtaacccg 181 gccaggcccc cgcaacggtg tccctgcag ctccagcccc gggctgcacc cccccgcccc 241 gacaccagct ctcagcctg ctcgtccagg atggccgcgg ccaaggccga gatgcagctg 301 atgtccccgc tgcagatctc tgacccgttc ggatcctttc ctcactcgcc caccatggac 361 aactacccta agctggagga gatgatgctg ctgagcaacg gggctcccca gttcctcggc 421 gccgccgggg ccccagaggg cagcggcagc aacagcagca gcagcagcag cggggcggt 481 ggaggcggcg ggggcggcag caacagcagc agcagcagca gcaccttcaa ccctcaggcg 541 gacacgggcg agcagcccta cgagcacctg accgcagagt cttttctga catctctctg 601 aacaacgaga aggtgctggt ggagaccagt tacccccagc caaaccactcg actgccccc 661 atcacctata ctggccgctt ttccctggag cctgcaccca acagtggcaa caccttgtgg 721 cccgagcccc tcttcagctt ggtcagtggc ctagtgagca tgaccaaccc accggcctcc 781 tcgtcctcag caccatctcc agcggcctcc tccgcctccg cctcccagag cccacccctg 841 agctgcgcag tgccatccaa cgacagcagt cccatttact cagcggcacc caccttccc 901 acgccgaaca ctgacatttt ccctgagcca caaagccagg ccttcccggg ctcggcaggg 961 acagcgctcc agtacccgcc tcctgcctac cctgcrgcca agggtggctt ccaggttccc 1021 atgatccccg actacctgtt tccacagcag caggggatc tgggcctggg cacccagac 1081 cagaagcct tccagggcct ggagagccgc acccagcagc cttcgctaac ccctctgtct 1141 actattaagg cctttgccac tcagtcgggc tcccaggacc tgaaggccct caataccagc 1201 taccagtccc agctcatcaa acccagccgc atgcgcaagt atccaaccg gcccagcaag 1261 acgcccccc acgaacgccc ttacgcttgc ccagtggagt cctgtgatcg ccgcttctcc 1321 cgctccgacg agctcacccg ccacatccgc atccacacag gccagaagcc cttccagtgc 1381 cgcatctgca tgcgcaactt cagccgcagc gaccacctca ccacccacat ccgcacccac 1441 acaggcgaaa agcccttcgc ctgcgacatc tgtggaagaa agtttgccag gagcgatgaa 1501 cgcaagaggc ataccaagat ccacttgcgg cagaaggaca gaaagcaga caaaagtgtt 1561 gtggccictt cggccacctc ctctctctct tcctacccgt ccccggttgc tacctcttac 1621 ccgtccccgg ttactacctc ttatccatcc ccggccacca cctcataccc atccctgtg 1681 cccacctcct tctcctctcc cggctcctcg acctacccat ccctgtgca cagtggcttc 1741 ccctcccgt cggtggccac cacgtactcc tctgttcccc ctgctttccc ggcccaggtc 1801 agcagcttcc cttcctcagc tgtcaccaac tccttcagcg cctccacagg gctttcggac 1861 atgacagcaa ccttttctcc caggacaatt gaaatttgct aaagggaaag gggaaagaaa 1921 gggaaaggg agaaaaagaa acacaagaga cttaaaggac aggaggagga gatggccata 1981 ggagaggagg gttcctctta ggtcagatgg aggttctcag agccaagtcc tccctctcta 2041 ctggagtgga aggtctattg gccaacaatc ctttctgccc acttcccctt ccccaattac 2101 tattcccttt gacttcagct gcctgaaaca gccatgtcca agttcttcac ctctatccaa 2161 agaacttgat ttgcatggat tttggataaa tcatttcagt atcatctcca tcatatgcct 2221 gacccccttgc tcccttcaat gctagaaaat cgagttggca aaatgggggtt tgggcccctc 2281 agagccctgc cctgraccct tgtacagtgt ctgtgccatg gatttcgttt ttcttgggt 2341 actcttgatg tgaagataat ttgcatattc tattgtatta tttggagtta ggtcctcact 2401 tgggggaaaa aaaaaaaaaa aagccaagca aaccaatggt gatcctctat tttgtgatga 2461 tgctgtgaca ataagtttga accttttttt ttgaaacagc agtcccagta ttctcagagc 2521 atgtgtcaga gtgttgttcc gttaaccttt ttgtaaatac tgcttgaccg tactctcaca 2581 tgtggcaaaa tatggtttgg ttttctttt ttttttga aagtgttttt tctctcgtcct 2641 tttggtttaa aaagtttcac gtcttggtgc cttttgtgtg atgccccttg ctgatggctt 2701 gacatgtgca attgtgaggg acatgctcac ctctagcctt aaggggggca gggagtgatg 2761 atttggggga ggctttggga gcaaaataag gaagagggct gagct gagct tcggttctcc 2821 agaatgtaag aaaacaaaat ctaaaacaaa atctgaactc tcaaaagtct attttttaa 2881 ctgaaaatgt aaatttataa atatattcag gagttggaat gttgtagtta cctactgagt 2941 aggcggcgat ttttgtatgt tatgaacatg cagttcatta ttttgtggtt ctattttact 3001 ttgtacttgt gtttgcttaa acaaagtgac tgtttggctt ataaacacat tgaatgcgct
3061 ttattgccca tgggatatgt ggtgtatatc cttccaaaaa affaaaacga aaataaagta
3121 gctgcgattg gg (SEQ ID NO:6)

References

1. Mirandt, J. A nerve growth factor induced gene encodes a possible transcriptional regulatory factor. Science 238, 797–799 (1988).
2. Gashler, A. & Sukhatme, V. Egr-1: prototype of a zinc finger fan-lily of transcription factors. Prog. Nucl. Acids Res. and Molec. Biol. 50, 191–224 (1995).
3. Nguyen, H., Hoffman-Lieberman, B. & Liebennann, D. Egr-1 is essential for and restricts differentiation along the macrophage cell lineage. Cell 72, 197–209 (1993).
4. Semenza, G. Perspectives on oxygen sensing. Cell 98, 281–284 (1999).
5. Zhu, H. & Bunn, H. Oxygen sensing and signaling: impact on the regulation of physiologically important genes. Respir Physiol 115, 239–247 (1999).
6. Ratcliffe, P., O'Rourke, J., Maxwell, P. & Pugh, C. Oxygen sensing, HIF-1 and the regulation of mammalian gene expression. J. Exp. Biol. 201, 1153–1162 (1998).
7. Yan, S-F., et al. Tissue factor transcription driven by Egr-1 is a critical mechanism of murine pulmonary fibrin deposition in hypoxia. Proc Natl Acad Sci 95, 8298–8303 (1998).
8. Yan, S-F., et al. Hypoxia-associated induction of Early Growth Response-1 gene expression. J Biol Chem 274, 15030–15040 (1999).
9. Lee, S., et al. Luteinizing hormone deficiency and female infertility in mice lacking the transcription factor NGFI-A (Egr-1). Science 273, 1219–1221 (1996).
10. Okada, K., et al. Potentiation of endogenous fibrinolysis and rescue from lung ischemia-reperfusion injury in IL-10-reconstituted IL-10 null mice. J. Biol. Chem. epub ahead of print (2000).
11. Collen, D. & Lijnen, H. Fibrin-specific fibrinolysis. Ann N Y Acad Sci 667, 259–271 (1992).
12. Loskutoff, D., Sawdey, M., Keeton, M. & Schneiderman, J. Regulation of PAI-1 gene expression in vivo. Thromb & Haemost 70, 135–137 (1993).
13. Leung, D., et al. VEGF is a secreted angiogenic mitogen. Science 246, 1306–1309 (1989).
14. Dvorak, H., Brown, L., Detmar, M. & Dvorak, A. VPF/VEGF, microvascular hyperpermeability, and angiogenesis. Am J Pathol 146, 1029–1039 (1995).
15. Hayashi, T., Abe, K., Suzuki, H. & Itoyama, Y. Rapid induction of VEGF gene expression after transient middle cerebral artery occlusion in rats. Stroke 28, 2039–2044 (1997).
16. Lee, S., et al. Early expression of angiogenesis factors in acute myocardial ischemia. New Engl J Med 342, 626–633 (2000).
17. VanBruggen, N., et al. VEGF antagonism reduces edema formation and tissue damage in ischemia/reperfusion injury in the mouse brain. J Clin Invest 104, 1613–1620 (1999).
18. Lefer, A. Role of the β2-integrins and immunoglobulin superfamily members in myocardial ischemia-reperfusion. Ann Thorac Surg 68, 1920–1930 (1999).
19. Wang. C., et al. Cardiac graft ICAM-1 and IL-1 expression mediate primary isograft failure and induction of ICAM-1 in organs remote from the site of transplantation. Circ Res 82, 762–772, (1998).
20. Lemay, S., Rabb, H., Postler, G. & Singh, A. Prominent and sustained upregulation of gpl30-signaling cytokines and the chemokine MIP-2 in murine renal ischemia-reperfusion injury. Transplant 69, 959–963 (2000).
21. Liu, P., et al. Role of endogenous nitric oxide in TNF-α and IL-1β generation in hepatic ischemia-reperfusion. Shock 13, 217–223 (2000).
22. Touzani, O., Boutin, H., Chuquet, J. & Rothwell, N. Potential mechanisms of IL-1 involvement in cerebral ischemia. J Neuroimmunol 100, 203–215 (1999).
23. Mitsui, Y. The expression of proinflammatory cytokine mRNA in the sciatic-tibial nerve of ischemia-reperfusion injury. Brain Res 844, 192–195 (1999).
24. Rollins, B. Chemokines. Blood 90, 909–928 (1997).
25. Kunkel, S. Through the looking glass: the diverse in vivo activities of chemokines. J Clin Invest 104, 1333–1334 (1999).
26. Colletti, L., Green, M., Burdick, M., Strieter, R. The ratio of ELR+ to ELR− CXC chemokines affects the lung and liver injury following hepatic ischemia/reperfusion in the rat. Hepatology 31, 435–445 (2000).
27. Yoshidome, H., Kato, A., Edwards, M. & Lentsch, A. IL-10 inhibits pulmonary NF-KB activation and lung injury by hepatic ischemia-reperfusion. Am J Physiol 277, L919–L923 (1999).
28. Lentsch, A., et al. Chemokine involvement in hepatic ischemia/reperfusion injury in mice: roles for MIP-2 and KC. Hepatology 27, 1172–1177 (1998).
29. Bless, N., et al. Roles for C-X-C chemokines and C5a in lung injury after hindlimb ischemia-reperfusion. Am J Physiol 276, L57–L63 (1999).
30. Gourmala, N., et al. Differential and time-dependent expression of JE/MCP-1 MRNA by astrocytes and macrophages in rat brain: effects of ischemia and peripheral LPS administration. J Neuroimmunol 74, 35–44 (1997).
31. Wang, X., et al. Prolonged expression of IP-10 in ischemic cortex after permanent occlusion of the middle cerebral artery in rat. J Neurochem 71, 1194–1204 (1998).
32. Brand, T., et al. Proto-oncogene expression in porcine myocardium subjected to ischemia and reperfusion. Circ Res 71, 1351–1360 (1992).
33. Ouellette, A., Malt, R., Sukhatme, V., Bonventre, J. Expression of two "immediate early" genes, Egr-1 and c-fos, in response to renal ischemia and during compensatory renal hypertrophy in mice. J Clin Invest 85, 766–771 (1990).
34. Safirstein, R., Price, P., Saggi, S., Har-fis, R. Changes in gene expression after temporary renal ischemia. Kidney Intl 37, 1515–1521 (1990).
35. Weiss, S. Tissue destruction by neutrophils. New Engl J Med 320, 365–376 (1989).
36. Pober, J., & Cotran, R. Cytokines and endothelial cell biology. Physiol. Revs. 70,427–451 1990).
37. Schechter, A., et al. Tissue factor is induced by MCP-1 in human aortic smooth muscle and THP-1 cells. J Biol Chem 272, 28568–28573 (1997).
38. Clauss, M., et al. VEGF: a tumor-derived polypeptide that induces endothelial cell and monocyte procoagulant activity, and promotes monocyte migration. J Exp Med 172, 1535–1545 (1990).
39. Maltzman, J., Carmen, J., Monroe, J. Transcriptional regulation of the ICAM-1 gene in antigen receptor- and phorbol ester-stimulated B lymphocytes: role for transcription factor Egr-1. J Exp Med 183,1747–1759 (1996).
40. Forsythe, J., et al. Activation of VEGF gene transcription by HIF-1. Molec Cell Biol 16, 4604–4613 (1996).
41. Mechtcheriakova, D., et al. VEGF-induced tissue factor expression in endothelial cells is mediated by Egr-1. Blood 93, 3 811–3123 (1999).

42. Khachigian, L., Lindner, V., Williams, A. & Collins, T. Egr-1-induced endothelial gene expression: a common theme in vascular injury. Science 271, 1427–1431 (1996).
43. Svaren, J., et al. NAB2, a corepressor of NGFI-A (EGR-1), and Krox2O, is induced by proliferative, and differentiative stimuli. Mol Cell Biol 16, 3545–3553 (1996).
44. Morishita, R., et al. In vivo transfection of cis element "decoy" against NF-KB binding site prevents myocardial infarction. Nat. Med. 3, 894–899 (1997).
45. Schneider, A., et al. NF-KB is activated and promotes cell death in focal cerebral ischemia. Nat. Med. 5, 554–550 (1999).
46. Millet, I., et al. Inhibition of NF-KB activity and enhancement of apoptosis by neuropeptide CGRP. J. Biol. Chem. 275,15114–15121 (2000).
47. Cahir-McFarland, E. NF-KB inhibition causes spontaneous apoptosis in EB virus-transformed lymphoblastoid cells. Proc. Natl. Acad. Sci. 97, 6055–6060 (2000).
48. Goldblum, S., Wu, K. & Jay, M. Lung myeloperoxidase as a measure of pulmonary leukostasis in rabbits. J App Physiol 59, 1978–1985 (1985).
49. Ikomminoth, P. Detection of mRNA in tissue sections using DIG-labeled RNA and oligonucleotide probes. In, Nonradioactive In Situ Hybridization Application Manual, 2nd Edition, Boehringer-Mannheim, pp. 126–135 (1996).

What is claimed is:

1. A method for reducing ischemic damage to tissue being transplanted into a subject, which comprises contacting the cells of the tissue ex vivo with a nucleic acid comprising the polynucleotide sequence 5'-CTTGGCCGCTGCCAT-3' (SEQ. ID. NO: 1) prior to the tissue's transplantation into the subject, wherein the nucleic acid inhibits Early Growth Response Factor-1 (Egr-1) expression in the cells of the tissue.

2. The method of claim 1, wherein the nucleic acid comprises a polynucleotide sequence complementary to the polynucleotide sequence of Early Growth Response Factor-1-encoding mRNA.

3. The method of claim 1, wherein the tissue is vascular tissue.

4. The method of claim 1, wherein the tissue is part of a lung, a heart, a kidney, a vein, an artery, a stomach, a colon, a liver, skin, an eye, a pancreas, a finger, a brain, a toe, or a limb.

5. The method of claim 1, wherein the tissue has been subjected to reduced or interrupted blood flow.

6. The method of claim 1, wherein the ischemic damage to the tissue comprises cell death, abnormal cell function, abnormal cell growth, or an inability of the cell to maintain normal function.

* * * * *